US007807686B2

(12) United States Patent
Letourneau et al.

(10) Patent No.: US 7,807,686 B2
(45) Date of Patent: Oct. 5, 2010

(54) 2-(4-OXO-4H-QUINAZOLIN-3-YL)ACETAMIDES AND THEIR USE AS VASOPRESSIN V3 ANTAGONISTS

(75) Inventors: Jeffrey Letourneau, East Windsor, NJ (US); Christopher Riviello, Morrisville, PA (US); Koc-Kan Hoc, West Windsor, NJ (US); Jui-Hsiang Chan, West Windsor, NJ (US); Michael Ohlmeyer, Plainsboro, NJ (US); Patrick Jokiel, Princeton, NJ (US); Irina Neagu, Plainsboro, NJ (US); John Richard Morphy, Newhouse (GB); Susan Elizabeth Napier, Newhouse (GB)

(73) Assignee: N.V. Organon, Oss (NL)

( * ) Notice: Subject to any disclaimer, the term of this patent is extended or adjusted under 35 U.S.C. 154(b) by 0 days.

(21) Appl. No.: 11/908,221

(22) PCT Filed: Mar. 10, 2006

(86) PCT No.: PCT/EP2006/060612
§ 371 (c)(1),
(2), (4) Date: Sep. 10, 2007

(87) PCT Pub. No.: WO2006/095014

PCT Pub. Date: Sep. 14, 2006

(65) Prior Publication Data
US 2008/0214553 A1 Sep. 4, 2008

Related U.S. Application Data

(60) Provisional application No. 60/660,926, filed on Mar. 11, 2005, provisional application No. 60/715,875, filed on Sep. 9, 2005.

(51) Int. Cl.
*A61K 31/517* (2006.01)
(52) U.S. Cl. ............... 514/266.3; 544/287; 546/200; 548/518
(58) Field of Classification Search ............... 514/266.3; 544/287; 546/200; 548/518
See application file for complete search history.

(56) References Cited

U.S. PATENT DOCUMENTS

| 4,438,121 A | 3/1984 | Obitz |
| 6,730,695 B2 | 5/2004 | Roux |
| 7,202,267 B2 | 4/2007 | Aulombard et al. |

FOREIGN PATENT DOCUMENTS

| WO | WO 01/55130 | 8/2001 |
| WO | WO 2004/009585 | 1/2004 |
| WO | WO 2006/095014 A1 | 9/2006 |

OTHER PUBLICATIONS

Jordan, V. C. Nature Reviews: Drug Discovery, 2, 2003, p. 205.*
Vippagunta, et al. Advanced Drug Delivery Reviews, 48, 2001, p. 18.*
Jordan, V. C. Nature Reviews: Drug Discovery, 2, 2003, 205.*
Hackam, et al. JAMA, 296(14), 2006, 1731-1732.*
International Search Report and Written Opinion dated Oct. 3, 2008 for related International Application No. PCT/US07/78022.
International Search Report and Written Opinion dated Oct. 7, 2008 for related International Application No. PCT/US07/77999.
Moss et al., "Catalytic cleavage of active phosphate and ester substrates by iodoso- and iodoxybenzoates," *J. Am. Chem. Soc.* 106(9):2651-2655 (1984).
West, Anthony R., "Chapter 10. Solid Solutions", *Solid State Chemistry and Its Applications*, pp. 358 and 365; John Wiley & Sons, Pub., New York (1988).
International Search Report and Written Opinion for PCT/EP2006/060612 issued Jun. 20, 2006.
Balawant et al., "Synthesis of Pratorimine," *Journal of Natural Product 49* (1986) 445-448.
Bernardini et al., "In vivo and in vitro Effects of Arginine-Vasopressin Receptor Antagonists on the Hypothalamic-Pituitary-Adrenal Axis in the Rat," *Neuroendocrinology 60* (1994) 503-508.
Borcherding et al., "Carbocyclic Nucleosides as Inhibitors of Human Tumor Necrosis Factor-α Production: Effects of the Stereoisomers of (3-Hydroxycyclopentyl)adenines," *J. Med. Chem. 39* (1996) 2615-2620.
De Bold et al., "Arginine Vasopressin Potentiates Adrenocorticotropin Release Induced by Ovine Corticotropin-releasing Factor," *J. Clin. Invest. 73* (1984) 533-538.
De Goeij et al., "Repeated Stress-Induced Activation of Corticotropin-Releasing Factor Neurons Enhances vasopressin Stores and Colocalization with Corticotrophin-Releasing Factor in the Median Eminence of Rats," *Neuroendocrinology 53* (1991) 150-159.

(Continued)

*Primary Examiner*—James O Wilson
*Assistant Examiner*—Douglas M Willis
(74) *Attorney, Agent, or Firm*—Susan L. Hess

(57) ABSTRACT

The present invention relates to 2-(4-oxo4H-quinazolin-3-yl) acetamicle derivatives of formula (I), and to their use as vasopressin V3 antagonists, particularly for the treatment of depression.

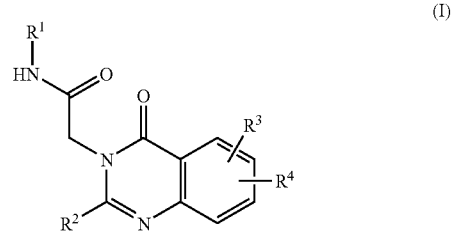

(I)

15 Claims, No Drawings

OTHER PUBLICATIONS

Freidinger et al., "Small Molecule Ligands for Oxytocin and Vasopressin Receptors," *Medicinal Research Reviews 17* (1997) 1-16.

Holsboer et al., "Human Corticotropin-Releasing Hormone in Depression-Correlation with Thyrotropin Secretion following Thyrotropin-Releasing Hormone," *Biol. Psychiatry 21* (1986) 601-611.

Plotsky et al., "Early, postnatal experience alters hypothalamic corticotropin-releasing factor (CRF) mRNA, median eminence CRF content and stress-induced release in adult rats," *Mol. Brain Res. 18* (1993) 195-200.

Rivier et al., "Modulation of stress-induced ACTH release by corticotrophin-releasing factor, catecholamines and vasopressin," *Nature 305* (1983) 325-327.

Scott et al., "Vasopressin and the Regulation of Hypothalamic-Pituitary-Adrenal Axis Function: Implications for the Pathophysiology of Depression," *Life Sciences 62* (1998) 1985-1988.

Sugimoto et al., "Molecular Cloning and Functional Expression of a cDNA Encoding the Human $V_{1b}$ Vasopressin Recepto," *J. Biol. Chem. 269* (1994) 27088-27092.

Venuti et al., "Inhibitors of Cyclic AMP Phosphodiesterase. 3. Synthesis and Biological Evaluation of Pyrido and Imidazolyl Analogues of 1,2,3,5-Tetrahydro-2-oxoimidazo2[,1-*b*]lquinazoline," *J. Med. Chem. 31* (1988) 2136-2145.

* cited by examiner

2-(4-OXO-4H-QUINAZOLIN-3-YL)ACETAMIDES AND THEIR USE AS VASOPRESSIN V3 ANTAGONISTS

CROSS REFERENCE TO RELATED APPLICATION

This application claims priority based on International Patent Application No. PCT/EP2006/060612, filed on Mar. 10, 2006, which claims priority from U.S. provisional application 60/660,926 filed Mar. 11, 2005 and U.S. provisional application 60/715,875 filed Sep. 9, 2005.

FIELD OF THE INVENTION

The present invention relates to 2-(4-oxo-4H-quinazolin-3-yl) acetamide derivatives, to pharmaceutical compositions comprising these compounds and to their use in therapy.

BACKGROUND OF THE INVENTION

The hypothalamo-pituitary-adrenal (HPA) axis is the major stress axis in humans and other mammals. A variety of stressors (and multiple other classes of stimuli) cause release of the hormone ACTH (adrenocorticotropic hormone) from the anterior pituitary gland. ACTH enters the systemic circulation and acts on the adrenal cortex to promote synthesis and release of glucocorticoid hormone (the major endogenous glucocorticoid being cortisol in humans and corticosterone in rodents). The glucocorticoids exert a broad spectrum of effects, the main purpose of which is to mobilise energy sources for successful responsiveness and eventual adaptation to the stressor.

SUMMARY OF THE INVENTION

Abnormally elevated HPA axis activity in man is associated with the development of a variety of psychiatric disturbances, some of which are stress-related in aetiology. Elevated cortisol levels, which are indicative of HPA axis hyperactivity and loss of normal negative feedback regulatory processes, are a common finding in affective disorders and various other psychiatric disturbances, and are widely utilised as a diagnostic tool (Holsboer et al., *Biol. Psych.* 1986, 21, 601-611). It is generally considered that dysregulation of the HPA axis is a relection of enhanced vulnerability and poor adaptation to chronic stress and that chronic stress therefore plays a major role in the development of affective illness (Sperry and carlson, DSM-IV diagnosis to treatment, 2$^{nd}$ Edition, Taylor & Francis, 1996). This central concept is supported by experimental evidence utilising animal models of chronic stress, where abherent HPA function closely resembles that seen in clinical settings (De Goeij et al., *Neuroendocrinology,* 1991, 53, 150-159; Plotsky and Meaney, *Mol. Brain. Res.* 1993, 18, 195-200).

The major secretagogues for ACTH in humans and rats are CRH (corticotropin releasing hormone) and AVP (arginine vasopressin). Within the HPA axis these peptide hormones are synthesised by the parvocellular neurones of the paraventricular nucleus (PVN) of the hypothalamus. The axons of these neurones project to the external zone of the median eminence, from where the hormone products enter the hypophysial portal system to bathe the corticotrope cells that manufacture ACTH. CRH and AVP act synergistically at the corticotrope to regulate ACTH secretion in both rats (Rivier and Vale, *Nature,* 1983, 305, 325-327) and in man (De Bold et al., *J. Clin. Invest.,* 1984, 73, 533-538).

The actions of AVP at the pituitary cortocotrope are mediated by the vasopressin $V_3$ (or $V_{1b}$) receptor, which is known and has been cloned (human receptor: Sugimoto et al., *J. Biol. Chem.,* 1994, 269, 27088-27092). A report of clinical studies in depressed patients in which blunted ACTH responses to CRH could be restored by concomitant administration of desmopressin (dDAVP, an AVP agonist with $V_3$ affinity) confirms the involvement of the $V_3$ receptor in depression (Scott and Dinan, *Life Sciences,* 1998, 62, 1985-1988). A study in rodents with non-selective peptide $V_3$ antagonists indicates that the $V_3$ receptor does play a functional role in control of pituitary ACTH release (Bernardini et al., *Neuroendocrinology,* 1994, 60, 503-508). Vasopressin antagonists are thus utilised to modulate and normalise pituitary ACTH release and subsequent HPA axis dysfunction in CNS disorders which are characterised by abnormal HPA axis negative feedback mechanisms.

In addition to the $V_3$ receptor, vasopressin also activates peripheral receptors, i.e., the $V_{1a}$ receptor, predominantly found on liver and vascular tissue and the $V_2$ receptor, predominantly found on kidney tissue. Interaction at these receptors mediate the pressor and antidiuretic actions of AVP.

Whilst there are several non-peptide low-molecular weight antagonists known which are selective for the $V_{1a}$ or the $V_2$ receptor (for a recent review see Freidinger and Pettibone, *Medicinal Research Reviews,* 1997, 17, 1-16), there are only a small number of non-peptide ligands known with selectivity for the $V_3$ receptor (see for example, WO 01/55130 and WO 04/009585). There exists therefore a need for further non-peptide $V_3$ selective antagonists which are both safe and effective.

DETAILED DESCRIPTION OF THE INVENTION

In a first aspect, the present invention provides a 2-(4-oxo-4H-quinazolin-3-yl)acetamide derivative of formula I

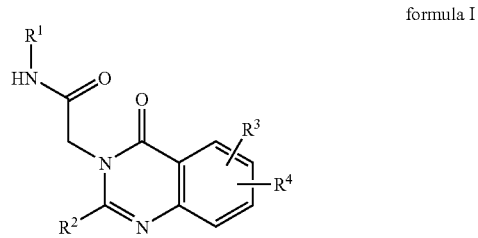

formula I wherein $R^1$ is $C_{1-6}$alkyl, $C_{3-6}$cycloalkyl, $C_{3-6}$cycloalkyl$C_{1-2}$alkyl, $C_{2-6}$alkenyl, $C_{2-6}$alkynyl, phenyl or benzyl, said $C_{1-6}$alkyl, $C_{3-6}$cycloalkyl and $C_{3-6}$cycloalkyl$C_{1-2}$alkyl being optionally substituted with one or more halogens;

$R^2$ is a group selected from $C_{6-10}$aryl and $C_{4-7}$cycloalkyl or $R^2$ is a 5-10 membered heteroaryl ring system comprising a heteroatom selected from N, O and S;

$R^3$ is one or two substituents selected from H, $C_{1-6}$alkyl, $C_{1-6}$alkyloxy and halogen, said $C_{1-6}$alkyl and $C_{1-6}$alkyloxy being optionally substituted with one or more halogens;

$R^4$ is a group located at the 6- or 7-position of the quinazoline ring and is selected from

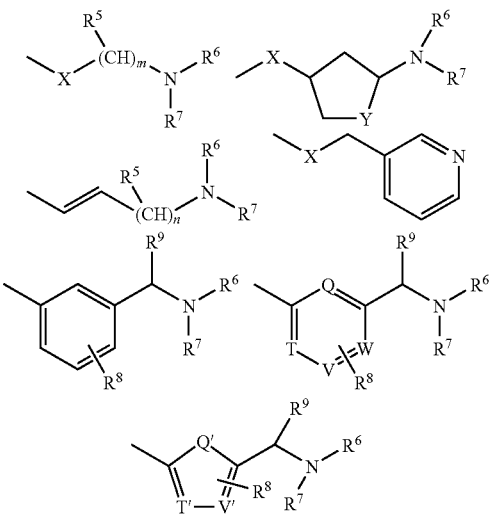

each $R^5$ is independently H or $C_{1-6}$alkyl or one of $R^5$ when joined together with one of $R^6$ or $R^7$ forms a 5-6 membered heterocyclic ring;

$R^6$ and $R^7$ are independently H, $C_{1-6}$alkyl, $C_{3-6}$cycloalkyl, $C_{3-6}$cycloalkyl$C_{1-2}$alkyl, $C_{6-10}$ aryl or $C_{6-10}$aryl$C_{1-2}$alkyl; or $R^6$ and $R^7$ together with the nitrogen to which they are bound form a 4 to 8 membered saturated or unsaturated heterocyclic ring optionally comprising a further heteroatomic moiety selected from O, S and $NR^{10}$, said heterocyclic ring being optionally substituted with one or two substituents selected from halogen, hydroxyl, $C_{1-6}$alkyl, $C_{1-6}$alkyloxy, cyano and $COOR^{11}$ and said heterocyclic ring being optionally fused at two adjacent carbon atoms to a phenyl ring; or one of $R^6$ and $R^7$ when joined together with one of $R^5$ forms a 5-6 membered heterocyclic ring;

$R^8$ is one or two substituents selected from H, $C_{1-6}$alkyl, $C_{1-6}$alkyloxy and halogen or one of $R^8$ when joined together with $R^9$ forms a 5-6 membered ring;

$R^9$ is H or $C_{1-6}$alkyl or $R^9$ when joined together with one of $R^8$ forms a 5-6 membered ring;

$R^{10}$ is H, $C_{1-6}$alkyl or $C_{1-6}$acyl;

$R^{11}$ is H or $C_{1-6}$alkyl;

m is 2-4;

n is 1-2;

X is $CH_2$, O, S, $SO_2$ or $NR^{12}$;

$R^{12}$ is H, $C_{1-6}$alkyl, $C_{1-6}$acyl or a $C_{6-10}$aryl $C_{1-2}$alkyl group, said $C_{6-10}$aryl $C_{1-2}$alkyl group being optionally substituted with methyl or methoxy;

Y is $CH_2$, $(CH_2)_2$ or $(CH_2)_3$;

Q, T, V and W are C or N with the proviso that one of Q, T, V and W is N and the others are C;

Q', T' and V' are selected from C, O, N and S with the proviso that one of Q', T' and V' is O, N, or S and the others are C;

or a pharmaceutically acceptable salt or solvate thereof.

The term $C_{1-6}$ alkyl, as used herein, represents a branched or unbranched alkyl group having 1-6 carbon atoms. Examples of such groups are methyl, ethyl, isopropyl, tertiary butyl, pentyl and hexyl.

The term $C_{2-6}$ alkenyl, as used herein, represents a branched or unbranched alkenyl group having 2-6 carbon atoms and at least one double bond. Examples of such groups are ethenyl and isopropenyl.

The term $C_{2-6}$ alkynyl, as used herein, represents a branched or unbranched alkynyl group having 2-6 carbon atoms and at least one triple bond. Examples of such groups are ethynyl and isopropynyl.

The term $C_{3-6}$ cycloalkyl, as used herein, represents a branched or unbranched cyclic alkyl group having 3-6 carbon atoms. Examples of such groups are cyclopropyl, cyclopentyl and 2-methylcyclopentyl. Similarly, the term $C_{4-7}$ cycloalkyl represents a branched or unbranched cyclic alkyl group having 4-7 carbon atoms.

The term $C_{3-6}$cycloalkyl$C_{1-2}$alkyl, as used herein, represents a $C_{1-2}$ alkyl group which is substituted with a $C_{3-6}$cycloalkyl group. Examples of such groups are cyclopropylmethyl and 2-cyclobutylethyl.

The term $C_{1-6}$alkyloxy, as used herein, represents a branched or unbranched alkyloxy group having 1-6 carbon atoms. Examples of such groups are methoxy, ethoxy, isopropyloxy and tertiary butyloxy.

The term $C_{3-6}$ cycloalkyloxy, as used herein, represents a branched or unbranched cyclic alkyloxy group having 3-6 carbon atoms. Examples of such groups are cyclopropyloxy, cyclopentyloxy and 2-methylcyclopentyloxy. Similarly, the term $C_{4-6}$ cycloalkyloxy represents a branched or unbranched cyclic alkyloxy group having 4-6 carbon atoms.

The term $C_{1-6}$ acyl, as used herein, represents an acyl group derived from a carboxylic acid having 1-6 carbon atoms. The acyl group can comprise a hydrocarbon which may be branched, unbranched, saturated or unsaturated. Examples of such groups include formyl, acetyl, propanoyl, propenoyl and pivaloyl. Also included within the definition of $C_{1-6}$acyl are groups derived from dicarboxylic acids like hemi-malanoyl.

The term $C_{6-10}$aryl, as used herein, represents an aromatic group having 6-10 carbon atoms. Examples of such groups include phenyl and naphthyl.

The term $C_{6-10}$aryl$C_{1-2}$alkyl, as used herein, represents a $C_{1-2}$alkyl group which is substituted with a $C_{6-10}$ aryl group. Examples of such groups include benzyl and phenethyl.

The term halogen, as used herein, represents a fluorine, chorine, bromine or iodine.

The term 5-10 membered heteroaryl ring system comprising a heteroatom selected from N, O and S, as used herein, represents a monocyclic or fused bicyclic 5-10 membered heteroaryl ring system comprising a heteroatom selected from N, O and S. Examples of such groups include furanyl, thienyl, pyrrolyl, pyridinyl, indolyl, benzthienyl and quinolinyl.

Examples of 4 to 8 membered saturated or unsaturated heterocyclic rings formed by $R^6$ and $R^7$ together with the nitrogen to which they are bound and optionally comprising a further heteroatomic moiety selected from O, S and $NR^{10}$ wherein $R^6$, $R^7$ and $R^{10}$ have the previously defined meanings, as used herein, include piperidine homopiperidine, morpholine, thiomorpholine, 4-methylpiperazine and tetrahydropyridine.

In one embodiment of the present invention $R^1$ is $C_{1-6}$alkyl, $C_{3-6}$cycloalkyl or $C_{3-6}$ cycloalkyl$C_{1-2}$alkyl. In a further embodiment $R^1$ is $C_{3-4}$alkyl, $C_{3-4}$cycloalkyl or $C_{3-4}$cycloalkyl$C_{1-2}$alkyl. In a further embodiment $R^1$ is isopropyl, iso-butyl, tertiary-butyl or cyclopropylmethyl.

In another embodiment $R^2$ is $C_{6-10}$aryl, optionally substituted with one to three substituents selected from halogen, hydroxy, cyano, $COOR^3$, $NR^{14}R^{15}$, pyrrole, $C_{1-6}$alkyl, $C_{3-6}$cycloalkyl, $C_{1-6}$alkyloxy and $C_{3-6}$ cycloalkyloxy, said $C_{1-6}$alkyl, $C_{3-6}$ cycloalkyl, $C_{1-6}$ alkyloxy and $C_{3-6}$cycloalkyloxy being optionally substituted with one or more halogens. In a further embodiment $R^2$ is a phenyl ring. In a further embodiment $R^2$ is a 3-substituted phenyl ring. In a further embodiment $R^2$ is a 3-substituted phenyl ring substituted with one to three substituents selected from chloro, fluoro, $C_{1-2}$alkyl, trifluoromethyl, $C_{1-3}$alkyloxy, $C_{1-4}$ cycloalkyloxy and trifluoromethoxy. In a further embodiment $R^2$ is a substituted phenyl ring selected from 3-chlorophenyl, 3-fluorophenyl, 3-methoxyphenyl, 3-trifluoromethoxyphenyl, 3-chloro-4-fluorophenyl, 4-fluoro-3-methoxyphenyl and 3,5-dimethoxyphenyl.

In another embodiment $R^2$ is a 5-10 membered heteroaryl ring system comprising a heteroatom selected from N, O and S and optionally substituted with a substituent selected from methyl, $C_{1-6}$alkyloxy and halogen. In a further embodiment $R^2$ is a 2-thienyl, 3-thienyl or 6-indolyl optionally substituted with chloro or methyl.

In another embodiment, $R^2$ is $C_{4-7}$cycloalkyl. In a further embodiment $R^2$ is cyclohexyl.

In another embodiment $R^3$ is a substituent selected from H, chloro, methyl and methoxy.

In another embodiment $R^3$ is H. In a further embodiment $R^3$ is a substituent at the 7-position of the quinazoline ring.

In another embodiment, $R^4$ is the group

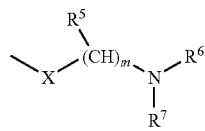

wherein X, m and $R^5$-$R^7$ have the meanings as defined previously. In a further embodiment $R^5$ is methyl and m is 3. In a further embodiment $R^4$ is a group selected from

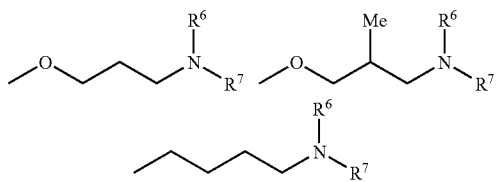

wherein $R^6$ and $R^7$ have the meanings as defined previously.

In another embodiment, $R^4$ is the group

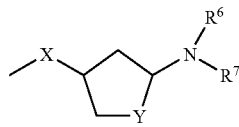

wherein X, Y, $R^6$ and $R^7$ have the meanings as defined previously. In a further embodiment X is O or $CH_2$ and Y is $CH_2$.

In another embodiment, $R^4$ is the group

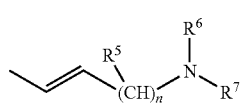

wherein n and $R^5$-$R^7$ have the meanings as defined previously. In a further embodiment $R^5$ is methyl and n is 2.

In another embodiment, $R^4$ is the group

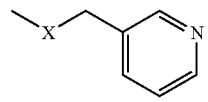

wherein X has the meanings as defined previously. In a further embodiment X is O.

In another embodiment $R^4$ is the group

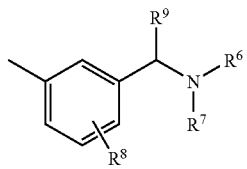

wherein $R^6$ to $R^9$ have the meanings as defined previously. In a further embodiment $R^8$ and $R^9$ are H.

In another embodiment, $R^4$ is the group

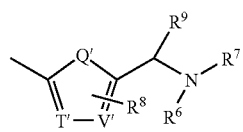

wherein Q', T', V' and $R^6$-$R^9$ have the meanings as defined previously. In a further embodiment $R^8$ and $R^9$ are both H.

In another embodiment, $R^4$ is the group

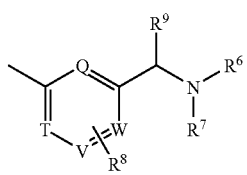

wherein Q, T, V, W and $R^6$-$R^9$ have the meanings as defined previously. In a further embodiment $R^8$ and $R^9$ are both H.

In another embodiment $R^6$ and $R^7$ are independently H, $C_{1-6}$alkyl, $C_{3-6}$cycloalkyl, $C_{3-6}$cycloalkyl$C_{1-2}$alkyl, $C_{6-10}$aryl or $C_{6-10}$aryl$C_{1-2}$alkyl. In a further embodiment $R^6$ and $R^7$ are independently H or $C_{1-4}$alkyl.

In another embodiment, $R^6$ and $R^7$ together with the nitrogen to which they are bound form a 4 to 6 membered heterocyclic ring optionally comprising a further heteroatomic moiety selected from O, S or $NR^{10}$, said heterocyclic ring being optionally substituted with a hydroxyl substituent, wherein $R^{10}$ has the previously defined meaning. In a further embodiment $R^6$ and $R^7$ together with the nitrogen to which they are bound form a heterocyclic ring selected from pyrrolidine, piperidine, 3-hydroxypiperidine and morpholine.

In a further embodiment is a 2-(4-oxo-4H-quinazolin-3-yl) acetamide selected from:

2-[2-(3-Chloro-4-fluorophenyl)-4-oxo-6-(3-piperidin-1-yl-propoxy)-4H-quinazolin-3-yl]-N-isopropylacetamide;

N-Isopropyl-2-[2-(3-methoxyphenyl)-4-oxo-6-(3-piperidin-1-yl propoxy)-4H-quinazolin-3-yl]acetamide;

2-[2-(4-Fluoro-3-methoxyphenyl)-4-oxo-6-(3-piperidin-1-ylpropoxy)-4H-quinazolin-3-yl]-N-isopropylacetamide;

2-[2-(3-Chlorophenyl)-6-[3-(4-hydroxypiperidin-1-yl)propoxy]-4-oxo-4H-quinazolin-3-yl]-N-isopropylacetamide;

2-[2-(3-Chlorophenyl)-4-oxo-6-(3-piperidin-1-ylpropoxy)-4H-quinazolin-3-yl]-N-isopropylacetamide;

(S)-(+)-2-[2-(3-Chlorophenyl)-6-(2-methyl-3-pyrrolidin-1-yl propoxy)-4-oxo-4H-quinazolin-3-yl]-N-isopropylacetamide;

2-[6-(5-Dimethylaminomethyl-2-fluorophenyl)-2-(3-methoxyphenyl)-4-oxo-4H-quinazolin-3-yl]-N-isopropylacetamide;

2-[6-(3-Dimethylaminomethylphenyl)-2-(3-methoxyphenyl)-4-oxo-4H-quinazolin-3-yl]-N-isopropylacetamide;

N-tert-Butyl-2-[2-(3-chlorophenyl)-4-oxo-6-(3-pyrrolidin-1-ylpropoxy)-4H-quinazolin-3-yl]acetamide and 2-[6-(3-Dimethylaminomethylphenyl)-2-(3-methoxyphenyl)-4-oxo-4H-quinazolin-3-yl]-N-isopropylacetamide or a pharmaceutically acceptable salt or solvate thereof.

The compounds of the present invention are prepared by methods well known in the art of organic chemistry. See, for example, J. March, '*Advanced Organic Chemistry*' 4$^{th}$ Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts '*Protective Groups in Organic Synthesis*' 2$^{nd}$ Edition, John Wiley and Sons, 1991. The protective groups are optionally removed at a convenient subsequent stage using methods well known in the art.

Compounds of formula I wherein R$^4$ is the group

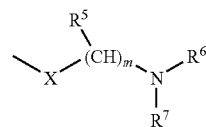

and X is O (shown as 8 below) can be prepared by the general four stage synthetic sequence shown in Scheme 1. Firstly an anthranilic acid of formula 2, is reacted with a glycine amide of formula 3 in the presence of a suitable amide bond coupling reagent to give the coupled product 4. One example of such a coupling reagent would be EDCI. The coupling reagent is added either alone or in the presence of an additive such as HOBt and in a suitable inert solvent such as dichloromethane or DMF. The necessary anthranilic acids 2 and glycine amides 3 are either commercially available or they can readily be prepared by procedures well known in the art. The intermediate quinazolines of general formula 6 can be made by condensation of the imidate salt 5 in a suitable solvent such as ethanol and at elevated temperatures such as at reflux. The free hydroxyl group is then functionalised with an alcohol of formula 7 utilizing, for example, standard Mitsonobu reaction conditions, i.e., in the presence of triphenylphosphine and diethylazodicarboxylate or DIAC to provide the desired product 8.

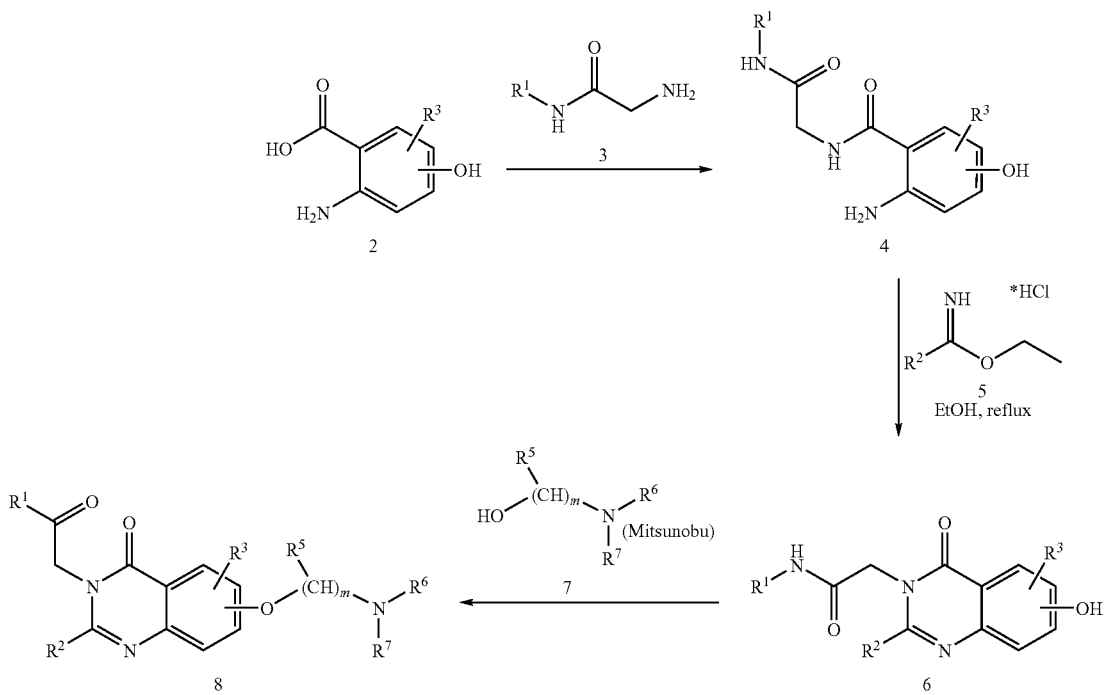

Scheme 1

Alternatively, the hydroxyquinazolinone intermediate 6 can be formed by condensation of intermediate 9 with a suitable aldehyde, R$^2$CHO, followed by subsequent oxidation of the resultant dihydroquinazolinone intermediate 10 with a suitable oxidant such as MnO$_2$, DDQ, or CuCl$_2$ (Scheme 2).

Scheme 2

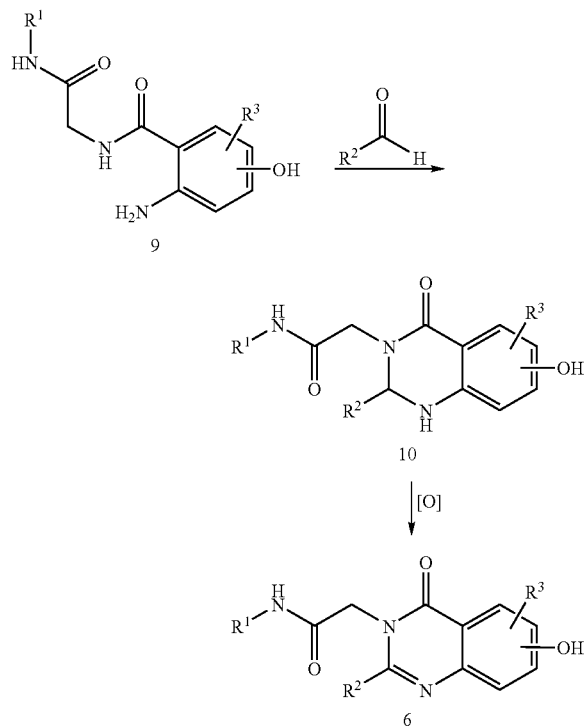

The amide intermediate 4 can alternatively be prepared by reaction of an isatoic anhydride of general formula 11 with a glycine amide of formula 3 in a polar aprotic solvent such as acetonitrile. The isatoic anhydrides 11 are either commercially available or can readily be prepared by reaction of a suitable anthranilic acid of formula 2 with a carbonylating reagent such as phosgene or triphosgene (Scheme 3).

Scheme 3

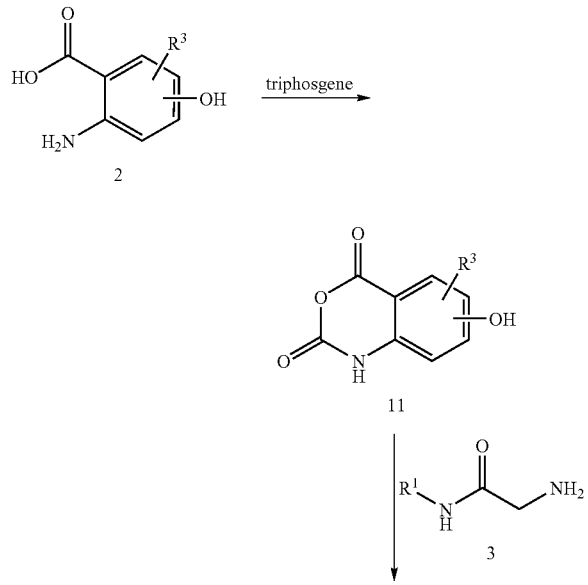

The desired products 8 can also be prepared by alkylation of the hydroxy quinazolinone intermediate 6 in the presence of a suitable base with a compound of formula 12 wherein L is a suitable leaving group. A suitable base would be, for example, a metal carbonate such as potassium carbonate or cesium carbonate. Suitable leaving groups would be, for example, a mesylate or tosylate group or a halide (Scheme 4)

Scheme 4

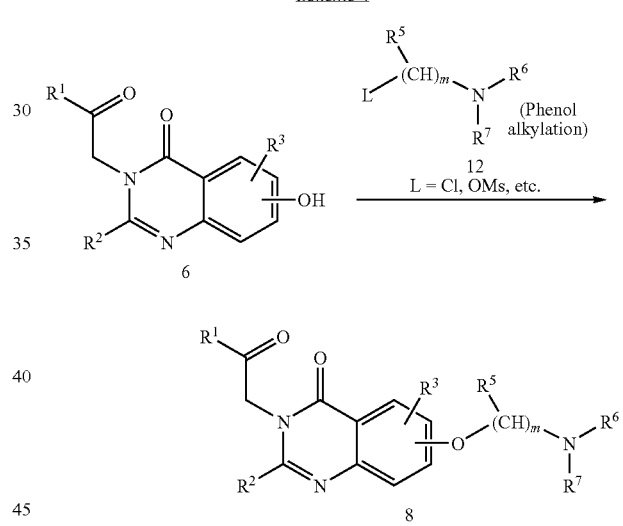

The desired products 8 can also alternatively be prepared by a two-step procedure involving first, a base-mediated alkylation of a hydroxy quinazolinone 6, with a suitable dihaloalkane, such as 3-bromo-1-chloropropane, followed by nucleophilic displacement with an amine of formula $HNR^6R^7$ (Scheme 5).

Scheme 5

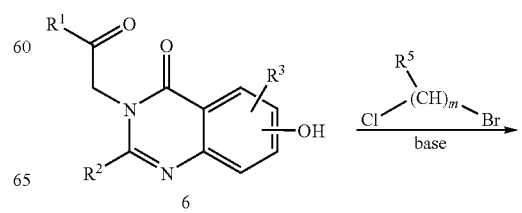

-continued

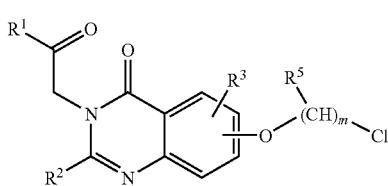

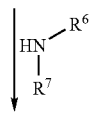

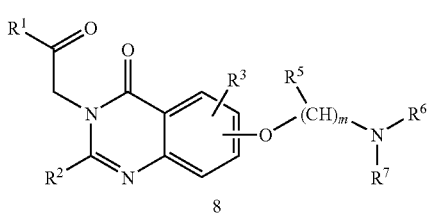

8

A related three-step procedure by which the desired products 8 can also be prepared involves firstly alkylation of the aforementioned hydroxy quinazolinone 6 with a suitable haloalkanol, such as 3-bromopropan-1-ol, followed by conversion of the hydroxyl group to a suitable leaving group, such as halide or mesylate, utilizing various methods known to one skilled in the art, and finally, displacement of said leaving group with an amine of formula HNR8R9 to provide the desired product 8 (Scheme 6).

Intermediates of formula I, wherein $R^4$ is halogen, 15, can be prepared by analogous procedures to those employed for the corresponding derivatives wherein $R^4$ is hydroxyl shown in Schemes 1-3 (i.e., from anthranilic acids 13 and via amides 14). As before the starting anthranilic acids are either commercially available or they can readily be prepared by procedures well known in the art.

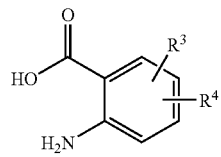

13

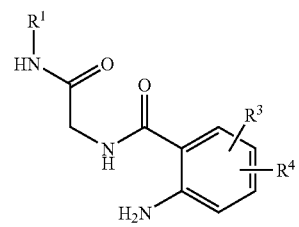

14

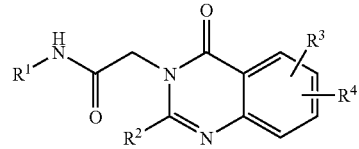

15

$R^4$=halogen

Compounds of formula I wherein $R^4$ is a group having the formula

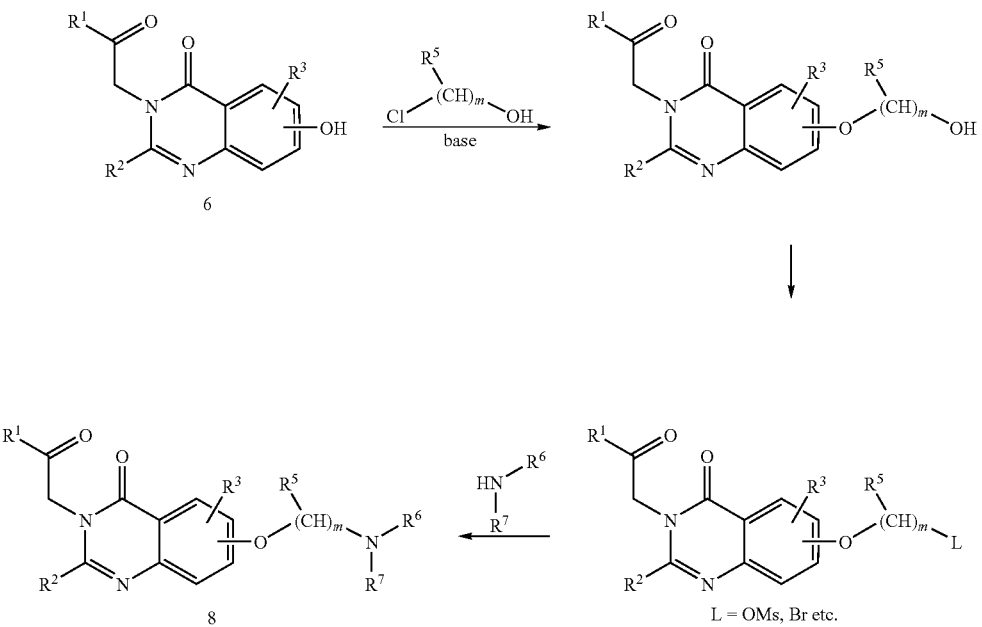

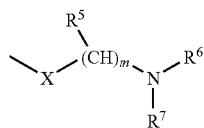

and X is $NR^{15}$ (17) can be prepared by reaction of intermediates of formula I wherein $R^4$ is a suitably reactive group such as halogen (e.g. bromo or iodo), triflate, etc. with diamines of formula 16 in the presence of a suitable catalyst system, such as $Pd_2(dba)_3$ and Binap, under conditions well known in the art (Scheme 7). Intermediates of formula I wherein $R^4$ is triflate can readily be prepared from the corresponding alcohols 6 using procedures well known in the art, for example by treatment of alcohols 6 with trifluoromethanesulfonic anhydride and pyridine.

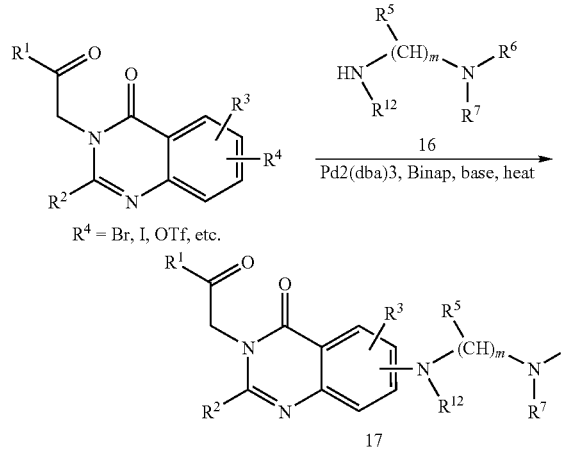

Compounds of formula I wherein $R^4$ is a group selected from

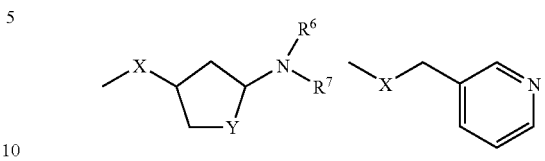

and X is O or $NR^{12}$ can be prepared using analogous procedures and/or reaction sequences to those described above in Schemes 5-7.

Compounds of formula 1, wherein $R^4$ is the group

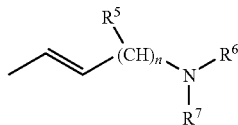

(20) can be prepared by first reacting an intermediate of formula I wherein $R^4$ is a group such as halide or triflate with a terminal alkene of formula 18 (wherein L is a displaceable group such as halide or a group such as hydroxyl which can subsequently be converted to a displaceable group such as halide, mesylate, or tosylate) in the presence of a base such as triethylamine, a suitable catalyst such as $Pd(OAc)_2$, and a triarylphosphine ligand such as tri(o-tolyl)phosphine to give the intermediate 19. The amine 20 is then formed from the alkene 19 by displacement of leaving group L with an aliphatic amine of formula $HNR^6R^7$. The corresponding saturated derivative 21 can be obtained by hydrogenation of the unsaturated amine 20 in the presence of, for example, a palladium on carbon catalyst (Scheme 8).

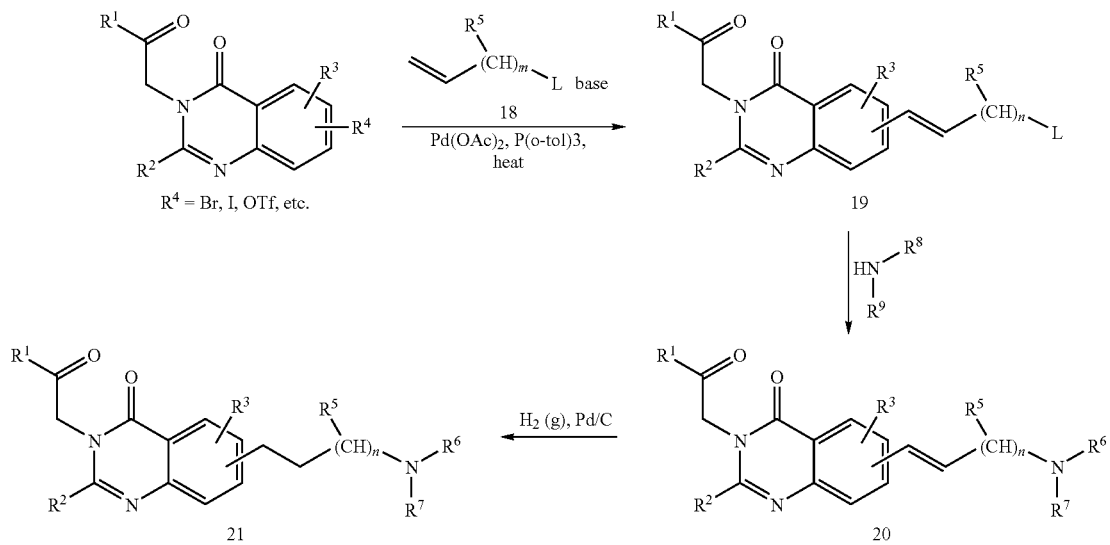

Compounds of formula I, wherein R⁴ is the group

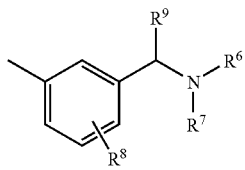

in the presence of a suitable catalyst such as Pd(PPh₃)₄ followed by conversion to the desired amine by a variety of methods familiar to one skilled in the art. For example, adduct 26 can be obtained upon reaction of intermediate 1, wherein R⁴ is halogen or triflate with the boronate 25 in the presence of triphenylphosphine. This can then be converted to intermediate 27 in which the hydroxyl group has been converted to a leaving group, such as halide or mesylate. Compound 27 can then in turn be treated with an amine of formula NHR⁶R⁷ to afford the desired product 28 (Scheme 9).

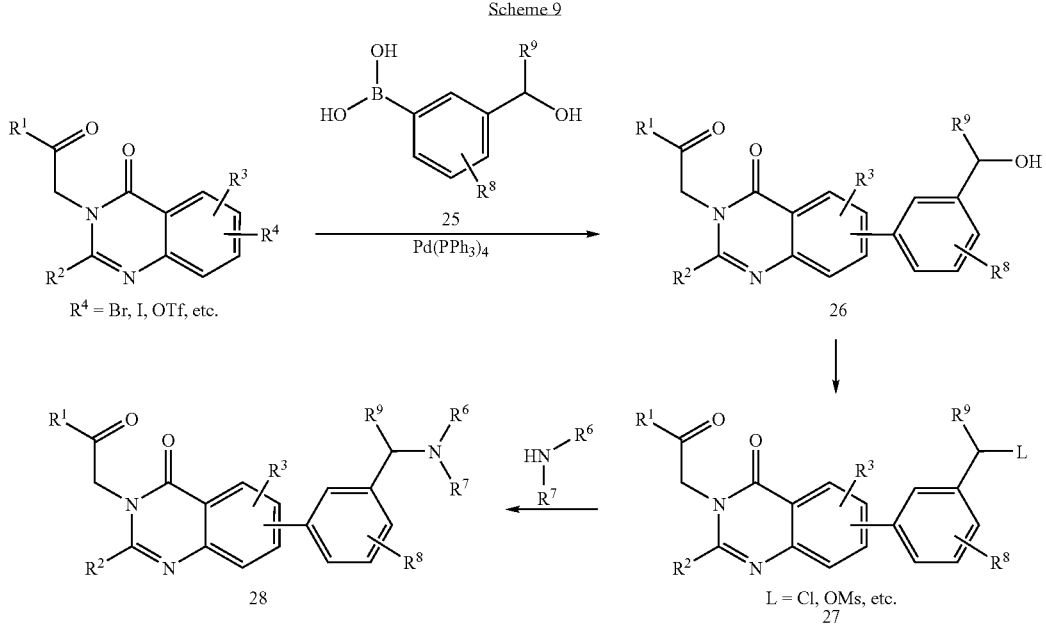

(22) can be prepared by coupling of an intermediate of formula I wherein R⁴ is a suitably reactive group such as halide (e.g. bromo or iodo) or triflate, with a boronic acid or ester of formula 23 or 24 (Q=B(OH)₂ or B(OR)₂)

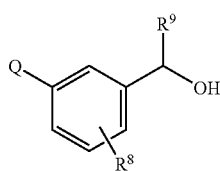

23

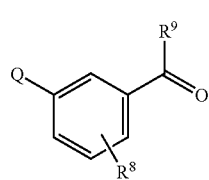

24

Alternatively, adduct 30 can be obtained by reaction of intermediate I with boronate 29. This can then be converted to the desired amine product 28 upon treatment with NHR⁶R⁷ in the presence of a suitable reducing agent such as sodium triacetoxyborohydride or sodium cyanoborohydride (Scheme 10).

Scheme 10

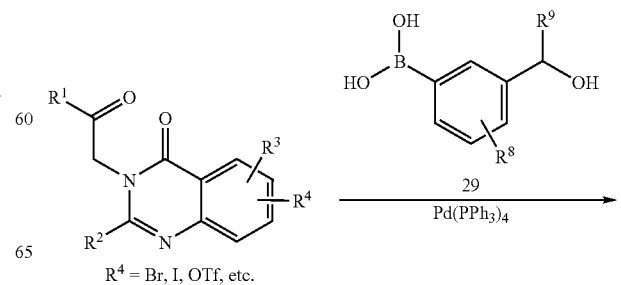

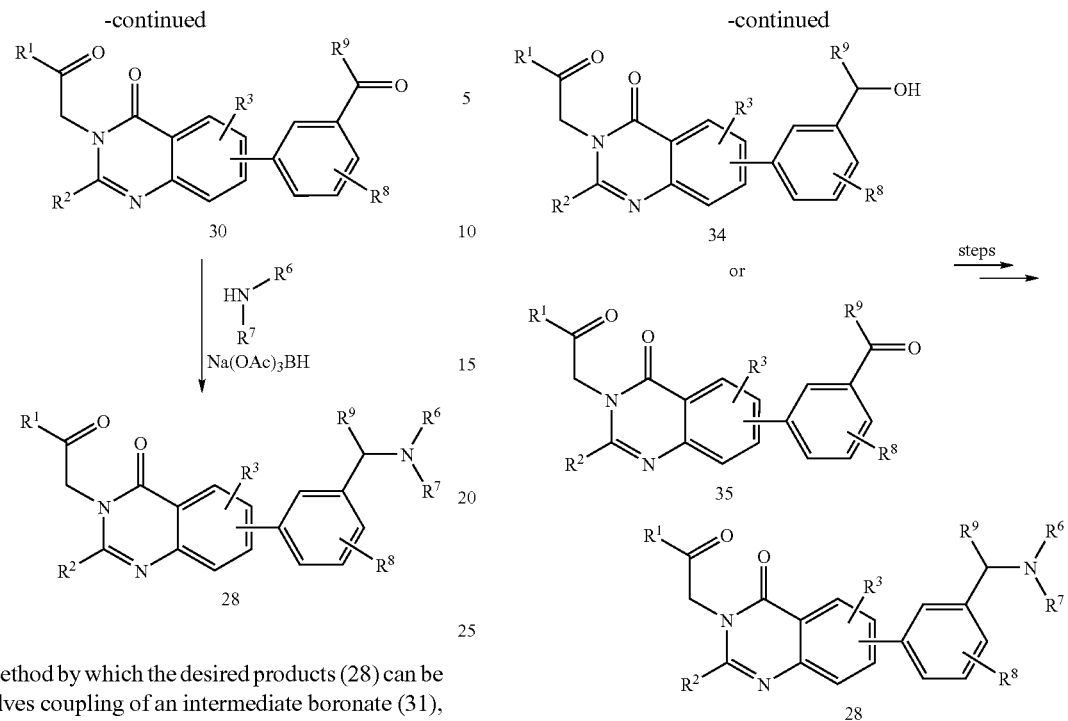

A further method by which the desired products (28) can be obtained involves coupling of an intermediate boronate (31), prepared via an intermediate halide or triflate of formula I ($R^4$=halide or triflate) by reaction of said halide or triflate with bis(pinacolato)diboron in the presence of a suitable catalyst such as $PdCl_2$(dppf) and a base such as KOAc (Scheme 11). This can then be coupled with an aryl halide or triflate of formula 32 or 33 (Q=halide or triflate) using analogous procedures to those shown in Schemes 9 and 10 to provide the adducts 34 and 35 which are then converted as shown in Schemes 9 and 10 to the product 28.

Scheme 11

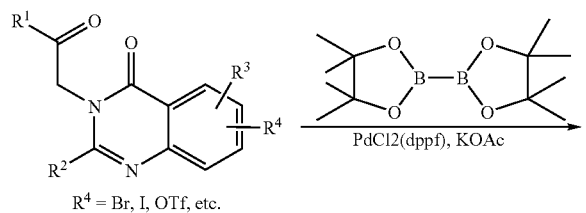

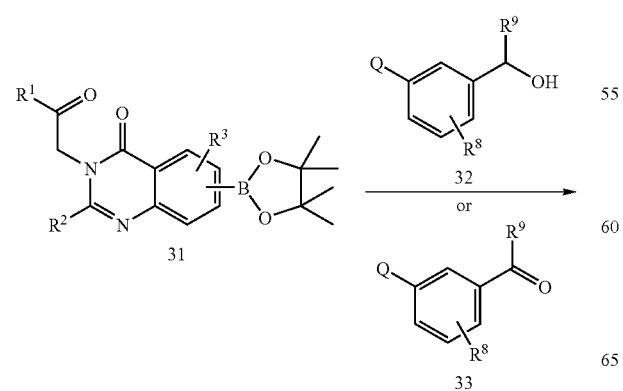

Compounds of formula I, wherein $R^4$ is a group selected from

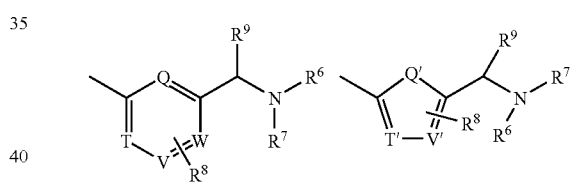

can prepared using the same general procedures and/or reaction sequences described above in Schemes 9-11.

It will be readily appreciated by one skilled in the art that the quinazolinones of general formula I can be prepared using the general procedures and/or reaction sequences described above in any suitable order. For example, whereas the processes detailed above describe introduction of the $R^4$ groups later in the syntheses utilizing preformed quinazolinone intermediates, it will be recognized that, in some cases, the $R^4$ groups can be introduced before the formation of the quinazolinone ring system.

Hence compounds of formula I wherein $R^4$ is a group having the formula

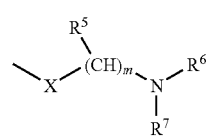

and X is O can be prepared in 5 stages from phenol 34 as shown in Scheme 12. The phenol 34 is either commercially available or prepared using procedures well known in the art of organic chemistry. The phenol can be alkylated using analogous procedures to those shown above in Scheme 1 and Schemes 4-6 to provide the amino ether 35. Upon treatment with either aqueous acid or base, for example, using 6N hydrochloric acid at reflux, the ester groups can then be hydrolysed to yield the anthranilic acid intermediate 36. This can then be coupled with the glycine amide 3, using analogous procedures to those indicated previously (see Scheme 1) to yield the coupled amide 37. The desired imidazolines 8 can then be prepared upon reaction of 37 with an imidate*HCl salt of formula 5 (as previously described—Scheme 1) or upon reaction of 37 with an aldehyde $R^2$CHO followed by oxidation (as previously described—Scheme 2).

and X is $NR^{12}$ or S can be prepared in 6 stages from the required fluoro-2-nitrobenzoic acid 38. The fluoro-2-nitrobenzoic acid is either commercially available or can be prepared using procedures well known in the art of organic chemistry. The acid 38 is coupled with a glycine amide of formula 3 using analogous procedures to those indicated previously (see Scheme 1) to yield the amide 39. This in turn is then treated with amine or thiol 40 in an inert polar, aprotic solvent such as DMF, DMSO or DMP at elevated temperatures and in the presence of a suitable base (for example, sodium hydride in the case of thiols or potassium or cesium carbonate in the case of amines) to afford the adduct 41. The

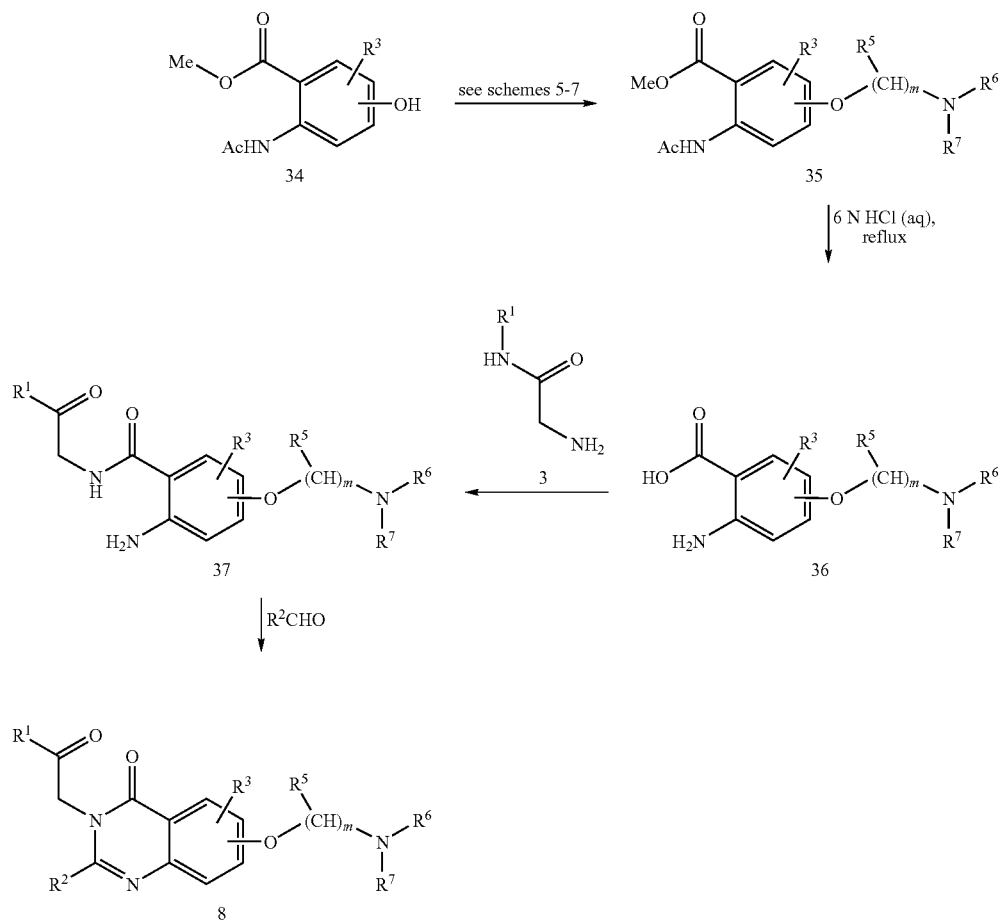

Compounds of formula I wherein $R^4$ is a group having the formula

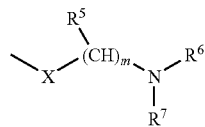

nitro group is then reduced to give the aniline 42 using methods well known in the art, for example, reduction under a hydrogen atmosphere and in the presence of a suitable catalyst such as palladium on carbon. Finally, the desired imidazolines 43 are prepared upon reaction of 42 with an imidate*HCl salt of formula 5 (as previously described—Scheme 1) or upon reaction of 42 with an aldehyde $R^2$CHO followed by oxidation (as previously described—Scheme 2).

Scheme 13

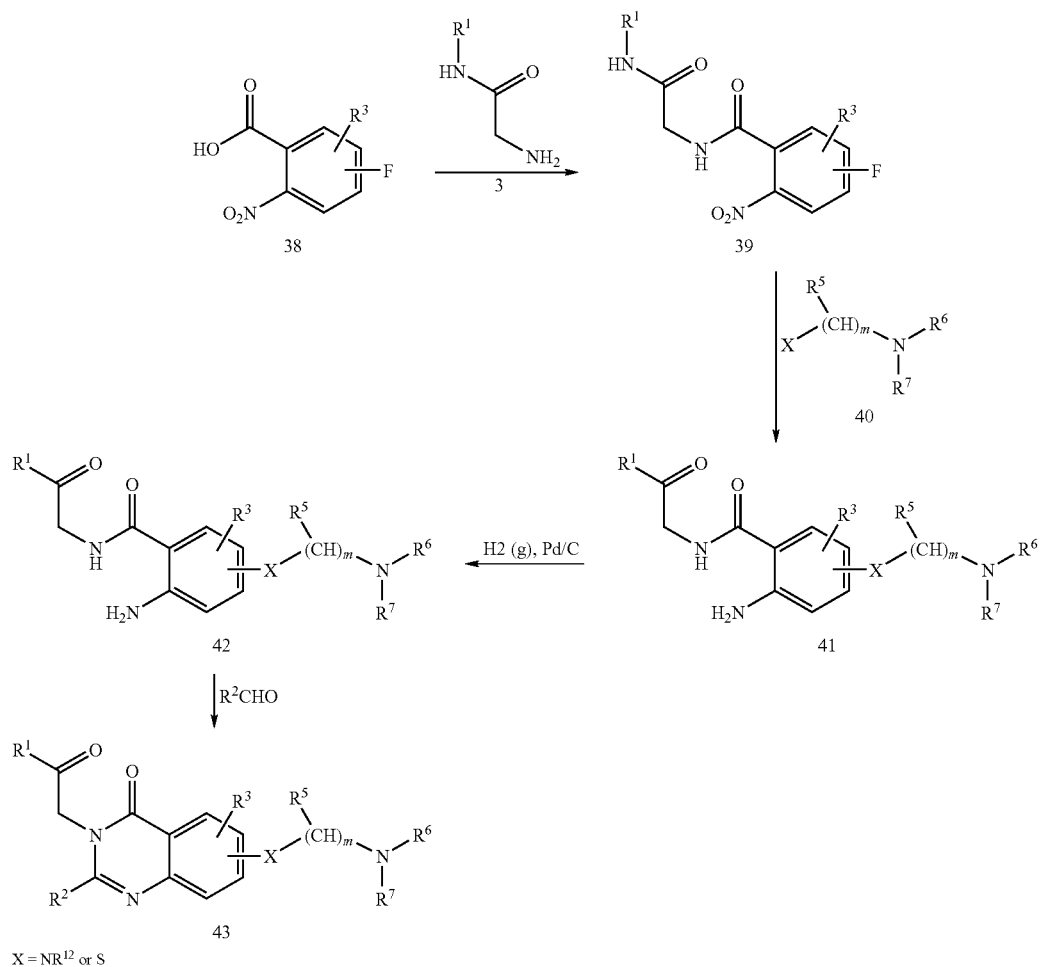

Compounds of formula I wherein $R^4$ is a group having the formula

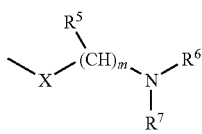

and X is $SO_2$ can be prepared by oxidation of the corresponding sulphides using, for example, m-chloroperoxybenzoic acid in dichloromethane.

The present invention also includes within its scope all stereoisomeric forms of compounds resulting, for example, because of configurational or geometrical isomerism. Such stereoisomeric forms are enantiomers, diastereoisomers, cis and trans isomers etc. For example, in the case where $R^1$ is 2-methylcyclopropylamine the compound exists as a pair of enantiomers. In the case where $R^4$ comprises an alkene fragment, both (Z) and (E) stereoisomeric forms of the compound are possible. In the case of the individual enantiomers of compounds of formula I or salts or solvates thereof, the present invention includes the aforementioned stereoisomers substantially free, i.e., associated with less than 5%, preferably less than 2% and in particular less than 1% of the other enantiomer. Mixtures of stereoisomers in any proportion, for example a racemic mixture comprising substantially equal amounts of two enantiomers are also included within the scope of the present invention.

For chiral compounds, methods for asymmetric synthesis whereby the pure stereoisomers are obtained are well known in the art, e.g., synthesis with chiral induction, synthesis starting from chiral intermediates, enantioselective enzymatic conversions, separation of stereoisomers using chromatography on chiral media. Such methods are described in *Chirality In Industry* (edited by A. N. Collins, G. N. Sheldrake and J. Crosby, 1992; John Wiley). Likewise methods for synthesis of geometrical isomers are also well known in the art.

The compounds of the present invention, in the form as a free base, are isolated from reaction mixtures as pharmaceutically acceptable salts. These salts are also obtained by treatment of said free base with an organic or inorganic acid, for example, hydrogen chloride, hydrogen bromide, hydrogen iodide, sulfuric acid, phosphoric acid, acetic acid, trifluoroacetic acid, propionic acid, glycolic acid, maleic acid, malonic acid, methanesulfonic acid, fumaric acid, succinic acid, tartaric acid, ciric acid, benzoic acid and ascorbic acid.

The compounds of the present invention exist in both solvated and unsolvated forms, including hydrated forms. These forms are also encompassed within the scope of the present invention.

The compounds of the present invention also exist as amorphous forms. Multiple crystalline forms are also possible. All these physical forms are included within the scope of the present invention.

In a further aspect, the compounds of the present invention and their pharmaceutically acceptable salts and solvates are useful in therapy. As such the compounds of the present invention are useful for the manufacture of a medicament for the treatment or prevention of diseases influenced by modulation of the activity of the HPA axis. In particular the compounds are useful for the manufacture of a medicament for the treatment of schizophrenia, anxiety, hot flushes, addiction, anorexia nervosa, stress-related disorders and Alzheimer's dementia.

In a further aspect, the compounds of the present invention are useful for the manufacture of a medicament for the treatment or prevention of depression. Depression states in the treatment of which the compounds of the present invention and their pharmaceutically acceptable salts and solvates are particularly useful are those classified as mood disorders in the *Diagnostic and Statistical Manual of Mental Disorders, Fourth Edition-Text Revised*, American Psychiatric Association, Washington D.C. (2000), including mood episodes, depressive disorders, bipolar disorders and other mood disorders.

The present invention further includes a method for the treatment of a mammal, including a human, suffering from or liable to suffer from depression or any of the aforementioned disorders, which comprises administering an effective amount of a compound of the present invention or a pharmaceutically acceptable salt or solvate thereof.

The amount of a compound of the present invention or a pharmaceutically acceptable salt or solvate thereof, also referred to herein as the active ingredient, which is required to achieve a therapeutic effect will, of course, vary with the particular compound, the route of administration, the age and condition of the recipient, and the particular disorder or disease being treated.

A suitable daily dose for any of the above mentioned disorders will be in the range of 0.001 to 50 mg per kilogram body weight of the recipient (e.g. a human) per day, preferably in the range of 0.01 to 20 mg per kilogram body weight per day. The desired dose may be presented as multiple subdoses administered at appropriate intervals throughout the day.

Whilst it is possible for the active ingredient to be administered alone, it is preferable to present it as a pharmaceutical formulation. The present invention therefore also provides a pharmaceutical composition comprising a compound according to the present invention in admixture with one or more pharmaceutically acceptable excipients, such as the ones described in Gennaro et. al., Remmington: *The Science and Practice of Pharmacy*, 20$^{th}$ Edition, Lippincott, Williams and Wilkins, 2000; see especially part 5: pharmaceutical manufacturing. Suitable excipients are described e.g., in the Handbook of Pharmaceutical Excipients, 2$^{nd}$ Edition; Editors A. Wade and P. J. Weller, American Pharmaceutical Association, Washington, The Pharmaceutical Press, London, 1994. Compositions include those suitable for oral, nasal, topical (including buccal, sublingual and transdermal), parenteral (including subcutaneous, intravenous and intramuscular) or rectal administration.

The mixtures of a compound according to the present invention and one or more pharmaceutically acceptable excipient or excipients may be compressed into solid dosage units, such as tablets, or be processed into capsules or suppositories. By means of pharmaceutically suitable liquids the compounds can also be applied as an injection preparation in the form of a solution, suspension, emulsion, or as a spray, e.g., a nasal or buccal spray. For making dosage units e.g., tablets, the use of conventional additives such as fillers, colorants, polymeric binders and the like is contemplated. In general, any pharmaceutically acceptable additive can be used. The compounds of the invention are also suitable for use in an implant, a patch, a gel or any other preparation for immediate and/or sustained release.

Suitable fillers with which the pharmaceutical compositions can be prepared and administered include lactose, starch, cellulose and derivatives thereof, and the like, or mixtures thereof used in suitable amounts.

The invention is further illustrated by the following examples.

Synthesis of Precursors and Common Intermediates for Compounds of the Present Invention Procedure I INTERMEDIATE I.1:
2-Amino-N-isopropylacetamide

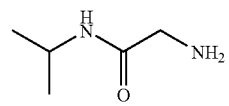

a) (Isopropylcarbamoylmethyl)carbamic Acid Benzyl Ester

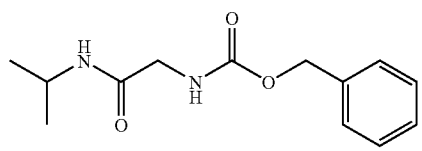

To a solution of N-Cbz-glycine (20.9 g, 100 mmol) in THF (400 mL) at 0° C. was added N-methylmorpholine (NMM) (12.1 mL, 110 mmol) and i-butylchloroformate (13 mL, 100 mmol). The resultant mixture was stirred at 0° C. for 2 min and then i-propylamine (9.4 mL, 110 mmol) was added. The reaction mixture was warmed to room temperature and stirred at this temperature for 16 h. The mixture was filtered through a pad of CELITE™ and concentrated in vacuo. The crude residue was dissolved in ethyl acetate (500 mL) and washed with 1N HCl (aq.) (1×100 mL), sat. NaHCO$_3$ (aq.) (1×100 mL) and brine (1×100 mL). The organic layer was dried (MgSO$_4$), filtered and concentrated in vacuo to afford (isopropylcarbamoylmethyl)carbamic acid benzyl ester as a white solid (24.5 g, 98 mmol, 98%) which was used without further purification in the next reaction.

Data: $^1$H NMR (300 MHz, CDCl$_3$): δ 7.37 (m, 5H), 5.78 (br s, 1H), 5.41 (br s, 1H), 5.15 (s, 2H), 4.07 (septet, 1H), 3.82 (d, 2H), 1.15 (d, 6H) ppm.

b) 2-Amino-N-isopropylacetamide

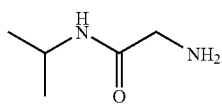

10% Pd/C (425 mg) was added to a solution of (isopropylcarbamoylmethyl)carbamic acid benzyl ester (10 g, 40 mmol) in ethanol (200 mL) and shaken in a Parr shaker under a hydrogen atmosphere (50 p.s.i.) for 16 h. The reaction mixture was filtered through a pad of CELITE™ and the solvent removed in vacuo. This afforded 2-amino-N-isopropylacetamide (INTERMEDIATE I.1) as a clear, colourless oil (5.1 g, 40 mmol, 100%).

Data for 2-amino-N-isopropylacetamide (INTERMEDIATE I.1): $^1$H NMR (300 MHz, CDCl$_3$): δ 7.05 (brs, 1H), 4.11 (septet, 1H), 3.33 (s, 2H), 1.48 (brs, 2H, amine N$\underline{H}_2$), 1.15 (d, 6H) ppm.

Similarly prepared were:
INTERMEDIATE I.2: 2-Amino-N-benzylacetamide
INTERMEDIATE I.3: 2-Amino-N-ethylacetamide
INTERMEDIATE I.4: 2-Amino-N-propylacetamide
INTERMEDIATE I.5: 2-Amino-N-tert-butylacetamide
INTERMEDIATE I.6: 2-Amino-N-isobutylacetamide
INTERMEDIATE I.7: 2-Amino-N-cyclopropyl methylacetamide
INTERMEDIATE I.8: 2-Amino-N-cyclopropylacetamide
INTERMEDIATE I.9: 2-Amino-N-cyclopentylacetamide
INTERMEDIATE I.10: N-Allyl-2-aminoacetamide
INTERMEDIATE I.11: 2-Amino-N-phenylacetamide
INTERMEDIATE I.12: 2-Amino-N-(2,2,2-trifluoroethyl)acetamide Procedure II INTERMEDIATE II.1: 2-Amino-5-hydroxy-N-(isopropylcarbamoylmethyl)benzamide

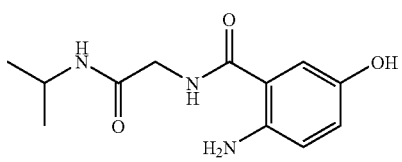

Method A

To a solution of 5-hydroxyanthranilic acid (7.6 g, 49.3 mmol) in DMF (100 mL) was added 1-[3-dimethylaminopropyl]-3-ethylcarbodiimide hydrochloride (EDC) (10.4 g, 54.2 mmol), 1-hydroxybenzotriazole hydrate (HOBt) (7.3 g, 54.2 mmol), 2-amino-N-isopropyl-acetamide hydrochloride (INTERMEDIATE I.1) (7.5 g, 49.3 mmol) and N,N-diisopropylethylamine (DIEA) (9.50 mL, 7.0 g, 54.2 mmol). The reaction mixture was stirred at room temperature for 24 h, concentrated in vacuo to half of its volume and partitioned between diethyl ether (100 mL) and 1N HCl (aq.) (400 mL). The aqueous layer was extracted with diethyl ether (5×100 mL), and ethyl acetate (5×100 mL). The aqueous layer was then concentrated under high vacuum to dryness. The red residue was dissolved in ethanol (20 mL) followed by addition of dichloromethane (1 L). The resulting brown precipitate was filtered under vacuum and washed with a minimum amount of methanol to give the desired product 2-amino-5-hydroxy-N-(isopropylcarbamoylmethyl)benzamide (INTERMEDIATE I.1) hydrochloride salt as a white solid (5.7 g, 19.8 mmol, 40%).

Data for 2-amino-5-hydroxy-N-(isopropylcarbamoylmethyl)benzamide (INTERMEDIATE II.1) hydrochloride salt: $^1$H NMR (300 MHz, CD$_3$OD): δ 7.28-7.25 (m, 2H), 7.05 (dd, 1H), 4.03 (s, 2H), 4.05-4.00 (m, 1H), 1.20 (d, 6H) ppm; MS (ESI) m/z: 252 ([M+H]$^+$).

Method B a) 6-Hydroxy-1H-benzo[d][1,3]oxazine-2,4-dione

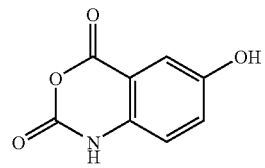

To a suspension of 5-hydroxyanthranilic acid (15.3 g, 100 mmol) in THF (400 mL) at 0° C. was added triphosgene (10.1 g, 34 mmol). The resultant mixture was stirred for 5 min at 0° C. and then allowed to warm to room temperature over 6 h. The reaction mixture was cooled at 0° C. overnight and the resultant gray precipitate collected by filtration to afford 6-hydroxy-1H-benzo[d][1,3]oxazine-2,4-dione (9.8 g, 55 mmol, 55%). The filtrate was concentrated in vacuo, the resultant solid triturated with diethyl ether and collected by filtration to afford additional product (7.3 g, 41 mmol, 41%).

Data for 6-hydroxy-1H-benzo[d][1,3]oxazine-2,4-dione: $^1$H NMR (300 MHz, d$^6$-DMSO): δ 11.5 (s, 1H), 9.86 (br s, 1H), 7.21 (m, 2H), 7.01 (d, 1H) ppm.

b) 2-Amino-5-hydroxy-N-(isopropylcarbamoylmethyl)benzamide

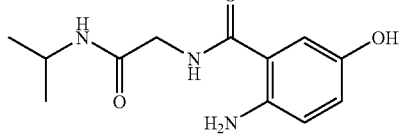

To a solution of 2-amino-N-isopropylacetamide (INTERMEDIATE I.1) (4.77 g, 41.1 mmol) in acetonitrile (50 mL) was added 6-hydroxy-1H-benzo[d][1,3]oxazine-2,4-dione (6.13 g, 34.2 mmol). The mixture was stirred for 16 h at room temperature during which time a very thick precipitate formed. The mixture was diluted with dichloromethane (100 mL) and the solid collected by filtration and washed with dichloromethane (2×20 mL) to afford 2-amino-5-hydroxy-N-(isopropylcarbamoylmethyl)benzamide (INTERMEDIATE II.1) (6.75 g, 32.0 mmol, 78%).

Data for 2-amino-5-hydroxy-N-(isopropylcarbamoylmethyl)benzamide (INTERMEDIATE II.1): $^1$H NMR (300 MHz, CD$_3$OD): δ 7.81 (br d, 1H, amide N$\underline{H}$), 6.98 (d, 1H), 6.77 (dd, 1H), 6.69 (d, 1H), 4.01 (m, 1H), 3.94 (s, 2H), 1.16 (d, 6H) ppm.

Similarly prepared were:

INTERMEDIATE II.2: 2-Amino-N-[(cyclopropyl methylcarbamoyl)methyl]-5-hydroxybenzamide (from INTERMEDIATE I.7)

INTERMEDIATE II.3: 2-Amino-4-hydroxy-N-(isopropylcarbamoylmethyl)benzamide (from INTERMEDIATE I.1 & benzyl deprotected analogue of commercially available 2-amino-4-benzyloxy-N-(isopropylcarbamoylmethyl)benzamide)

INTERMEDIATE II.4: 2-Amino-5-bromo-N-(isopropylcarbamoylmethyl)benzamide (from INTERMEDIATE I.1 & 2-amino-5-bromobenzoic acid)

INTERMEDIATE II.5: 2-Amino-4-chloro-N-(isopropylcarbamoylmethyl)benzamide (from INTERMEDIATE I.1 & 2-amino-4-chlorobenzoic acid)

INTERMEDIATE II.6: 2-Amino-N-(tert-butylcarbamoylmethyl)-5-hydroxybenzamide (from INTERMEDIATE I.5)

INTERMEDIATE II.7: 2-Amino-5-hydroxy-N-phenylcarbamoylmethylbenzamide (from INTERMEDIATE I.11)

INTERMEDIATE II.8: 2-Amino-N-(benzylcarbamoylmethyl)-5-hydroxybenzamide (from INTERMEDIATE I.2)

INTERMEDIATE II.9: 2-Amino-N-(tert-butylcarbamoylmethyl)-5-iodobenzamide (from (from INTERMEDIATE I.5 and 6-iodo-1H-benzo[d][1,3]oxazine-2,4-dione [For preparation see: Venuti, M. C. et al., *J. Med. Chem.*, 1988, 31, 2136-2145])

INTERMEDIATE II.10: 2-Amino-5-hydroxy-N-(isopropylcarbamoylmethyl)-4-methylbenzamide (from INTERMEDIATE I.1 & V.1)

INTERMEDIATE II.11: 2-Amino-4-chloro-5-hydroxy-N-(isopropylcarbamoylmethyl)benzamide (from INTERMEDIATE I.1 & V.2)

INTERMEDIATE II.12: 2-Amino-5-hydroxy-N-(isopropylcarbamoylmethyl)-4-methoxybenzamide (from INTERMEDIATE I.1 & VI.1)

INTERMEDIATE II.13: 2-Amino-5-hydroxy-N-(isobutylcarbamoylmethyl)benzamide (from INTERMEDIATE I.6)

INTERMEDIATE II.14: 2-Amino-N-cyclopentylcarbamoylmethyl-5-hydroxybenzamide (from INTERMEDIATE I.9)

INTERMEDIATE II.15: N-Allylcarbamoylmethyl-2-amino-5-hydroxybenzamide (from INTERMEDIATE I.10)

INTERMEDIATE II.16: 2-Amino-5-iodo-N-(isopropylcarbamoylmethyl)benzamide (from INTERMEDIATE I.1 & 2-amino-5-iodobenzoic acid)

INTERMEDIATE II.17: 2-Amino-5-iodo-N-(tert-butylcarbamoylmethyl)benzamide (from INTERMEDIATE I.5 & 2-amino-5-iodobenzoic acid)

INTERMEDIATE II.18: 2-Amino-5-hydroxy-N-[(2,2,2-trifluoroethylcarbamoyl)methyl]benzamide (from INTERMEDIATE I.12)

Procedure III

INTERMEDIATE III.1: Ethyl 3-chlorobenzimidate Hydrochloride

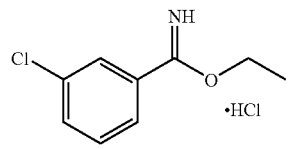

To a solution of 3-chlorobenzonitrile (50 g, 363 mmol) in anhydrous ethanol (500 mL), cooled to 0° C. in an ice bath, was bubbled HCl (g) through a gas dispersion tube for approximately 20 minutes until the solution was saturated. The resulting reaction mixture was stirred at room temperature for 16 h. Volatiles were removed in vacuo and the residue was triturated with anhydrous ether (~200 mL). The white solid was collected by filtration and dried in vacuo overnight to afford ethyl 3-chlorobenzimidate hydrochloride (INTERMEDIATE III.1) (80 g, 363 mmol, 100%) which was used directly without further purification.

Data for ethyl 3-chlorobenzimidate hydrochloride (INTERMEDIATE III.1): $^1$H NMR (300 MHz, DMSO): δ 12.0-11.8 (br s, 1H), 8.22-8.17 (t, 1H), 8.10-8.04 (dt, 1H), 7.90-7.85 (dt, 1H), 7.71-7.64 (t, 1H), 4.66-4.50 (q, 2H), 1.55-1.40 (t, 3H) ppm.

Similarly prepared were:

INTERMEDIATE III.2: Ethyl 3-methoxybenzimidate hydrochloride

INTERMEDIATE III.3: Ethyl 3-ethoxybenzimidate hydrochloride

INTERMEDIATE III.4: Ethyl 3,4-difluorobenzimidate hydrochloride

INTERMEDIATE III.5: Ethyl 3-chloro-4-fluorobenzimidate hydrochloride

INTERMEDIATE III.6: Ethyl 4-fluoro-3-methoxybenzimidate hydrochloride

INTERMEDIATE III.7: Ethyl 1H-indole-3-carboximidoate

INTERMEDIATE III.8: Ethyl 2-methylbenzimidate hydrochloride

INTERMEDIATE III.9: Ethyl 4-fluorobenzimidate hydrochloride

INTERMEDIATE III.10: Ethyl 3-methylbenzimidate hydrochloride

INTERMEDIATE III.11: Ethyl thiophene-2-carboximidoate

INTERMEDIATE III.12: Ethyl 3,5-dimethoxybenzimidate hydrochloride

INTERMEDIATE III.13: Ethyl 3-ethylbenzimidate hydrochloride

INTERMEDIATE III.14: Ethyl 2,3-dichlorobenzimidate hydrochloride

INTERMEDIATE III.15: Ethyl 5-chlorothiophene-2-carboximidoate

INTERMEDIATE III.16: Ethyl cyclohexanecarboximidoate

INTERMEDIATE III.17: Ethyl 3-hydroxybenzimidate hydrochloride

INTERMEDIATE III.18: Ethyl 3-fluorobenzimidate hydrochloride

Procedure IV

INTERMEDIATE IV.1: 2-[2-(3-Chloro-4-fluorophenyl)-6-hydroxy-4-oxo-4H-quinazolin-3-yl]-N-isopropylacetamide

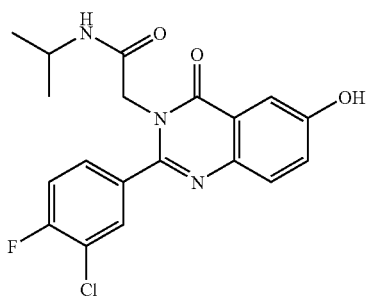

A mixture of 2-amino-5-hydroxy-N-(isopropylcarbamoylmethyl)benzamide (INTERMEDIATE II.1) (400 mg, 1.59 mmol) and ethyl 4-fluoro-3-chlorobenzimidate*HCl (INTERMEDIATE III.5) (1.14 g, 4.78 mmol) in ethanol (10 mL) was heated at reflux temperature for 1 h. The mixture was then cooled to room temperature and the resultant solid collected by filtration and washed with additional portions of cold ethanol (3×20 mL) to afford 2-[2-(3-chloro-4-fluorophenyl)-6-hydroxy-4-oxo-4H-quinazolin-3-yl]-N-isopropylacetamide (INTERMEDIATE IV.1) (380 mg, 0.97 mmol, 61%) as a white solid.

Data for 2-[2-(3-chloro-4-fluorophenyl)-6-hydroxy-4-oxo-4H-quinazolin-3-yl]-N-isopropylacetamide (INTERMEDIATE IV.1): MS (ESI) m/z: 390/392 ([M+H]$^+$)

Similarly prepared were:
INTERMEDIATE IV.2: N-tert-Butyl-2-[2-(3-chlorophenyl)-6-hydroxy-4-oxo-4H-quinazolin-3-yl]acetamide (from INTERMEDIATES II.6 & III.1)
INTERMEDIATE IV.3: N-tert-Butyl-2-[6-hydroxy-2-(3-methoxyphenyl)-4-oxo-4H-quinazolin-3-yl]acetamide (from INTERMEDIATES II.6 & III.2)
INTERMEDIATE IV.4: 2-[6-Hydroxy-2-(3-methoxyphenyl)-4-oxo-4H-quinazolin-3-yl]-N-isopropylacetamide (from INTERMEDIATES II.1 & III.2)
INTERMEDIATE IV.5: 2-[2-(3,4-Difluorophenyl)-6-hydroxy-4-oxo-4H-quinazolin-3-yl]-N-isopropylacetamide (from INTERMEDIATES II.1 & III.4)
INTERMEDIATE IV.6: N-Cyclopropylmethyl-2-(6-hydroxy-4-oxo-2-phenyl-4H-quinazolin-3-yl)acetamide (from INTERMEDIATE II.2 & commercially available ethyl benzimidate hydrochloride, Fluka USA)
INTERMEDIATE IV.7: 2-[2-(4-Fluoro-3-methoxyphenyl)-6-hydroxy-4-oxo-4H-quinazolin-3-yl]-N-isopropylacetamide (from INTERMEDIATES II.1 & III.6)
INTERMEDIATE IV.8: 2-[6-Hydroxy-2-(3-methoxyphenyl)-4-oxo-4H-quinazolin-3-yl]-N-phenylacetamide (from INTERMEDIATES II.7 & III.2)
INTERMEDIATE IV.9: N-Benzyl-2-[6-hydroxy-2-(3-methoxyphenyl)-4-oxo-4H-quinazolin-3-yl]acetamide (from INTERMEDIATES II.8 & III.2)
INTERMEDIATE IV.10: 2-[6-Bromo-2-(3-methoxyphenyl)-4-oxo-4H-quinazolin-3-yl]-N-isopropylacetamide (from INTERMEDIATES II.4 & III.2)
INTERMEDIATE IV.11: 2-[7-Chloro-2-(3-methoxyphenyl)-4-oxo-4H-quinazolin-3-yl]-N-isopropylacetamide (from INTERMEDIATES II.5 & III.2)
INTERMEDIATE IV.12: N-tert-Butyl-2-[2-(3-chlorophenyl)-6-iodo-4-oxo-4H-quinazolin-3-yl]acetamide (from INTERMEDIATES II.9 & III.1)
INTERMEDIATE IV.13: 2-[2-(3-Ethoxyphenyl)-6-hydroxy-4-oxo-4H-quinazolin-3-yl]-N-isopropylacetamide (from INTERMEDIATES II.1 & III.3)
INTERMEDIATE IV.14: 2-[2-(3-Chlorophenyl)-6-hydroxy-4-oxo-4H-quinazolin-3-yl]-N-isopropylacetamide (from INTERMEDIATES II.1 & III.1)
INTERMEDIATE IV.15: 2-[6-Hydroxy-7-methoxy-2-(3-methoxyphenyl)-4-oxo-4H-quinazolin-3-yl]-N-isopropylacetamide (from INTERMEDIATES II.12 & III.2)
INTERMEDIATE IV.16: 2-[6-Hydroxy-2-(3-methoxyphenyl)-7-methyl-4-oxo-4H-quinazolin-3-yl]-N-isopropylacetamide (from INTERMEDIATES II.10 & III.2)
INTERMEDIATE IV.17: 2-[7-Chloro-6-hydroxy-2-(3-methoxyphenyl)-4-oxo-4H-quinazolin-3-yl]-N-isopropylacetamide (from INTERMEDIATES II.11 & III.2)
INTERMEDIATE IV.18: 2-[7-Hydroxy-2-(3-methoxyphenyl)-4-oxo-4H-quinazolin-3-yl]-N-isopropylacetamide (from INTERMEDIATES II.3 & III.2)
INTERMEDIATE IV.19: N-Cyclopropylmethyl-2-[6-hydroxy-2-(3-methoxyphenyl)-4-oxo-4H-quinazolin-3-yl]acetamide (from INTERMEDIATES II.2 & III.2)
INTERMEDIATE IV.20: 2-[6-Hydroxy-2-(3-methoxyphenyl)-4-oxo-4H-quinazolin-3-yl]-N-isobutylacetamide (from INTERMEDIATES II.13 & III.2)
INTERMEDIATE IV.21: N-Cyclopentyl-2-(6-hydroxy-4-oxo-2-phenyl-4H-quinazolin-3-yl)acetamide (from INTERMEDIATE II.14 & commercially available ethyl benzimidate hydrochloride, Fluka USA)
INTERMEDIATE IV.22: N-Allyl-2-(6-hydroxy-4-oxo-2-phenyl-4H-quinazolin-3-yl)acetamide (from INTERMEDIATE II.15 & commercially available ethyl benzimidate hydrochloride, Fluka USA)
INTERMEDIATE IV.23: 2-(6-Hydroxy-4-oxo-2-phenyl-4H-quinazolin-3-yl)-N-isobutylacetamide (from INTERMEDIATE II.13 & commercially available ethyl benzimidate hydrochloride, Fluka USA)
INTERMEDIATE IV.24: 2-[6-Iodo-2-(3-methoxyphenyl)-4-oxo-4H-quinazolin-3-yl]-N-isopropylacetamide (from INTERMEDIATES II.16 & III.2)
INTERMEDIATE IV.25: 2-[2-(4-Fluoro-3-methoxyphenyl)-6-hydroxy-4-oxo-4H-quinazolin-3-yl]-N-tert-butylacetamide (from INTERMEDIATES II.6 & III.6)
INTERMEDIATE IV.26: 2-[6-Iodo-2-(4-fluoro-3-methoxyphenyl)-4-oxo-4H-quinazolin-3-yl]-N-tert-butylacetamide (from INTERMEDIATES II.17 & III.6)
INTERMEDIATE IV.27: 2-[6-Hydroxy-2-(3-methoxyphenyl)-4-oxo-4H-quinazolin-3-yl]-N-(2,2,2-trifluoroethyl)acetamide (from INTERMEDIATES II.18 & III.2)

Procedure V

INTERMEDIATE V.1:
2-Amino-5-hydroxy-4-methylbenzoic acid

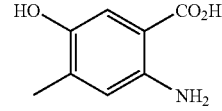

a) 1-Methoxy-2-methyl-4-nitrobenzene

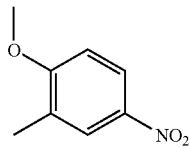

To a solution of 2-methyl-4-nitrophenol (10.2 g, 67 mmol) in acetonitrile (250 mL) was added potassium carbonate (27.6 g, 200 mmol) and methyl iodide (4.1 mL, 66 mmol). The mixture was stirred at 80° C. for 12 h. After cooling to room temperature, the solid was removed by filtration and the filtrate was evaporated under reduced pressure. The resulting oil was dissolved in dichloromethane (250 mL). The solution was washed with 2N NaOH (aq.) (200 mL), brine (100 mL), dried ($Na_2SO_4$), filtered and evaporated to yield 1-methoxy-2-methyl-4-nitrobenzene (9.5 g, 57 mmol, 85%).

Data for 1-methoxy-2-methyl-4-nitrobenzene: $^1$H NMR (400 MHz, $CDCl_3$): δ 8.12 (dd, 1H), 8.04 (d, 1H), 6.86 (d, 1H), 3.94 (s, 3H), 2.27 (s, 3H) ppm.

b) 4-Methoxy-3-methyl-phenylamine

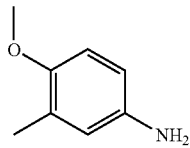

10% Palladium on carbon (10% Pd/C) (1.5 g) was added to a solution of 1-methoxy-2-methyl-4-nitrobenzene (9.5 g, 57 mmol) in methanol (100 mL). The mixture was stirred under a hydrogen atmosphere (1 atm.) at room temperature for 16 h. The mixture was filtered through a pad of CELITE™ and the filtrate was evaporated in vacuo to yield 4-methoxy-3-methylphenylamine (8.0 g, 57 mmol, 100%).

Data for 4-methoxy-3-methylphenylamine: $^1$H NMR (400 MHz, $CDCl_3$): δ 6.67 (d, 1H), 6.54 (dd, 1H), 6.50 (d, 1H), 3.77 (s, 3H), 3.29 (br s, 2H, amine N$\underline{H}_2$), 2.18 (s, 3H) ppm; MS (ESI) m/z: 138 ([M+H]$^+$).

c) 2-Hydroxyimino-N-(4-methoxy-3-methylphenyl) acetamide

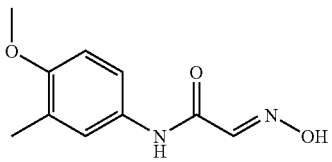

Chloral hydrate (11.5 g, 70 mmol) and anhydrous sodium sulfate (60 g, 422 mmol) were added to vigorously stirred water (300 mL). A slurry prepared by mixing hydroxylamine hydrochloride (23.0 g, 331 mmol) and 4-methoxy-3-methylphenylamine (10.0 g, 73 mmol) with aqueous hydrochloric acid (2.4 M, 250 mL) was added to the above mixture. The resulting mixture was refluxed for 20 min and then allowed to stand at room temperature for 16 h. A precipitate formed and was collected by filtration. The solid was washed with water and dried to yield 2-hydroxyimino-N-(4-methoxy-3-methylphenyl)acetamide (6.7 g, 32 mmol, 44%)

Data for 2-hydroxyimino-N-(4-methoxy-3-methylphenyl) acetamide: MS (ESI) m/z: 209 ([M+H]$^+$).

d) 5-Methoxy-6-methyl-1H-indole-2,3-dione

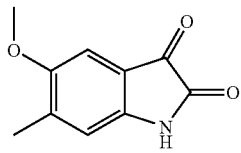

2-Hydroxyimino-N-(4-methoxy-3-methylphenyl)acetamide (0.5 g, 2.4 mmol) was added portionwise to concentrated methanesulfonic acid (1.5 mL). The 2-hydroxyimino-N-(4-methoxy-3-methylphenyl)acetamide was added over a period of 45 min in order to keep the reaction temperature between 65 to 70° C. After addition, the mixture was stirred for 10 min and then poured onto ice (10 g). The resulting aqueous solution was extracted with ethyl acetate (3×50 mL). Combined organic layers were dried ($Na_2SO_4$), filtered and concentrated in vacuo. The crude product was purified by column chromatography on silica gel with petroleum ether: ethyl acetate (20:1, v/v) as eluent to afford 5-methoxy-6-methyl-1H-indole-2,3-dione (350 mg, 1.8 mmol, 77%).

Data for 5-methoxy-6-methyl-1H-indole-2,3-dione: $^1$H NMR (400 MHz, $CDCl_3$): δ 7.62 (br. S, 1H, amide N$\underline{H}$), 7.04 (s, 1H), 6.72 (s, 1H), 3.82 (s, 3H), 2.29 (s, 3H) ppm.

e) 2-amino-5-methoxy-4-methylbenzoic acid

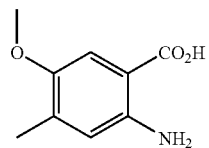

10% Hydrogen peroxide ($H_2O_2$) (80 mL) was added dropwise to a stirring solution of 5-methoxy-6-methyl-1H-indole-2,3-dione (4.7 g, 24.6 mmol) in 3N NaOH (aq.) (100 mL). The $H_2O_2$ solution was added over a period of 1.5 h in order to keep the temperature below 35° C. The solution was then acidified to pH 4 with 2.5M sulfuric acid. A precipitate formed and was collected by filtration. The solid was washed with water and dried to give 2-amino-5-methoxy-4-methylbenzoic acid (2.7 g, 14.9 mmol, 61%).

Data for 2-amino-5-methoxy-4-methylbenzoic acid: $^1$H NMR (400 MHz, $CD_3OD$): δ 7.40 (s, 1H), 7.00 (s, 1H) 3.80 (s, 3H) 2.19 (s, 3H) ppm; MS (ESI) m/z: 182 ([M+H]$^+$)

f) 2-Amino-5-hydroxy-4-methylbenzoic acid

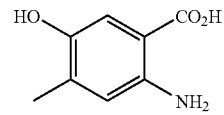

2-Amino-5-methoxy-4-methylbenzoic acid (2.7 g, 14.9 mmol, 61%) and aqueous hydriodic acid (40%, 80 mL) were heated at reflux for 36 h. The aqueous was evaporated under vacuum and the residue washed with ether to yield 2-amino-5-hydroxy-4-methylbenzoic acid (INTERMEDIATE V.1) (2.5 g, 14.9 mmol 100%)

Data for 2-amino-5-hydroxy-4-methylbenzoic acid (INTERMEDIATE V.1): $^1$H NMR (400 MHz, CD$_3$OD): δ 7.43 (s, 1H), 6.97 (s, 1H) 2.23 (s, 3H) ppm; MS (ESI) m/z: 168 ([M+H]$^+$).

Similarly prepared was:

INTERMEDIATE V.2:
2-Amino-4-chloro-5-hydroxybenzoic acid

Procedure VI

INTERMEDIATE VI.1:
2-Amino-5-hydroxy-4-methoxybenzoic Acid

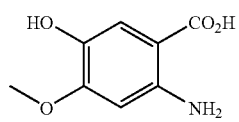

To a solution of 3-hydroxy-4-methoxy-6-nitrobenzoic acid (*Journal of Natural Product*, 1986, 49 (3), 445-448) (10.0 g, 46.9 mmol) in methanol (150 mL) was added 10% Pd/C (0.1 eq.). The reaction was stirred under a hydrogen atmosphere (1 atm.) at room temperature for 5 h. The solution was filtered and the filtrate was evaporated to afford 2-amino-5-hydroxy-4-methoxybenzoic acid (INTERMEDIATE V1.1) (7.0 g, 38.3 mmol, 82%).

Data for 2-amino-5-hydroxy-4-methoxybenzoic acid (INTERMEDIATE V1.1): MS (ESI) m/z: 184 ([M+H]$^+$).

Procedure VII

INTERMEDIATE VII.1: 2-Amino-N-(isopropylcarbamoylmethyl)-5-(3-piperidin-1-ylpropoxy)benzamide

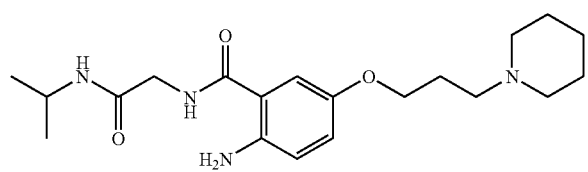

a) 2-Acetylamino-5-(3-hydroxypropoxy)benzoic acid methyl ester

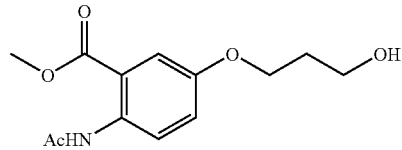

A mixture of 2-acetylamino-5-hydroxybenzoic acid methyl ester (2.0 g, 9.6 mmol), 3-bromopropan-1-ol (1.04 mL, 11.5 mmol) and K$_2$CO$_3$ (6.6 g, 47.8 mmol) in acetonitrile (50 mL) was heated to reflux temperature for 4.5 h. The mixture was cooled, filtered through a pad of CELITE™ and concentrated in vacuo. The crude residue was purified by chromatography on silica gel with ethyl acetate:hexane (2:1, v/v) as eluent. This afforded 2-acetylamino-5-(3-hydroxypropoxy)benzoic acid methyl ester (992 mg, 8.8 mmol, 92%)

Data for 2-acetylamino-5-(3-hydroxypropoxy)benzoic acid methyl ester: $^1$H NMR (300 MHz, d$^6$-DMSO): δ 10.2 (br s, 1H), 7.95 (d, 1H), 7.35 (d, 1H), 7.20 (dd, 1H), 4.05 (t, 2H), 3.80 (s, 3H), 3.55 (t, 2H), 2.05 (s, 3H), 1.82 (m, 2H) ppm.

b) 2-Acetylamino-5-(3-methanesulfonyloxypropoxy) benzoic acid methyl ester

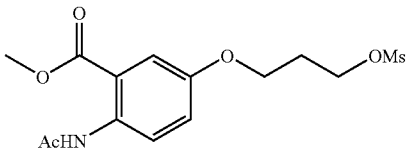

To a solution of 2-acetylamino-5-(3-hydroxypropoxy)benzoic acid methyl ester (689 mg, 2.6 mmol) in dichloromethane (25 mL) cooled to 0° C. were added methanesulfonyl chloride (1 mL, 12.9 mmol) and triethylamine (3.6 mL, 25.8 mmol). The mixture was warmed to room temperature and stirred for 2.5 h. The mixture was diluted with ethyl acetate (100 mL) and washed with 1 N HCl (aq.) (1×50 mL), sat. NaHCO$_3$ (aq.) (1×50 mL) and brine (1×50 mL). The organic layer was dried (MgSO$_4$), filtered and concentrated in vacuo. Crude 2-acetylamino-5-(3-methanesulfonyloxypropoxy)benzoic acid methyl ester thus obtained was used without further purification in the next step.

c) 2-Acetylamino-5-(3-piperidin-1-ylpropoxy)benzoic acid methyl ester

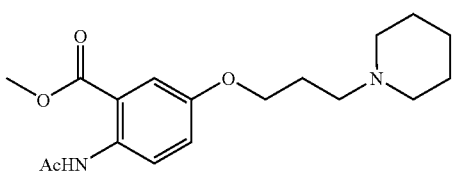

A mixture of the crude 2-acetylamino-5-(3-methanesulfonyloxypropoxy)benzoic acid methyl ester, piperidine (1.28 mL, 12.9 mmol) and K$_2$CO$_3$ (1.07 g, 7.7 mmol) in acetonitrile (12 mL) was heated at reflux temperature for 16 h. This reaction mixture was concentrated in vacuo and the crude residue partitioned between dichloromethane and water. The aqueous was extracted with dichloromethane (3×50 mL) and the combined organics washed with brine (1×50 mL), dried (MgSO$_4$) and concentrated in vacuo. The residue was purified by chromatography on silica gel with dichloromethane:methanol:NH$_4$OH (aq.) (180:19:1, v/v) as eluent to provide 2-acetylamino-5-(3-piperidin-1-ylpropoxy)benzoic acid methyl ester (526 mg, 1.6 mmol, 61% from 2-acetylamino-5-(3-hydroxypropoxy)benzoic acid methyl ester).

Data for 2-acetylamino-5-(3-piperidin-1-ylpropoxy)benzoic acid methyl ester: $^1$H NMR (300 MHz, CDCl$_3$): δ 10.77 (br s, 1H), 8.60 (d, 1H), 7.50 (d, 1H), 7.11 (dd, 1H), 4.00 (t, 2H), 3.92 (s, 3H), 2.48 (t, 2H), 2.41 (br m, 4H), 2.21 (s, 3H), 1.98 (m, 2H), 1.73-1.4 (m, 8H) ppm.

d) 2-Amino-5-(3-piperidin-1-ylpropoxy)benzoic acid

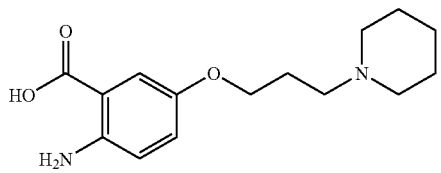

2-Acetylamino-5-(3-piperidin-1-ylpropoxy)benzoic acid methyl ester (1.34 g, 4.0 mmol) was treated with 6N HCl (aq.) (20 mL) and heated at reflux temperature for 8 h. The mixture was then cooled and concentrated in vacuo to afford 2-amino-5-(3-piperidin-1-ylpropoxy)benzoic acid dihydrochloride (1.4 g, 4.0 mmol, 100%).

Data for 2-amino-5-(3-piperidin-1-ylpropoxy)benzoic acid dihydrochloride: $^1$H NMR (300 MHz, D$_2$O): δ 7.69 (d, 1H), 7.43 (d, 1H), 7.28 (dd, 1H), 4.20 (t, 2H), 3.56 (br d, 2H), 3.30 (apparent t, 2H), 2.94 (td, 2H), 2.23 (m, 2H), 1.94 (m, 2H), 1.85-1.6 (m, 3H), 1.55-1.4 (m, 1H) ppm; MS (ESI) m/z: 279 ([M+H]$^+$).

e) 2-Amino-N-(isopropylcarbamoylmethyl)-5-(3-piperidin-1-ylpropoxy)benzamide

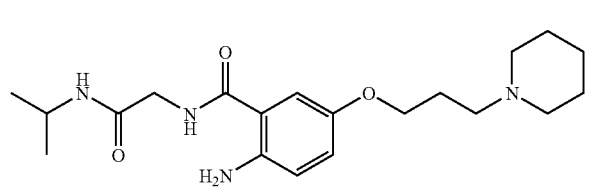

A mixture of 2-amino-5-(3-piperidin-1-ylpropoxy)benzoic acid dihydrochloride (1.3 g, 3.7 mmol), 2-amino-N-isopropylacetamide*HCl (INTERMEDIATE I.1) (557 mg, 3.7 mmol) and triethylamine (2.1 mL, 14.8 mmol) in DMF (20 mL) was stirred at room temperature for 10 min. EDC (851 mg, 4.4 mmol) and HOBt (600 mg, 4.4 mmol) were added and stirring continued at room temperature for 16 h. The mixture was partitioned between ethyl acetate (100 mL) and 2N Na$_2$CO$_3$ (aq.) (100 mL) and the aqueous extracted with additional ethyl acetate (2×100 mL). The combined organics were washed with brine (1×100 mL), dried (MgSO$_4$), filtered and concentrated in vacuo. The crude residue was purified by chromatography on silica gel with dichloromethane:methanol: NH$_4$OH (aq.) (160:39:1, v/v) as eluent to provide 2-amino-N-(isopropylcarbamoylmethyl)-5-(3-piperidin-1-ylpropoxy)benzamide (INTERMEDIATE V1.1) (1.4 g, 3.7 mmol, 100%).

Data for 2-amino-N-(isopropylcarbamoylmethyl)-5-(3-piperidin-1-ylpropoxy)benzamide (INTERMEDIATE VII.1): MS (ESI) m/z: 377 ([M+H]$^+$).

Similarly prepared were:

INTERMEDIATE VII.2: 2-Amino-N-(isopropylcarbamoylmethyl)-5-(3-morpholin-4-ylpropoxy)benzamide (from INTERMEDIATE I.1)

INTERMEDIATE VII.3: 2-Amino-N-cyclopropylcarbamoylmethyl-5-(3-piperidin-1-ylpropoxy)benzamide (from INTERMEDIATE I.8)

INTERMEDIATE VII.4: 2-Amino-N-(isopropylcarbamoylmethyl)-5-[3-(4-methylpiperazin-1-yl)propoxy]benzamide (from INTERMEDIATE I.1)

INTERMEDIATE VII.5: 2-Amino-N-cyclopropylcarbamoylmethyl-5-(3-morpholin-4-ylpropoxy)benzamide (from INTERMEDIATE I.8)

INTERMEDIATE VII.6: 2-Amino-N-[(cyclopropylmethylcarbamoyl)methyl]-5-(3-morpholin-1-ylpropoxy)benzamide (from INTERMEDIATE I.7)

Procedure VIII

INTERMEDIATE VIII.1: 2-Amino-5-[(S)-(+)-3-hydroxy-2-methylpropoxy]-N-(isopropylcarbamoylmethyl)benzamide

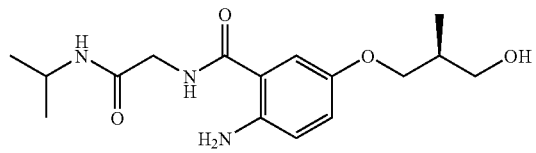

a) 2-Amino-5-[(S)-(+)-3-hydroxy-2-methylpropoxy]benzoic acid

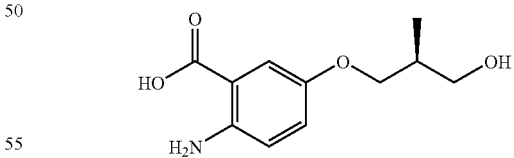

2-Acetylamino-5-[(S)-(+)-3-hydroxy-2-methylpropoxy]benzoic acid methyl ester (1.00 g, 3.6 mmol) prepared as in Procedure VII (Step a) was dissolved in 6 N HCl (aq.) (10 mL) and dioxane (5 mL) and heated at reflux temperature for 8 h. The mixture was then cooled and concentrated in vacuo giving 2-amino-5-[(S)-(+)-3-hydroxy-2-methylpropoxy]benzoic acid (936 mg, 3.6 mmol, 100%) as the hydrochloride salt.

Data for 2-amino-5-[(S)-(+)-3-hydroxy-2-methylpropoxy]benzoic acid hydrochloride: $^1$H NMR (300 MHz, D$_2$O): δ 7.39 (d, 1H), 7.22 (d, 1H), 7.18 (dd, 1H), 3.95 (dd, 1H), 3.79 (dd, 1H), 3.40 (m, 2H), 1.96 (m, 1H), 0.95 (d, 3H) ppm; MS (ESI), m/z: 226 ([M+H]$^+$).

b) 2-Amino-5-[(S)-(+)-3-hydroxy-2-methylpropoxy]-N-(isopropylcarbamoylmethyl)benzamide

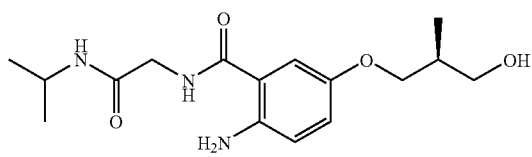

A mixture of 2-amino-5-[(S)-(+)-3-hydroxy-2-methylpropoxy]benzoic acid hydrochloride (200 mg, 0.76 mmol), 2-amino-N-isopropylacetamide*HCl (INTERMEDIATE I.1) (105 mg, 0.70 mmol) and triethylamine (0.23 mL, 1.68 mmol) in DMF (5 mL) was stirred at room temperature for 5 min. EDC (176 mg, 0.92 mmol) and HOBt (124 mg, 0.92 mmol) were added and stirring continued at room temperature for 16 h. The mixture was partitioned between ethyl acetate and sat. NaHCO$_3$ (aq.) and the aqueous extracted with additional ethyl acetate. The combined organics were washed with brine, dried (MgSO$_4$), filtered and concentrated in vacuo. The crude 2-amino-5-[(S)-(+)-3-hydroxy-2-methylpropoxy]-N-(isopropylcarbamoylmethyl)benzamide (INTERMEDIATE VIII.1) was used directly in the next reaction.

Similarly prepared were:

INTERMEDIATE VIII.2: 2-Amino-N-[(cyclopropylmethylcarbamoyl)methyl]-5-[(S)-(+)-3-hydroxy-2-methylpropoxy]benzamide (from INTERMEDIATE I.7)

INTERMEDIATE VIII.3: 2-Amino-5-(3-hydroxypropoxy)-N-(isopropylcarbamoylmethyl)benzamide (from 2-acetylamino-5-(3-hydroxypropoxy)benzoic acid methyl ester & INTERMEDIATE I.1)

INTERMEDIATE VIII.4: 2-Amino-N-ethylcarbamoylmethyl-5-[(S)-(+)-3-hydroxy-2-methylpropoxy]benzamide (from INTERMEDIATE 1.3)

INTERMEDIATE VIII.5: 2-Amino-5-[(S)-(+)-3-hydroxy-2-methylpropoxy]-N-propylcarbamoylmethylbenzamide (from INTERMEDIATE I.4)

INTERMEDIATE VIII.6: 2-Amino-N-[(cyclopropylmethylcarbamoyl)methyl]-5-(3-hydroxypropoxy)benzamide (from 2-acetylamino-5-(3-hydroxypropoxy)benzoic acid methyl ester & INTERMEDIATE 1.7)

Procedure IX

INTERMEDIATE IX.1: N-(4-Methoxybenzyl)-3-piperidin-1-ylpropan-1-amine

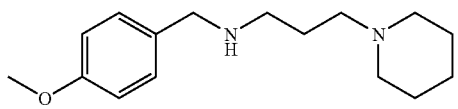

a) 4-Methoxy-N-(3-piperidin-1-ylpropyl)benzamide

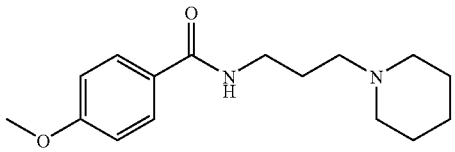

To a solution of N-3-aminopropylpiperidine (1.4 g, 10 mmol) in dichloromethane (20 mL) was added DIEA (1.9 mL, 11 mmol) followed by slow addition of 4-methoxy benzoyl chloride (1.9 g, 11 mmol). The reaction mixture was stirred at room temperature for 18 h. The solution was washed with 1 N KOH (aq.) (1×20 mL) and brine (1×20 mL). The organic phase was dried (K$_2$CO$_3$) and concentrated in vacuo to afford 4-methoxy-N-(3-piperidin-1-ylpropyl)benzamide (1.9 g, 6.9 mmol, 69%) as an oil.

Data for 4-methoxy-N-(3-piperidin-1-ylpropyl)benzamide: MS (ESI) m/z: 277 ([M+H]$^+$).

b) N-(4-Methoxybenzyl)-3-piperidin-1-ylpropan-1-amine

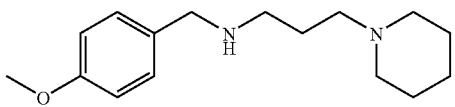

To a solution of 4-methoxy-N-(3-piperidin-1-ylpropyl)benzamide (1.9 g, 6.9 mmol) in THF (15 mL) was added borane*THF (1M in THF, 10 mL, 10 mmol) and the reaction mixture heated at reflux temperature for 18 h. The solution was cooled to room temperature and quenched with 4N HCl/dioxane (2 mL). The product mixture was washed with diethyl ether (2×50 mL) and basified with 40% (w/w) KOH (aq.). The aqueous layer was extracted with dichloromethane (3×50 mL) and the organic phase dried (Na$_2$SO$_4$) and concentrated in vacuo. The resultant oil was purified by chromatography on silica gel with methanol:dichloromethane (1:9, v/v) as eluent to afford N-(4-methoxybenzyl)-3-piperidin-1-ylpropan-1-amine (INTERMEDIATE IX.1) (400 mg, 1.5 mmol, 22%).

Data for N-(4-methoxybenzyl)-3-piperidin-1-ylpropan-1-amine (INTERMEDIATE IX.1): MS (ESI) m/z: 263 ([M+H]$^+$).

Procedure X

INTERMEDIATE X.1: 2-Amino-N-(isopropylcarbamoylmethyl)-5-[methyl-(3-piperidin-1-ylpropyl)amino]benzamide

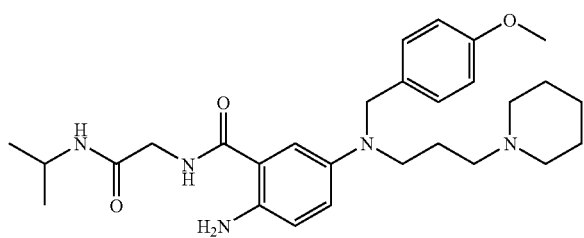

a) 5-Fluoro-2-nitrobenzoic acid

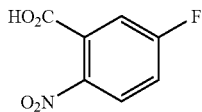

To a solution of 3-fluorobenzoic acid (7.9 g, 56 mmol) in conc. sulphuric acid (50 mL) cooled to 0° C. was added fuming nitric acid (4.7 g, 67 mmol) dropwise. After the addition the solution was warmed to room temperature and stirring continued for 1 h. The solution was poured into water (750 mL) and extracted with ethyl acetate (3×100 mL). The combined extracts were dried (MgSO$_4$) and concentrated in vacuo to yield 5-fluoro-2-nitrobenzoic acid as a pale yellow solid (9.6 g, 52 mmol, 93%).

Data for 5-fluoro-2-nitrobenzoic acid: $^1$H NMR (300 MHz, d$^6$-DMSO): δ 7.66 (m, 1H), 7.74 (m, 1H), 8.17 (m, 1H) ppm.

b) 5-Fluoro-N-(isopropylcarbamoylmethyl)-2-nitrobenzamide

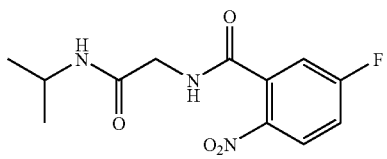

To a solution of 5-fluoro-2-nitrobenzoic acid (2.3 g, 12.4 mmol) in dichloromethane (20 mL) was added oxalyl chloride (3.2 g, 2.2 mL, 24.8 mmol) dropwise. After 1 h the solution was concentrated to dryness. 2-Amino-N-isopropylacetamide (INTERMEDIATE I.1) (0.30 g, 2.6 mmol) was dissolved in dichloromethane (20 mL) and diisopropylethylamine (DIEA) (6.8 mL, 38.9 mmol) added. The acid chloride in dichloromethane (10 mL) was added dropwise and the reaction mixture stirred at room temperature for 18 h. The reaction mixture was concentrated in vacuo, the residue dissolved in dichloromethane and washed with 1 N NaOH (aq.), 1 N HCl (aq.) and brine. The organic layers were dried (MgSO$_4$) and concentrated in vacuo to yield 5-fluoro-N-(isopropylcarbamoylmethyl)-2-nitrobenzamide (2.7 g, 9.5 mmol, 81%) as a yellow solid.

Data for 5-fluoro-N-(isopropylcarbamoylmethyl)-2-nitrobenzamide: MS (ESI) m/z: 284 ([M+H]$^+$).

c) N-(Isopropylcarbamoylmethyl)-5-[methyl-[(4-methoxybenzyl)(3-piperidin-1-ylpropyl)amino]-2-nitrobenzamide

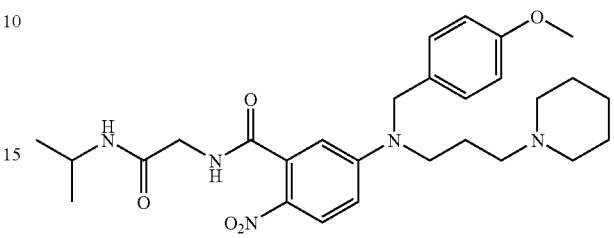

To a solution of 5-fluoro-N-(isopropylcarbamoylmethyl)-2-nitrobenzamide (0.28 g, 1.0 mmol) and N-(4-methoxybenzyl)-3-piperidin-1-ylpropan-1-amine (INTERMEDIATE IX.1) (0.40 g, 1.5 mmol) in acetonitrile (10 mL) was added K$_2$CO$_3$ (excess) and the reaction mixture stirred at room temperature for 36 h. The reaction mixture was filtered and concentrated in vacuo. The resulting oil was purified by chromatography on a silica gel with methanol:dichloromethane (1:9, v/v) as eluent to afford N-(isopropylcarbamoylmethyl)-5-[methyl[(4-methoxybenzyl)(3-piperidin-1-ylpropyl)amino]-2-nitrobenzamide (165 mg, 0.31 mmol, 31%) as a yellow foam.

Data for N-(isopropylcarbamoylmethyl)-5-[methyl[(4-methoxybenzyl)(3-piperidin-1-ylpropyl)amino]-2-nitrobenzamide: MS (ESI) m/z: 526 ([M+H]$^+$)

d) 2-Amino-N-(isopropylcarbamoylmethyl)-5-[(4-methoxybenzyl)(3-piperidin-1-ylpropyl)amino]benzamide

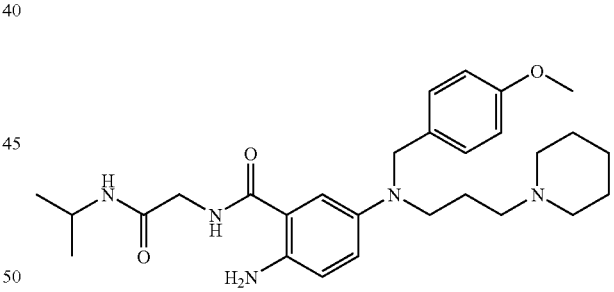

To a solution of N-(isopropylcarbamoylmethyl)-5-[methyl-[(4-methoxybenzyl)-(3-piperidin-1-ylpropyl)amino]-2-nitrobenzamide (0.16 g, 0.31 mmol) in ethanol (7 mL) was added tin chloride dihydrate (200 mg, 0.90 mmol). The mixture was heated at reflux temperature for 18 h. The mixture was concentrated in vacuo, dissolved in dichloromethane and washed with 1 N NaOH (aq.) and brine. The resulting oil was purified by chromatography on a silica gel with methanol:dichloromethane (1:9, v/v) as eluent to yield 2-amino-N-(isopropylcarbamoylmethyl)-5-[(4-methoxybenzyl)(3-piperidin-1-ylpropyl)amino]benzamide (INTERMEDIATE X.1) (0.08 g, 0.16 mmol, 52%) as a brown foam.

Data for 2-amino-N-(isopropylcarbamoylmethyl)-5-[(4-methoxybenzyl)(3-piperidin-1-ylpropyl)amino]benzamide (INTERMEDIATE X.1): MS (ESI) m/z: 496 ([M+H]$^+$)

Similarly prepared were:

INTERMEDIATE X.2: 2-Amino-N-(isopropylcarbamoylmethyl)-5-[methyl(3-piperidin-1-ylpropyl)amino]benzamide (from INTERMEDIATE 1.1 & methyl(3-piperidin-1-ylpropyl)amine)

INTERMEDIATE X.3: 2-Amino-N-(isopropylcarbamoylmethyl)-5-(3-piperidin-1-ylpropylsulfanyl)benzamide (from INTERMEDIATE 1.1 & 3-piperidin-1-ylpropane-1-thiol)

Procedure XI

INTERMEDIATE XI.1: Dimethyl-[3-(4,4,5,5-tetramethyl-[1,3,2]-dioxaborolan-2-yl)benzyl]amine

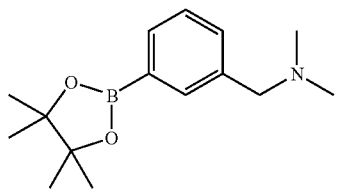

To a solution of 3-bromomethylphenyl boronic acid pinacol ester (Combi Block Inc., 297 mg, 1.0 mmol) in acetonitrile (5 mL) was added dimethylamine (2M solution in methanol, 2.0 mmol) followed by the addition of $K_2CO_3$ (691 mg, 5.0 mmol). The reaction mixture was stirred at room temperature for 16 h. Acetonitrile was removed under vacuum and the residue was partitioned between ethyl acetate and water. The organic layer was washed with saturated $NaHCO_3$, dried ($MgSO_4$), filtered and the filtrate concentrated in vacuo to give dimethyl-[3-(4,4,5,5-tetramethyl[1,3,2]dioxaborolan-2-yl)benzyl]amine (INTERMEDIATE XI.1) as a viscous oil (200 mg, 0.77 mmol, 77%).

Data for dimethyl-[3-(4,4,5,5-tetramethyl[1,3,2]dioxaborolan-2-yl)benzyl]amine (INTERMEDIATE XI.1): $^1$H NMR (300 MHz, $CD_3OD$): δ 7.70 (m, 2H), 7.30-7.45 (m, 2H), 3.50 (s, 2H), 2.28 (s, 6H), 1.36 (s, 12H) ppm; MS (ESI), m/z: 262 ([M+H]$^+$).

Similarly prepared was:

INTERMEDIATE XI.2: 1-[3-(4,4,5,5-Tetramethyl[1,3,2]dioxaborolan-2-yl)benzyl]piperidine Procedure XII INTERMEDIATE XII.1: (1S,3R)-3-Piperidin-1-ylcyclopentyl methanesulphonate

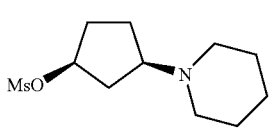

a) (1R,4S)-4-Piperidin-1-ylcyclopent-2-en-1-yl acetate

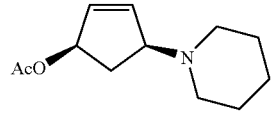

To a solution of (1R,4R)-4-[(methylsulphonyl)oxy]cyclopent-2-en-1-yl acetate (1.0 g, 4.54 mmol) (for preparation see: Borcherding, D. R., et al. *J. Med. Chem.* 1996, 39, 2615-2620) in DMF (10 mL) was added piperidine (2.25 mL, 22.7 mmol). The mixture was stirred at room temperature overnight. The mixture was diluted with water and extracted with ethyl acetate. The combined organic layers were dried ($MgSO_4$), filtered and concentrated in vacuo. The residue was purified by column chromatography on silica gel with dichloromethane:methanol (9:1, v/v) as eluent to afford (1R,4R)-4-[(methylsulphonyl)oxy]cyclopent-2-en-1-yl acetate (654 mg, 3.13 mmol, 69%).

Data for (1R,4R)-4-[(methylsulphonyl)oxy]cyclopent-2-en-1-yl acetate: $^1$H NMR (300 MHz, $CDCl_3$): δ 6.09 (ddd, 1H), 5.89 (ddd, 1H), 5.55 (ddd, 1H), 3.72 (ddd, 1H), 2.50-2.35 (m, 5H), 2.03 (s, 3H), 1.72 (dt, 1H), 1.58 (m, 4H), 1.41 (m, 2H) ppm; MS (ESI), m/z: 210 ([M+H]$^+$).

b) (1R,4S)-4-Piperidin-1-yl-cyclopent-2-en-1-ol

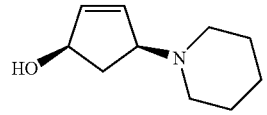

To a solution of (1R,4R)-4-[(methylsulphonyl)oxy]cyclopent-2-en-1yl acetate (164 mg, 0.78 mmol) in methanol (2.0 mL), was added $K_2CO_3$ (37 mg, 0.27 mmol). The mixture was stirred at room temperature overnight. The solvent was removed in vacuo and the residue was partitioned between ethyl acetate and water. The organic phase was dried ($MgSO_4$), filtered and concentrated in vacuo to yield (1R,4S)-4-piperidin-1-ylcyclopent-2-en-1ol (103 mg, 0.61 mmol, 78%) which was used in the next reaction without further purification.

Data for (1R,4S)-4-piperidin-1-ylcyclopent-2-en-1-ol: $^1$H NMR (300 MHz, $CDCl_3$): δ 5.92 (m, 2H), 4.62 (m, 1H), 3.81 (br s, 1H), 3.43 (m, 1H), 2.45-2.27 (m, 5H), 1.65-1.50 (m, 5H), 1.4 (m, 2H) ppm; MS (ESI) m/z: 168 ([M+H]$^+$).

c) (1S,3R)-3-Piperidin-1-ylcyclopentanol

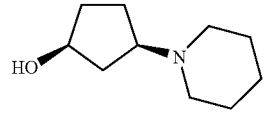

To a solution of (1R,4S)-4-piperidin-1-ylcyclopent-2-en-1-ol (50 mg, 0.30 mmol) in methanol (1 mL), was added a catalytic amount of platinum (IV) oxide ($PtO_2$). The mixture was stirred under a hydrogen atmosphere (1 atm.) for 4 h. The mixture was filtered and solvent evaporated in vacuo to afford (1S,3R)-3-piperidin-1-ylcyclopentanol (32 mg, 0.19 mmol, 63%). This was used in the next step without further purification.

Data for (1S,3R)-3-piperidin-1-ylcyclopentanol: MS (ESI) m/z: 170 ([M+H]$^+$).

d) (1S,3R)-3-Piperidin-1-ylcyclopentyl methanesulphonate

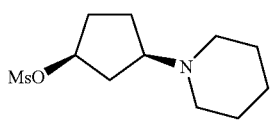

To a solution of 3-piperidin-1-yl-cyclopentanol (150 mg, 0.89 mmol) in dichloromethane (2.5 mL) at 0° C. were added methanesulphonyl chloride (206 µL, 2.66 mmol) and triethylamine (370 uL; 2.66 mmol). The mixture was warmed to room temperature and stirred for 3 h. The mixture was then diluted with ethyl acetate and washed with 1 N HCl (aq.), sat. NaHCO$_3$ (aq.) and brine. The organic layer was dried (MgSO$_4$), filtered and concentrated in vacuo. The crude (1S,3R)-3-piperidin-1-ylcyclopentyl methanesulphonate (INTERMEDIATE XII.1) (90 mg, 0.36 mmol, 41%) was used without further purification.

Data for (1S,3R)-3-Piperidin-1-ylcyclopentyl methanesulphonate: MS (ESI) m/z: 248 ([M+H]$^+$)

SYNTHESIS OF EXAMPLES ACCORDING TO THE INVENTION

Example 1a

N-isopropyl-2-[4-oxo-6-(3-piperidin-1-ylpropoxy)-2-quinolin-5-yl-4H-quinazolin-3-yl]acetamide

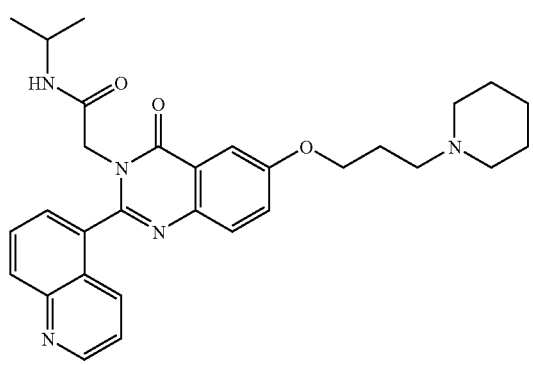

a) N-isopropyl-2-[4-oxo-6-(3-piperidin-1-ylpropoxy)-2-quinolin-5-yl-1,4-dihydro-2H-quinazolin-3-yl]acetamide

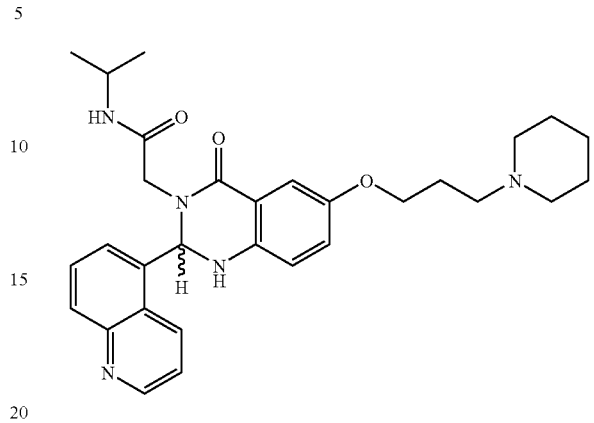

A solution of 2-amino-N-(isopropylcarbamoylmethyl)-5-(3-piperidin-1-ylpropoxy)benzamide (INTERMEDIATE VII.1) (50.5 mg, 0.13 mmol), 5-quinolinecarboxaldehyde (25 mg, 0.16 mmol) and acetic acid (glacial, 2 drops, cat.) in anhydrous ethanol (1.5 mL) was heated at 85° C. in a sealed vial for 19 h. The mixture was concentrated and the residue dissolved in chloroform (2 mL). MP-carbonate (Argonaut Technologies, loading 2.89 mmol/g, 170 mg, 0.49 mmol) and PS-TsNHNH$_2$ (Argonaut Technologies, loading 3.96 mmol/g, 125 mg, 0.50 mmol) resins were added to scavenge acid and unreacted aldehyde, respectively, and the resultant suspension was agitated for 20 h using an orbital shaker. The mixture was filtered and the resin was washed with chloroform (3×1 mL). The combined filtrates were used directly in Step b), and a sample was removed for MS analysis.

Data for N-isopropyl-2-[4-oxo-6-(3-piperidin-1-ylpropoxy)-2-quinolin-5-yl-1,4-dihydro-2H-quinazolin-3-yl]acetamide: MS (ESI) m/z: 516 ([M+H]$^+$), 1030 ([2M+H]$^+$), 1053 ([2M+Na]$^+$).

b) N-Isopropyl-2-[4-oxo-6-(3-piperidin-1-ylpropoxy)-2-quinolin-5-yl-4H-quinazolin-3-yl]acetamide

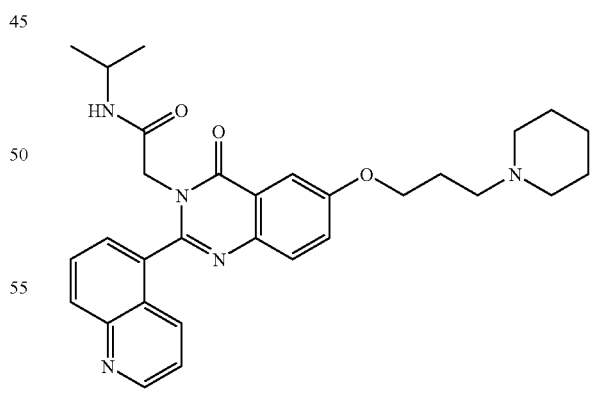

Manganese dioxide (55 mg, 0.63 mmol) was added to the chloroform solution produced in Step a). The resultant dark suspension was heated at 60° C. in a sealed vial for 2.5 h. The mixture was filtered through CELITE™ and the filtrate was concentrated in vacuo. The crude product was purified by preparative thin layer chromatography (500 µm plate) with methanol:dichloromethane:NH$_4$OH (aq.) (20:179:1, v/v) as eluent to afford N-isopropyl-2-[4-oxo-6-(3-piperidin-1-yl-propoxy)-2-quinolin-5-yl-4H-quinazolin-3-yl]acetamide (EXAMPLE 1a) (28 mg, 0.05 mmol, 40% from 2-amino-N-(isopropylcarbamoylmethyl)-5-(3-piperidin-1-ylpropoxy) benzamide) as an off-white solid.

Data for N-isopropyl-2-[4-oxo-6-(3-piperidin-1-ylpropoxy)-2-quinolin-5-yl-4H-quinazolin-3-yl]acetamide (EXAMPLE 1a): $^1$H NMR (300 MHz, CDCl$_3$): δ 8.98 (dd, 1H), 8.26 (d, 1H), 8.09 (d, 1H), 7.84-7.79 (m, 2H), 7.73 (d, 1H), 7.69 (d, 1H), 7.42 (ddd, 2H), 5.31 (d, 1H), 4.38 (ABq, 2H), 4.19-4.17 (m, 2H), 3.92 (septet, 1H), 2.55 (t, 2H), 2.48-2.42 (br m, 3H), 2.10-1.05 (t, 2H), 1.65-1.61 (m, 5H), 1.50-1.44 (m, 2H), 1.06 (d, 3H), 1.01 (d, 3H) ppm; MS (ESI) m/z: 514 ([M+H]$^+$), 1027 ([2M+H]$^+$), 1049 ([2M+Na]$^+$).

The following compounds (Examples 1b-1q) were prepared in a similar manner:

Example 1b

2-[2-(3-Isopropoxyphenyl)-4-oxo-6-(3-piperidin-1-ylpropoxy)-4H-quinazolin-3-yl]-N-isopropylacetamide, MS (ESI) m/z: 521 ([M+H]$^+$) (from INTERMEDIATE VII.1)

Example 1c

N-Isopropyl-2-[4-oxo-6-(3-piperidin-1-ylpropoxy)-2-(3-propoxyphenyl)-4H-quinazolin-3-ylacetamide, MS (ESI) m/z: 521 ([M+H]$^+$) (from INTERMEDIATE VII.1)

Example 1d

2-[2-(2-Fluoro-5-methoxyphenyl)-4-oxo-6-(3-piperidin-1-ylpropoxy)-4H-quinazolin-3-yl]-N-isopropylacetamide, MS (ESI) m/z: 511 ([M+H]$^+$) (from INTERMEDIATE VII.1)

Example 1e

N-Isopropyl-2-[4-oxo-6-(3-piperidin-1-ylpropoxy)-2-(3-trifluoromethylphenyl)-4H-quinazolin-3-yl]acetamide, MS (ESI) m/z: 531 ([M+H]$^+$) (from INTERMEDIATE VI.1)

Example 1f

N-Isopropyl-2-[4-oxo-6-(3-piperidin-1-ylpropoxy)-2-(3,4,5-trifluorophenyl)-4H-quinazolin-3-yl]acetamide, MS (ESI) m/z: 517 ([M+H]$^+$) (from INTERMEDIATE VII.1)

Example 1g

2-[2-(3-Iodophenyl)-4-oxo-6-(3-piperidin-1-ylpropoxy)-4H-quinazolin-3-yl]-N-isopropylacetamide, MS (ESI) m/z: 589/590 ([M+H]$^+$) (from INTERMEDIATE VII.1)

Example 1h

N-Isopropyl-2-[2-(6-methoxypyridin-2-yl)-4-oxo-6-(3-piperidin-1-ylpropoxy)-4H-quinazolin-3-yl]acetamide, MS (ESI) m/z: 494 ([M+H]$^+$) (from INTERMEDIATE VII.1)

Example 1i

2-[2-(3-Cyclopentyloxyphenyl)-4-oxo-6-(3-piperidin-1-ylpropoxy)-4H-quinazolin-3-yl]-N-isopropylacetamide, MS (ESI) m/z: 547 ([M+H]$^+$) (from INTERMEDIATE VII.1)

Example 1j

N-Isopropyl-2-[4-oxo-6-(3-piperidin-1-ylpropoxy)-2-pyrimidin-5-yl-4H-quinazolin-3-yl]acetamide, MS (ESI) m/z: 465 ([M+H]$^+$) (from INTERMEDIATE VII.1)

Example 1k

N-Isopropyl-2-[4-oxo-6-(3-piperidin-1-ylpropoxy)-2-(3-pyrrol-1-ylphenyl)-4H-quinazolin-3-yl]acetamide, MS (ESI) m/z: 528 ([M+H]$^+$) (from INTERMEDIATE VII.1)

Example 1l

3-[3-(Isopropylcarbamoylmethyl)-4-oxo-6-(3-piperidin-1-ylpropoxy)-3,4-dihydroquinazolin-2-yl]benzoic acid methyl ester, MS (ESI) m/z: 521 ([M+H]$^+$) (from INTERMEDIATE VII.1)

Example 1m

2-[2-(3-Dimethylaminophenyl)-4-oxo-6-(3-piperidin-1-ylpropoxy)-4H-quinazolin-3-yl]-N-isopropylacetamide, MS (ESI) m/z: 506 ([M+H]$^+$) (from INTERMEDIATE VII.1)

Example 1n

2-[2-(3-Cyanophenyl)-4-oxo-6-(3-piperidin-1-ylpropoxy)-4H-quinazolin-3-yl]-N-isopropylacetamide, MS (ESI) m/z: 488 ([M+H]$^+$) (from INTERMEDIATE VII.1)

Example 1o

2-[2-(3-Cyclobutoxyphenyl)-4-oxo-6-(3-piperidin-1-ylpropoxy)-4H-quinazolin-3-yl]-N-isopropylacetamide, MS (ESI) m/z: 533 ([M+H]$^+$) (from INTERMEDIATE VII.1)

Example 1p

N-Isopropyl-2-[4-oxo-6-(3-piperidin-1-ylpropoxy)-2-(3-trifluoromethoxyphenyl)-4H-quinazolin-3-yl]acetamide, MS (ESI) m/z: 547 ([M+H]$^+$) (from INTERMEDIATE VII.1)

Example 1q

2-[2-(1H-Indol-6-yl)-4-oxo-6-(3-piperidin-1-ylpropoxy)-4H-quinazolin-3-yl]-N-isopropylacetamide, MS (ESI) m/z: 502 ([M+H]$^+$) (from INTERMEDIATE VII.1)

Example 2a

2-[2-(3-Chloro-4-fluorophenyl)-4-oxo-6-(3-piperidin-1-ylpropoxy)-4H-quinazolin-3-yl]-N-isopropylacetamide hydrochloride

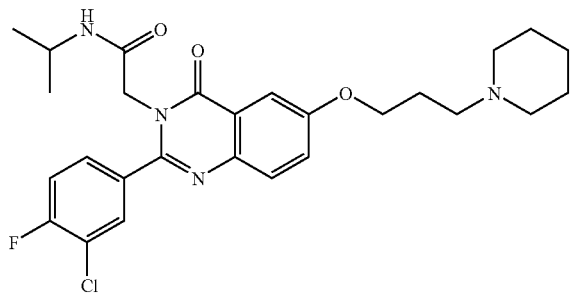

a) 2-[2-(3-Chloro-4-fluorophenyl)-6-(3-chloropropoxy)-4-oxo-4H-quinazolin-3-yl]-N-isopropylacetamide

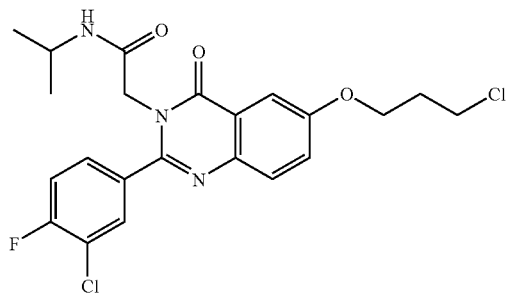

A mixture of 2-[2-(3-chloro-4-fluorophenyl)-6-hydroxy-4-oxo-4H-quinazolin-3-yl]-N-isopropylacetamide (INTERMEDIATE IV.1) (373 mg, 0.96 mmol), 3-bromo-1-chloropropane (0.28 mL, 2.87 mmol) and $K_2CO_3$ (662 mg, 4.80 mmol) in acetonitrile (5 mL) was heated at reflux temperature for 24 h. The mixture was cooled to room temperature and then poured into ice water (40 mL). The resultant white solid was collected by filtration and washed with additional portions of cold water (3×20 mL) followed by washing with cold diethyl ether (3×10 mL) and cold hexane (2×10 mL) to remove residual 3-bromo-1-chloropropane. In this way 2-[2-(3-chloro-4-fluorophenyl)-6-(3-chloropropoxy)-4-oxo-4H-quinazolin-3-yl]-N-isopropylacetamide (391 mg, 0.84 mmol, 87%) was obtained.

Data for 2-[2-(3-chloro-4-fluorophenyl)-6-(3-chloropropoxy)-4-oxo-4H-quinazolin-3-yl]-N-isopropylacetamide: MS (ESI) m/z: 466/468 ([M+H]$^+$)

b) 2-[2-(3-Chloro-4-fluoro-phenyl)-4-oxo-6-(3-Piperidin-1-yl-propoxy)-4H-quinazolin-3-yl]-N-isopropyl-acetamide hydrochloride

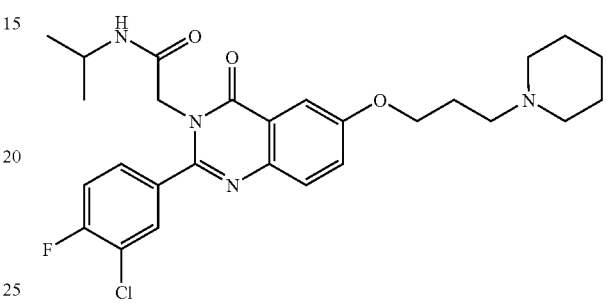

To a suspension of 2-[2-(3-chloro-4-fluorophenyl)-6-(3-chloropropoxy)-4-oxo-4H-quinazolin-3-yl]-N-isopropylacetamide (120 mg, 0.26 mmol) in acetonitrile (1 mL) was added $K_2CO_3$ (178 mg, 1.29 mmol), piperidine (0.76 mL, 0.77 mmol) and sodium iodide (20 mg, 0.13 mmol). The resultant mixture was heated to 80° C. in a tightly capped vial with stirring for 20 h. The mixture was then cooled to room temperature and poured into ice water (8 mL). The resultant white solid was collected by filtration and the filter cake was washed with cold diethyl ether (3×10 mL). The crude product was purified by chromatography on silica gel with methanol:dichloromethane (1:9, v/v) as eluent to afford 2-[2-(3-chloro-4-fluorophenyl)-4-oxo-6-(3-piperidin-1-ylpropoxy)-4H-quinazolin-3-yl]-N-isopropylacetamide (120 mg, 0.23 mmol, 91%). The HCl salt was prepared by treating the freebase with 5% HCl in ethanol (xs.) followed by removal of the ethanolic HCl in vacuo. The resultant HCl salt was redissolved in ethanol and the ethanol removed in vacuo (3×) to help remove residual HCl. The HCl salt thus obtained was then triturated with diethyl ether and collected by filtration affording 2-[2-(3-chloro-4-fluorophenyl)-4-oxo-6-(3-piperidin-1-ylpropoxy)-4H-quinazolin-3-yl]-N-isopropylacetamide hydrochloride (EXAMPLE 2a) as a white crystalline solid.

Data for 2-[2-(3-chloro-4-fluorophenyl)-4-oxo-6-(3-piperidin-1-ylpropoxy)-4H-quinazolin-3-yl]-N-isopropylacetamide hydrochloride (EXAMPLE 2a): $^1$H NMR (300 MHz, CD$_3$OD): δ 7.82-7.45 (m, 6H), 4.63 (s, 2H), 4.28 (t, 2H), 3.93 (septet, 1H), 3.63 (d, 2H), 3.36 (t, 2H), 3.01 (t, 2H), 2.34 (m, 2H), 2.02-1.29 (m, 8H), 1.11 (d, 6H) ppm; MS (ESI) m/z: 515/517 ([M+H]$^+$).

The following compounds (Examples 2b-2ac) were prepared in a similar manner:

Example 2b

N-tert-Butyl-2-[2-(3-methoxyphenyl)-4-oxo-6-(3-pyrrolidin-1-ylpropoxy)-4H-quinazolin-3-yl]acetamide, MS (ESI) m/z: 493 ([M+H]$^+$) (from INTERMEDIATE IV.3)

Example 2c

N-tert-Butyl-2-[2-(3-chlorophenyl)-4-oxo-6-(3-pyrrolidin-1-ylpropoxy)-4H-quinazolin-3-yl]acetamide, MS (ESI) m/z: 497/499 ([M+H]$^+$) (from INTERMEDIATE IV.2)

Example 2d

N-tert-Butyl-2-[2-(3-methoxyphenyl)-4-oxo-6-(3-piperidin-1-ylpropoxy)-4H-quinazolin-3-yl]acetamide, MS (ESI) m/z: 507 ([M+H]$^+$) (from INTERMEDIATE IV.3)

Example 2e

2-[2-(3,4-Difluorophenyl)-4-oxo-6-(3-piperidin-1-ylpropoxy)-4H-quinazolin-3-yl]-N-isopropylacetamide, MS (ESI) m/z: 499 ([M+H]$^+$) (from INTERMEDIATE IV.5)

Example 2f

N-tert-Butyl-2-[2-(3-chlorophenyl)-4-oxo-6-(3-piperidin-1-ylpropoxy)-4H-quinazolin-3-yl]acetamide, MS (ESI) m/z: 511/513 ([M+H]$^+$) (from INTERMEDIATE IV.2)

Example 2g

2-[2-(3-Ethoxyphenyl)-4-oxo-6-(3-piperidin-1-ylpropoxy)-4H-quinazolin-3-yl]-N-isopropylacetamide, MS (ESI) m/z: 507 ([M+H]$^+$) (from INTERMEDIATE IV.13)

Example 2h

N-Isopropyl-2-[2-(3-methoxyphenyl)-4-oxo-6-(3-piperidin-1-ylpropoxy)-4H-quinazolin-3-yl]acetamide, MS (ESI) m/z: 493 ([M+H]$^+$) (from INTERMEDIATE IV.4)

Example 2i

2-[2-(4-Fluoro-3-methoxyphenyl)-4-oxo-6-(3-piperidin-1-ylpropoxy)-4H-quinazolin-3-yl]-N-isopropylacetamide, MS (ESI) m/z: 511 ([M+H]$^+$) (from INTERMEDIATE IV.7)

Example 2j

N-tert-Butyl-2-[2-(3-chlorophenyl)-6-(3-dimethylaminopropoxy)-4-oxo-4H-quinazolin-3-yl]acetamide, MS (ESI) m/z: 471/473 ([M+H]$^+$) (from INTERMEDIATE IV.2)

Example 2k

N-tert-Butyl-2-[6-(3-dimethylaminopropoxy)-2-(3-methoxyphenyl)-4-oxo-4H-quinazolin-3-yl]acetamide, MS (ESI) m/z: 467 ([M+H]$^+$) (from INTERMEDIATE IV.3)

Example 2l

N-tert-Butyl-2-[6-(3-diethylaminopropoxy)-2-(3-methoxyphenyl)-4-oxo-4H-quinazolin-3-yl]acetamide, MS (ESI) m/z: 495 ([M+H]$^+$) (from INTERMEDIATE IV.3)

Example 2m

N-tert-Butyl-2-[2-(3-chlorophenyl)-6-(3-diethylaminopropoxy)-4-oxo-4H-quinazolin-3-yl]acetamide, MS (ESI) m/z: 499/501 ([M+H]$^+$) (from INTERMEDIATE IV.2)

Example 2n

2-{2-(3-Chlorophenyl)-6-[3-(4-hydroxypiperidin-1-yl)propoxy]-4-oxo-4H-quinazolin-3-yl}-N-isopropylacetamide, MS (ESI) m/z: 513/515 ([M+H]$^+$) (from INTERMEDIATE IV.14)

Example 2o

2-{2-(3-Chlorophenyl)-6-[3-(3-hydroxypiperidin-1-yl)propoxy]-4-oxo-4H-quinazolin-3-yl}-N-isopropylacetamide, MS (ESI) m/z: 513/515 ([M+H]$^+$) (from INTERMEDIATE IV.14

Example 2p

2-{2-(4-Fluoro-3-methoxyphenyl)-6-[3-(4-hydroxypiperidin-1-yl)propoxy]-4-oxo-4H-quinazolin-3-yl}-N-isopropylacetamide, MS (ESI) m/z: 527 ([M+H]$^+$) (from INTERMEDIATE IV.7)

Example 2q

2-{2-(3-Chloro-4-fluorophenyl)-6-[3-(4-hydroxypiperidin-1-yl)propoxy]-4-oxo-4H-quinazolin-3-yl}-N-isopropylacetamide, MS (ESI) m/z: 531/533 ([M+H]$^+$) (from INTERMEDIATE IV.1)

Example 2r

N-Isopropyl-2-[2-(3-methoxyphenyl)-4-oxo-6-(4-piperidin-1-ylbutoxy)-4H-quinazolin-3-yl]acetamide, MS (ESI) m/z: 507 ([M+H]$^+$) (from INTERMEDIATE IV.4)

Example 2s

N-Isopropyl-2-[2-(3-methoxyphenyl)-4-oxo-6-(2-piperidin-1-ylethoxy)-4H-quinazolin-3-yl]acetamide, MS (ESI) m/z: 479 ([M+H]$^+$) (from INTERMEDIATE IV.4)

Example 2t

2-[2-(3-Methoxyphenyl)-4-oxo-6-(3-piperidin-1-ylpropoxy)-4H-quinazolin-3-yl]-N-phenylacetamide, MS (ESI) m/z: 527 ([M+H]$^+$) (from INTERMEDIATE IV.8)

Example 2u

N-Benzyl-2-[2-(3-methoxyphenyl)-4-oxo-6-(3-piperidin-1-ylpropoxy)-4H-quinazolin-3-yl]acetamide, MS (ESI) m/z: 541 ([M+H]$^+$) (from INTERMEDIATE IV.9)

Example 2v

N-Isopropyl-2-[7-methoxy-2-(3-methoxyphenyl)-4-oxo-6-(3-piperidin-1-ylpropoxy)-4H-quinazolin-3-yl]acetamide, MS (ESI) m/z: 523 ([M+H]$^+$) (from INTERMEDIATE IV.15)

Example 2w

N-Isopropyl-2-[2-(3-methoxyphenyl)-7-methyl-4-oxo-6-(3-piperidin-1-ylpropoxy)-4H-quinazolin-3-yl]acetamide, MS (ESI) m/z: 507 ([M+H]$^+$) (from INTERMEDIATE IV.16)

Example 2x

2-[7-Chloro-2-(3-methoxyphenyl)-4-oxo-6-(3-piperidin-1-ylpropoxy)-4H-quinazolin-3-yl]-N-isopropylacetamide, MS (ESI) m/z: 527/529 ([M+H]$^+$) (from INTERMEDIATE IV.17)

Example 2y

N-tert-Butyl-2-{2-(3-chlorophenyl)-6-[3-(4-hydroxy-4-methylpiperidin-1-yl)propoxy]-4-oxo-4H-quinazolin-3-yl}acetamide, MS (ESI) m/z: 541 ([M+H]$^+$) (from INTERMEDIATE IV.2)

Example 2z

N-Isopropyl-2-{2-(3-methoxyphenyl)-6-[3-(4-methylpiperidin-1-yl)propoxy]-4-oxo-4H-quinazolin-3-yl}acetamide, MS (ESI) m/z: 507 ([M+H]$^+$) (from INTERMEDIATE IV.4)

Example 2aa

2-[6-[3-(4,4-Dimethylpiperidin-1-yl)propoxy]-2-(3-methoxyphenyl)-4-oxo-4H-quinazolin-3-yl]-N-isopropylacetamide, MS (ESI) m/z: 521 ([M+H]$^+$) (from INTERMEDIATE IV.4)

Example 2ab

2-[6-[3-(4-Hydroxy-4-methylpiperidin-1-yl)propoxy]-2-(3-methoxyphenyl)-4-oxo-4H-quinazolin-3-yl]-N-isopropylacetamide, MS (ESI) m/z: 523 ([M+H]$^+$) (from INTERMEDIATE IV.4)

Example 2ac

2-[2-(3-Methoxyphenyl)-4-oxo-6-(3-piperidin-1-ylpropoxy)-4H-quinazolin-3-yl]-N-(2,2,2-trifluoroethyl)acetamide, MS (ESI) m/z: 533 ([M+H]$^+$) (from INTERMEDIATES IV.27)

Example 3a

2-[2-(3-Chlorophenyl)-4-oxo-6-(3-piperidin-1-ylpropoxy)-4H-quinazolin-3-yl]-N-isopropylacetamide hydrochloride

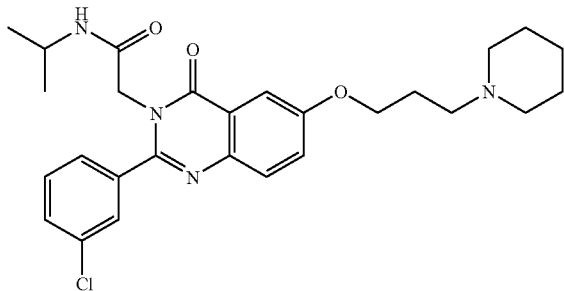

A mixture of 2-amino-N-(isopropylcarbamoylmethyl)-5-(3-piperidin-1-ylpropoxy)benzamide (INTERMEDIATE VII.1) (1.40 g, 3.72 mmol) and ethyl 3-chlorobenzimidate*HCl (INTERMEDIATE III.1) (2.46 g, 11.16 mmol) in anhydrous ethanol (20 mL) was heated to 80° C. in a sealed pressure tube for 16 h. This was then cooled and concentrated in vacuo. The crude residue was partitioned between dichloromethane:2-propanol (3:1 [v/v], 80 mL) and water (50 mL) and the aqueous extracted with additional dichloromethane:2-propanol (3:1 [v/v], 3×80 mL). The combined organics were dried (MgSO$_4$), filtered and concentrated in vacuo. The amber oil thus obtained was purified by chromatography on silica gel with dichloromethane:methanol:NH$_4$OH (aq.) (170:29:1, v/v) as eluent to afford a sticky light yellow solid (1.74 g). This was further purified by recrystallization from ethanol:hexane to afford a white solid (410 mg, 0.82 mmol, 22%). A second crop was obtained as follows: the filtrate was concentrated in vacuo and the crude oil partitioned between 1N HCl (aq.) (20 mL) and ethyl acetate (10 mL) and washed with additional ethyl acetate (10 mL). The aqueous phase was basified with 3N NaOH (aq.) to give a white precipitate which was collected by filtration and washed with cold water. The residue was recrystallized from 90% ethanol (aq.) giving additional product as a white solid (254 mg, 0.52 mmol, 14%). Both batches were combined to afford 2-[2-(3-chlorophenyl)-4-oxo-6-(3-piperidin-1-ylpropoxy)-4H-quinazolin-3-yl]-N-isopropylacetamide (664 mg, 1.34 mmol, 36%). 2-[2-(3-Chlorophenyl)-4-oxo-6-(3-piperidin-1-ylpropoxy)-4H-quinazolin-3-yl]-N-isopropylacetamide was treated with 4N HCl in methanol (4 mL, prepared by the addition of AcCl (4 mmol) to methanol (10 mL) dropwise at 0° C.) and concentrated in vacuo. The resultant crystalline white solid was triturated with cold diethyl ether, collected by filtration and dried in vacuo giving 2-[2-(3-chlorophenyl)-4-oxo-6-(3-piperidin-1-ylpropoxy)-4H-quinazolin-3-yl]-N-isopropylacetamide hydrochloride (EXAMPLE 3a) (743 mg, 1.39 mmol, 37%).

Data for 2-[2-(3-chlorophenyl)-4-oxo-6-(3-piperidin-1-yl-propoxy)-4H-quinazolin-3-yl]-N-isopropylacetamide (free base): mp=206-208.5° C. (dec.); $^1$H NMR (300 MHz, CD$_3$OD): δ 7.68-7.45 (m, 7H), 4.59 (s, 2H), 4.19 (t, 2H), 3.93 (septet, 1H), 2.75-2.55 (m, 6H), 2.12 (m, 2H), 1.68 (m, 4H), 1.53 (m, 2H), 1.11 (d, 6H) ppm; MS (ESI) m/z: 497/499 ([M+H]$^+$).

Data for 2-[2-(3-chlorophenyl)-4-oxo-6-(3-piperidin-1-yl-propoxy)-4H-quinazolin-3-yl]-N-isopropylacetamide hydrochloride (EXAMPLE 3a): $^1$H NMR (300 MHz, CD$_3$OD): δ 7.76-7.56 (m, 7H), 4.65 (s, 2H), 4.29 (t, 2H), 3.93 (septet, 1H), 3.63 (br d, 2H), 3.39-3.30 (m, 2H, partially obscured by solvent peak), 3.01 (br t, 2H), 2.33 (m, 2H), 2.03-1.50 (m, 6H), 1.11 (d, 6H) ppm; MS (ESI) m/z: 497/499 ([M+H]$^+$).

The following compounds (EXAMPLES 3b-3v) were prepared in a similar manner:

Example 3b

N-Cyclopropylmethyl-2-[2-(3-methoxyphenyl)-6-(3-morpholin-4-ylpropoxy)-4-oxo-4H-quinazolin-3-yl]acetamide, MS (ESI) m/z: 507 ([M+H]$^+$) (from INTERMEDIATES VII.6 & III.2)

Example 3c

N-Cyclopropyl-2-[2-(3-methoxyphenyl)-6-(3-morpholin-4-ylpropoxy)-4-oxo-4H-quinazolin-3-yl]acetamide hydrochloride, MS (ESI) m/z: 493 ([M+H]$^+$) (from INTERMEDIATES VII.5 & III.2)

Example 3d

2-[2-(3-Chlorophenyl)-6-(3-morpholin-4-ylpropoxy)-4-oxo-4H-quinazolin-3-yl]-N-cyclopropylmethylacetamide, MS (ESI) m/z: 511/513 ([M+H]$^+$) (from INTERMEDIATES VII.6 & III.1)

Example 3e

N-Cyclopropylmethyl-2-[6-(3-morpholin-4-ylpropoxy)-4-oxo-2-o-tolyl-4H-quinazolin-3-yl]acetamide, MS (ESI) m/z: 491 ([M+H]$^+$) (from INTERMEDIATES VII.6 & III.8)

Example 3f

N-Cyclopropylmethyl-2-[2-(4-fluorophenyl)-6-(3-morpholin-4-ylpropoxy)-4-oxo-4H-quinazolin-3-yl]acetamide, MS (ESI) m/z: 495 ([M+H]$^+$) (from INTERMEDIATES VII.6 & III.9)

Example 3g

N-Cyclopropyl-2-[6-(3-morpholin-4-ylpropoxy)-4-oxo-2-m-tolyl-4H-quinazolin-3-yl]acetamide, MS (ESI) m/z: 477 ([M+H]$^+$) (from INTERMEDIATES VII.5 & III.10)

Example 3h

N-Cyclopropylmethyl-2-[6-(3-morpholin-4-ylpropoxy)-4-oxo-2-thiophen-2-yl-4H-quinazolin-3-yl]acetamide, MS (ESI) m/z: 483 ([M+H]$^+$) (from INTERMEDIATES VII.6 & III.11)

Example 3i

2-[2-(3-Chlorophenyl)-6-(3-morpholin-4-ylpropoxy)-4-oxo-4H-quinazolin-3-yl]-N-isopropylacetamide, MS (ESI) m/z: 499/501 ([M+H]$^+$) (from INTERMEDIATES VII.2 & III.1)

Example 3j

2-[2-(3-Chlorophenyl)-6-(3-morpholin-4-ylpropoxy)-4-oxo-4H-quinazolin-3-yl]-N-cyclopropylacetamide, MS (ESI) m/z: 497/499 ([M+H]$^+$) (from INTERMEDIATES VII.5 & III.1)

Example 3k

N-Cyclopropylmethyl-2-[2-(3,5-dimethoxyphenyl)-6-(3-morpholin-4-ylpropoxy)-4-oxo-4H-quinazolin-3-yl]acetamide, MS (ESI) m/z: 537 ([M+H]$^+$) (from INTERMEDIATES VII.6 & III.12)

Example 3l

2-[2-(3-Ethylphenyl)-4-oxo-6-(3-piperidin-1-ylpropoxy)-4H-quinazolin-3-yl]-N-isopropylacetamide, MS (ESI) m/z: 491 ([M+H]$^+$) (from INTERMEDIATES VII.1 & III.13)

Example 3m

N-Cyclopropyl-2-[2-(3-methoxyphenyl)-4-oxo-6-(3-piperidin-1-ylpropoxy)-4H-quinazolin-3-yl]acetamide, MS (ESI) m/z: 491 ([M+H]$^+$) (from INTERMEDIATES VII.3 & III.2)

Example 3n

2-[2-(2,3-Dichlorophenyl)-4-oxo-6-(3-piperidin-1-ylpropoxy)-4H-quinazolin-3-yl]-N-isopropylacetamide, MS (ESI) m/z: 531/533 ([M+H]$^+$) (from INTERMEDIATES VII.1 & III.14)

Example 3o

N-Isopropyl-2-{2-(3-methoxyphenyl)-6-[3-(4-methylpiperazin-1-yl)propoxy]-4-oxo-4H-quinazolin-3-yl}acetamide, MS (ESI) m/z: 508 ([M+H]$^+$) (from INTERMEDIATES VII.4 & III.2)

Example 3p

2-[2-(5-Chlorothiophen-2-yl)-4-oxo-6-(3-piperidin-1-ylpropoxy)-4H-quinazolin-3-yl]-N-isopropylacetamide, MS (ESI) m/z: 503/505 ([M+H]$^+$) (from INTERMEDIATES VII.1 & III.15)

Example 3q

2-[2-Cyclohexyl-4-oxo-6-(3-piperidin-1-ylpropoxy)-4H-quinazolin-3-yl]-N-isopropylacetamide, MS (ESI) m/z: 469 ([M+H]$^+$) (from INTERMEDIATES VII.1 & III.16)

Example 3r

N-Isopropyl-2-[6-[(4-methoxybenzyl)-(3-piperidin-1-ylpropyl)amino]-2-(3-methoxyphenyl)-4-oxo-4H-quinazolin-3-yl]acetamide, MS (ESI) m/z: 612 ([M+H]$^+$) (from INTERMEDIATES X.1 & III.2)

Example 3s

N-Isopropyl-2-{2-(3-methoxyphenyl)-6-[methyl(3-piperidin-1-yl-propyl)amino]-4-oxo-4H-quinazolin-3-yl}acetamide, MS (ESI) m/z: 506 ([M+H]$^+$) (from INTERMEDIATES X.2 & III.2)

Example 3t

N-Isopropyl-2-[2-(3-methoxyphenyl)-4-oxo-6-(3-piperidin-1-ylpropylsulfanyl)-4H-quinazolin-3-yl]acetamide, MS (ESI) m/z: 509 ([M+H]$^+$) (from INTERMEDIATES X.3 & III.2)

Example 3u

N-Cyclopropylmethyl-2-[2-(3-hydroxyphenyl)-6-(3-morpholin-4-ylpropoxy)-4-oxo-4H-quinazolin-3-yl]acetamide, MS (ESI) m/z: 493 ([M+H]$^+$) (from INTERMEDIATES VII.6 & III.17)

Example 3v

N-Cyclopropylmethyl-2-[2-(1H-indol-3-yl)-6-(3-morpholin-4-yl-propoxy)-4-oxo-4H-quinazolin-3-yl]-acetamide, MS (ESI) m/z: 517 ([M+H]$^+$) (from INTERMEDIATES VII.6 & III.7)

Example 4a (S)-(+)-2-[6-(3-Diethylamino-2-methylpropoxy)-2-(3-methoxyphenyl)-4-oxo-4H-quinazolin-3-yl]-N-isopropylacetamide

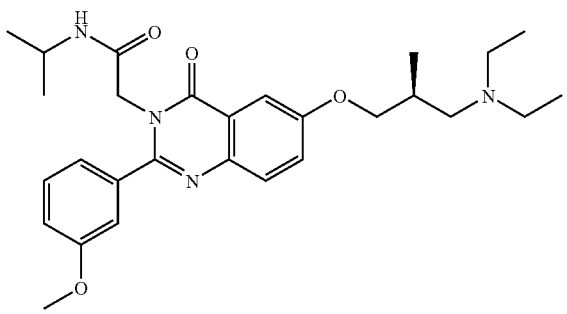

a) (S)-(+)-2-[6-(3-Hydroxy-2-methylpropoxy)-2-(3-methoxyphenyl)-4-oxo-4H-quinazolin-3-yl]-N-isopropylacetamide

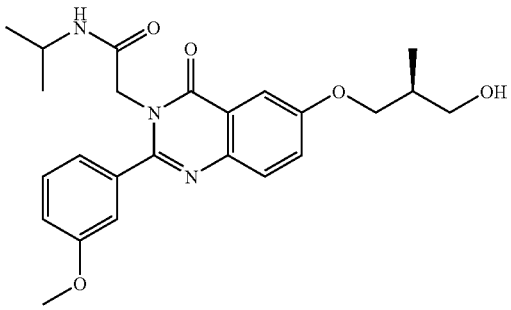

Method A

To a solution of 2-[6-hydroxy-2-(3-methoxyphenyl)-4-oxo-4H-quinazolin-3-yl]-N-isopropylacetamide (INTERMEDIATE IV.4) (1.80 g, 4.9 mmol) in anhydrous acetonitrile (50 mL) was added S-(+)-3-bromo-2-methyl-1-propanol (2.25 g, 1.52 mL, 14.7 mmol) and K$_2$CO$_3$ (3.39 g, 24.5 mmol) and the mixture stirred at reflux temperature for 21 h. The reaction mixture was cooled and partitioned between ethyl acetate (100 mL) and water (300 mL) and a white precipitate formed. Filtration under vacuum, followed by drying (vacuum oven, 80° C.) afforded (S)-(+)-2-[6-(3-hydroxy-2-methylpropoxy)-2-(3-methoxyphenyl)-4-oxo-4H-quinazolin-3-yl]-N-isopropylacetamide (1.07 g, 2.4 mmol, 50%) as a white solid.

Data for (S)-(+)-2-[6-(3-hydroxy-2-methylpropoxy)-2-(3-methoxyphenyl)-4-oxo-4H-quinazolin-3-yl]-N-isopropylacetamide: $^1$H NMR (300 MHz, CD$_3$OD) δ 7.68-7.63 (m, 2H), 7.50-7.41 (m, 2H), 7.15-7.10 (m, 3H), 4.59 (s, 2H), 4.13 (m, 1H), 4.02 (m, 1H), 3.93 (m, 1H), 3.84 (s, 3H), 3.69-3.58 (m, 2H), 2.17 (m, 1H), 1.10 (d, 9H) ppm.

Method B

A mixture of crude (S)-(+)-2-amino-5-(3-hydroxy-2-methylpropoxy)-N-(isopropylcarbamoylmethyl)benzamide (INTERMEDIATE VII.1) (223 mg, 0.70 mmol) (prepared in Procedure VIII) and ethyl 3-methoxybenzimidate*HCl (INTERMEDIATE III.2) (449 mg, 2.08 mmol) in anhydrous ethanol (5 mL) was heated to 80° C. in a tightly capped scintillation vial for 16 h. This was then cooled and concentrated in vacuo. The crude residue was partitioned between dichloromethane/2-propanol (3:1, v/v) and water and the aqueous extracted with further dichloromethane/2-propanol (3:1, v/v). The combined organics were dried (MgSO$_4$), filtered and concentrated in vacuo. The crude solid thus obtained was suspended in cold ethyl acetate and collected by filtration affording (S)-(+)-2-[6-(3-hydroxy-2-methylpropoxy)-2-(3-methoxyphenyl)-4-oxo-4H-quinazolin-3-yl]-N-isopropylacetamide (145 mg, 0.33 mmol, 43% from 2-amino-5-[(S)-(+)-3-hydroxy-2-methylpropoxy]benzoic acid) as a light brown solid.

b) (R)-(−)-Methanesulfonic acid 3-[3-(isopropylcarbamoylmethyl)-2-(3-methoxyphenyl)-4-oxo-3,4-dihydroquinazolin-6-yloxy]-2-methylpropyl ester

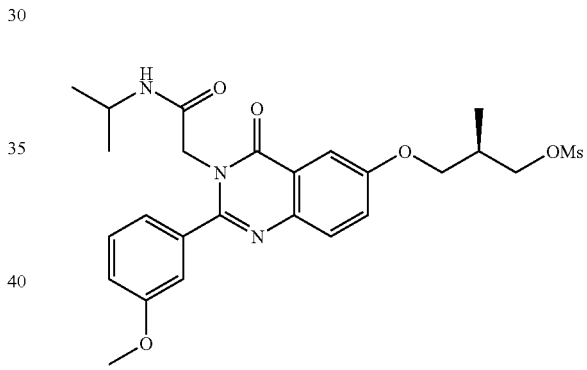

To a suspension of (S)-(+)-2-[6-(3-hydroxy-2-methylpropoxy)-2-(3-methoxyphenyl)-4-oxo-4H-quinazolin-3-yl]-N-isopropylacetamide (0.96 g, 2.18 mmol) in dichloromethane (100 mL) cooled to −78° C. under argon was added methanesulfonyl chloride (2.50 g, 1.7 mL, 21.90 mmol) dropwise over 5 min, followed by dropwise addition (10 min) of triethylamine (2.21 g, 3.10 mL, 21.9 mmol). The reaction mixture was warmed to −30° C. over 60 min followed by warming to room temperature over 15 min after which time the reaction was found to be complete (HPLC monitoring). The reaction mixture was diluted with ethyl acetate (300 mL), poured into ice water (100 mL) and the organic phase washed with 1N HCl (aq.) (2×200 mL), sat. NaHCO$_3$ (aq.) (1×200 mL) and brine (1×200 mL). The organic phase was dried (MgSO$_4$) and concentrated in vacuo to afford (R)-(−)-methanesulfonic acid 3-[3-(isopropylcarbamoylmethyl)-2-(3-methoxyphenyl)-4-oxo-3,4-dihydroquinazolin-6-yloxy]-2-methylpropyl ester as a pale yellow solid (1.13 g, 2.18 mmol, 100%, 91% purity by LC-MS).

c) (S)-(+)-2-[6-(3-Diethylamino-2-methylpropoxy)-2-(3-methoxyphenyl)-4-oxo-4H-quinazolin-3-yl]-N-isopropylacetamide

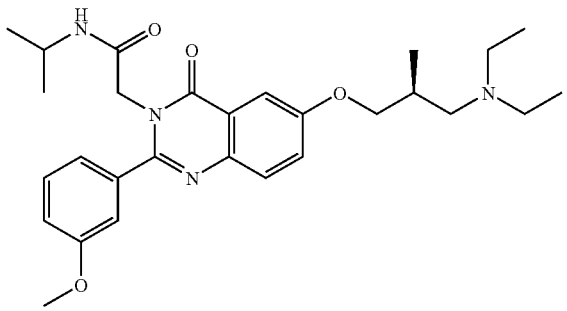

To a solution of (R)-(−)-methanesulfonic acid 3-[3-(isopropylcarbamoylmethyl)-2-(3-methoxyphenyl)-4-oxo-3,4-dihydroquinazolin-6-yloxy]-2-methylpropyl ester (1.13 g, 2.18 mmol) in anhydrous acetonitrile (40 mL) was added potassium carbonate (1.51 g, 10.95 mmol) followed by diethyl amine (3.20 g, 4.53 mL, 43.80 mmol) and the reaction mixture was heated at 80° C. in a pressure tube. After 2 days (reaction complete by HPLC), the reaction mixture was concentrated in vacuo to dryness and the residue was partitioned between water (100 mL) and ethyl acetate (150 mL). The aqueous layer was extracted with ethyl acetate (5×150 mL) and with dichloromethane (5×100 mL). The combined organic phase was dried ($Na_2SO_4$), solvent evaporated in vacuo, and the resulting residue purified by chromatography on silica gel with a gradient of methanol:dichloromethane (1:19, v/v) to methanol:dichloromethane (1:4, v/v) as eluent. The resultant solid was recrystallised from diethyl ether:hexane to afford (S)-(+)-2-[6-(3-diethylamino-2-methylpropoxy)-2-(3-methoxyphenyl)-4-oxo-4H-quinazolin-3-yl]-N-isopropy-acetamide (EXAMPLE 4a) (0.69 g, 1.40 mmol, 65% from (S)-(+)-2-[6-(3-hydroxy-2-methylpropoxy)-2-(3-methoxyphenyl)-4-oxo-4H-quinazolin-3-yl]-N-isopropylacetamide) as a white solid.

Data for 2-[6-(3-diethylamino-2-methyl-propoxy)-2-(3-methoxy-phenyl)-4-oxo-4H-quinazolin-3-yl]-N-isopropyl-acetamide (EXAMPLE 4a): M.p. 161-163° C.; $^1$H NMR (300 MHz, $CD_3OD$) δ 7.68-7.63 (m, 2H), 7.50-7.41 (m, 2H), 7.15-7.10 (m, 3H), 4.59 (s, 2H), 4.10-4.04 (m, 2H), 3.96-3.90 (m, 1H), 3.84 (s, 3H), 2.67 (m, 6H), 2.24 (m, 1H), 1.10 (overlapping signals, 15H) ppm; MS (ESI) m/z: 495 ([M+H]$^+$).

The following compounds (Examples 4b-4v) were prepared in a similar manner:

Method A

Example 4b (S)-(+)-N-Cyclopropylmethyl-2-[6-(2-methyl-3-morpholin-4-ylpropoxy)-4-oxo-2-phenyl-4H-quinazolin-3-yl]acetamide, MS (ESI) m/z: 491 ([M+H]$^+$) (from INTERMEDIATE IV.6)

Example 4c (S)-(+)-2-[2-(3-Chlorophenyl)-6-(2-methyl-3-pyrrolidin-1-ylpropoxy)-4-oxo-4H-quinazolin-3-yl]-N-isopropylacetamide, MS (ESI) m/z: 497/499 ([M+H]$^+$) (from INTERMEDIATE IV.14)

Example 4d (S)-(+)-N-Isopropyl-2-[2-(3-methoxyphenyl)-4-oxo-7-(2-piperidin-1-ylethoxy)-4H-quinazolin-3-yl]acetamide, MS (ESI) m/z: 479 ([M+H]$^+$) (from INTERMEDIATE IV.18)

Example 4e (S)-(+)-N-Isopropyl-2-[2-(3-methoxyphenyl)-4-oxo-7-(3-piperidin-1-ylpropoxy)-4H-quinazolin-3-yl]acetamide, MS (ESI) m/z: 493 ([M+H]$^+$) (from INTERMEDIATE IV.18)

Method B

Example 4f (S)-(+)-2-[6-(3-Dimethylamino-2-methylpropoxy)-2-(3-methoxyphenyl)-4-oxo-4H-quinazolin-3-yl]-N-isopropylacetamide, MS (ESI) m/z: 467 ([M+H]$^+$) (from INTERMEDIATES VIII.1 & III.2)

Example 4g (S)-(+)-2-[2-(3-Fluorophenyl)-6-(2-methyl-3-morpholin-4-ylpropoxy)-4-oxo-4H-quinazolin-3-yl]-N-isopropylacetamide, MS (ESI) m/z: 497 ([M+H]$^+$) (from INTERMEDIATES VIII.1 & III.18)

Example 4h (S)-(+)-2-[6-(3-Dimethylamino-2-methylpropoxy)-2-(3-fluorophenyl)-4-oxo-4H-quinazolin-3-yl]-N-isopropylacetamide, MS (ESI) m/z: 455 ([M+H]$^+$) (from INTERMEDIATES VIII.1 & III.18)

Example 4i (S)-(+)-2-[6-(3-Azetidin-1-yl-2-methylpropoxy)-2-(3-methoxyphenyl)-4-oxo-4H-quinazolin-3-yl]-N-isopropylacetamide, MS (ESI) m/z: 479 ([M+H]$^+$) (from INTERMEDIATES VIII.1 & III.2)

Example 4j (S)-(+)-2-[2-(3-Fluorophenyl)-6-(2-methyl-3-pyrrolidin-1-ylpropoxy)-4-oxo-4H-quinazolin-3-yl]-N-isopropylacetamide, MS (ESI) m/z: 481 ([M+H]$^+$) (from INTERMEDIATES VIII.1 & III.18)

Example 4k (S)-(+)-N-Isopropyl-2-[2-(3-methoxyphenyl)-6-(2-methyl-3-pyrrolidin-1-ylpropoxy)-4-oxo-4H-quinazolin-3-yl]acetamide, MS (ESI) m/z: 493 ([M+H]$^+$) (from INTERMEDIATES VIII.1 & III.2)

Example 4l (S)-(+)-N-Ethyl-2-[2-(3-methoxyphenyl)-6-(2-methyl-3-piperidin-1-ylpropoxy)-4-oxo-4H-quinazolin-3-yl]acetamide, MS (ESI) m/z: 493 ([M+H]$^+$) (from INTERMEDIATES VIII.4 & III.2)

Example 4m (S)-(+)-2-[2-(3-Chlorophenyl)-6-(2-methyl-3-piperidin-1-ylpropoxy)-4-oxo-4H-quinazolin-3-yl]-N-propylacetamide, MS (ESI) m/z: 511/513 ([M+H]$^+$) (from INTERMEDIATES VIII.5 & III.1)

Example 4n (S)-(+)-2-[2-(3-Methoxyphenyl)-6-(2-methyl-3-piperidin-1-ylpropoxy)-4-oxo-4H-quinazolin-3-yl]-N-propylacetamide, MS (ESI) m/z: 507 ([M+H]$^+$) (from INTERMEDIATES VIII.5 & III.2)

Example 4o (S)-(+)-2-[2-(3-Fluorophenyl)-6-(2-methyl-3-piperidin-1-ylpropoxy)-4-oxo-4H-quinazolin-3-yl]-N-isopropylacetamide, MS (ESI) m/z: 495 ([M+H]$^+$) (from INTERMEDIATES VIII.1 & III.18)

Example 4p

N-Cyclopropylmethyl-2-{6-[3-(3,4-dihydro-1H-isoquinolin-2-yl)propoxy]-4-oxo-2-phenyl-4H-quinazolin-3-yl}acetamide, MS (ESI) m/z: 523 ([M+H]$^+$) (from INTERMEDIATE VII.6)

Example 4q

2-[6-(3-Azepan-1-ylpropoxy)-4-oxo-2-phenyl-4H-quinazolin-3-yl]-N-cyclopropylmethylacetamide, MS (ESI) m/z: 489 ([M+H]$^+$) (from INTERMEDIATE VIII.6)

Example 4r

N-Cyclopropylmethyl-2-[4-oxo-2-phenyl-6-(3-thiomorpholin-4-ylpropoxy)-4H-quinazolin-3-yl]acetamide, MS (ESI) m/z: 493 ([M+H]$^+$) (from INTERMEDIATE V11.6)

Example 4s (S)-(+)-2-[6-(3-Diethylamino-2-methylpropoxy)-2-(3-fluorophenyl)-4-oxo-4H-quinazolin-3-yl]-N-isopropylacetamide, MS (ESI) m/z: 483 ([M+H]$^+$) (from INTERMEDIATES VIII.1 & III.18)

Example 4t

N-Cyclopropylmethyl-2-{6-[3-(1,2,3,6-tetrahydropyridin-1-yl)-propoxy]-4-oxo-2-phenyl-4H-quinazolin-3-yl}acetamide, MS (ESI) m/z: 473 ([M+H]$^+$) (from INTERMEDIATE VIII.6)

Example 4u

2-{6-[3-(4-Cyanopiperidin-1-yl)propoxy]-4-oxo-2-phenyl-4H-quinazolin-3-yl}-N-cyclopropylmethylacetamide, MS (ESI) m/z: 500 ([M+H]$^+$) (from INTERMEDIATE VIII.6)

Example 4v 1-(3-{3-[(Cyclopropylmethylcarbamoyl)methyl]-4-oxo-2-phenyl-3,4-dihydroquinazolin-6-yloxy}propyl)piperidine-4-carboxylic acid ethyl ester, MS (ESI) m/z: 547 ([M+H]$^+$) (from INTERMEDIATE VIII.6)

Example 5a

N-Cyclopropylmethyl-2-[4-oxo-2-phenyl-6-([1S,3S]-3-piperidin-1-ylcyclopentyloxy)-4H-quinazolin-3-yl]acetamide

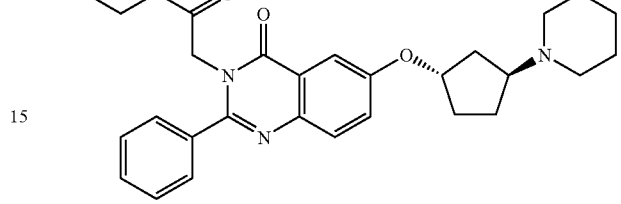

A mixture of crude (1S,3R)-3-piperidin-1-ylcyclopentyl methanesulphonate (INTERMEDIATE XII.1) (90 mg, 0.4 mmol), N-cyclopropylmethyl-2-(6-hydroxy-4-oxo-2-phenyl-4H-quinazolin-3-yl)acetamide (INTERMEDIATE IV.6) (71 mg, 0.2 mmol) and Cs$_2$CO$_3$ (326 mg, 1.0 mmol) in DMSO (0.3 mL) was heated at 80° C. for 16 h. The mixture was then cooled and diluted with water. The aqueous layer was extracted with ethyl acetate (3×20 mL). The combined organics were dried (MgSO$_4$), filtered and concentrated in vacuo. The residue was purified by chromatography on silica gel with methanol:dichloromethane (1:9, v/v) as eluent to afford N-cyclopropylmethyl-2-[4-oxo-2-phenyl-6-((1S,3S)-3-piperidin-1-ylcyclopentyloxy)-4H-quinazolin-3-yl]acetamide (EXAMPLE 5a) (14 mg, 0.029 mmol, 14%).

Data for N-cyclopropylmethyl-2-[4-oxo-2-phenyl-6-((1S,3S)-3-piperidin-1-ylcyclopentyloxy)-4H-quinazolin-3-yl]acetamide (EXAMPLE 5a: $^1$H NMR (300 MHz, CD$_3$OD): δ 7.66-7.40 (m, 8H), 4.94-4.92 (m, 1H), 4.61 (s, 2H), 3.04-3.02 (d, 2H), 2.80-2.78 (m, 1H), 2.62-2.58 (br m, 5H), 2.1-1.9 (m, 3H), 1.8-1.7 (m, 2H), 1.68-1.58 (m, 4H), 1.56-1.4 (m, 2H), 0.95-0.89 (m, 1H), 0.52-0.46 (m, 2H), 0.21-0.16 (m, 2H) ppm; MS (ESI) m/z: 501 ([M+H]$^+$).

Example 6a

2-[6-(5-Dimethylaminomethyl-2-fluorophenyl)-2-(3-methoxyphenyl)-4-oxo-4H-quinazolin-3-yl]-N-isopropylacetamide

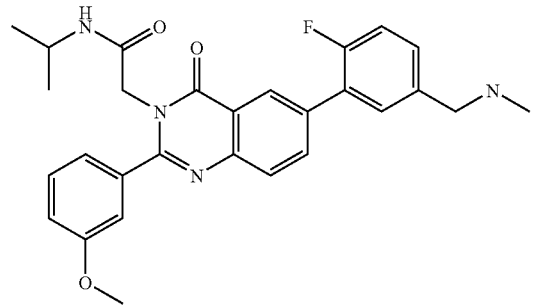

a) N-Isopropyl-2-[2-(3-methoxyphenyl)-4-oxo-6-(4,4,5,5-tetramethyl [1,3,2]dioxaborolan-2-yl)-4H-quinazolin-3-yl]acetamide

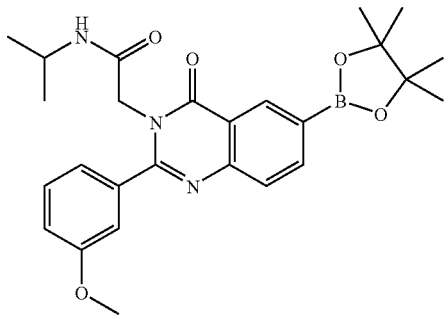

Bis(pinacolato)diboron (0.59 g, 2.33 mmol), potassium acetate (0.34 g, 3.50 mmol) and PdCl$_2$(dppf) (95 mg, 0.12 mmol) were added sequentially to a degassed solution of 2-[6-bromo-2-(3-methoxyphenyl)-4-oxo-4H-quinazolin-3-yl]-N-isopropylacetamide (INTERMEDIATE IV.10) (0.50 g, 1.16 mmol) in anhydrous DMF (50 mL) and the reaction mixture was heated at 80° C. for 24 h. The solvent was removed in vacuo and the brown residue partitioned between water and ethyl acetate. The organic layer was washed with water and brine, dried (Na$_2$SO$_4$) and the solvent evaporated in vacuo. The residue was purified by chromatography on silica gel with ethyl acetate:dichloromethane (3:7, v/v) as eluent to give N-isopropyl-2-[2-(3-methoxyphenyl)-4-oxo-6-(4,4,5,5-tetramethyl[1,3,2]dioxaborolan-2-yl)-4H-quinazolin-3-yl] acetamide (0.51 g, 1.07 mmol, 92%).

Data for N-isopropyl-2-[2-(3-methoxyphenyl)-4-oxo-6-(4,4,5,5-tetramethyl[1,3,2]dioxaborolan-2-yl)-4H-quinazolin-3-yl]acetamide: $^1$H NMR (300 MHz, CDCl$_3$) δ 8.78 (s, 1H), 8.16 (d, 1H), 7.72 (d, 1H), 7.38 (t, 1H), 7.20 (m, 2H), 7.03 (m, 1H), 5.74 (br d, 1H), 4.51 (s, 2H), 4.05 (m, 1H), 3.84 (s, 3H), 1.37 (s, 12H), 1.15 (d, 6H) ppm; MS (ESI) m/z: 478 ([M+H]$^+$).

b) 2-[6-(2-Fluoro-5-formylphenyl)-2-(3-methoxyphenyl)-4-oxo-4H-quinazolin-3-yl]-N-isopropylacetamide

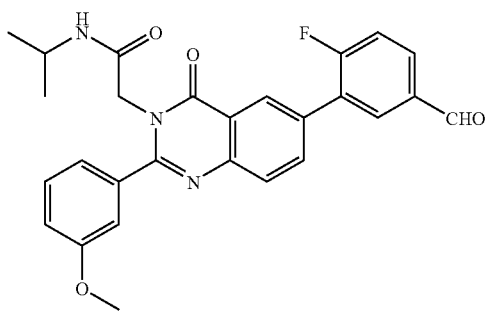

To a solution of N-isopropyl-2-[2-(3-methoxyphenyl)-4-oxo-6-(4,4,5,5-tetramethyl[1,3,2]dioxaborolan-2-yl)-4H-quinazolin-3-yl]acetamide (70 mg, 0.15 mmol) in DMF (3 mL) was added 3-bromo-4-fluorobenzaldehyde (70 mg, 0.34 mmol), followed by tetrakis(triphenylphosphine)palladium (Pd[P(C$_6$H$_5$)$_3$]$_4$) (24 mg, 0.02 mmol) and 2M K$_3$PO$_4$ (aq.) (0.38 mL, 0.76 mmol). The mixture was heated at 80° C. under argon for 20 h, then cooled to room temperature and DMF evaporated in vacuo. The crude product was purified by preparative thin layer chromatography on silica gel with methanol:dichloromethane (1:9, v/v) as eluent to provide 2-[6-(2-fluoro-5-formylphenyl)-2-(3-methoxyphenyl)-4-oxo-4H-quinazolin-3-yl]-N-isopropylacetamide (19.3 mg, 0.04 mmol, 27% yield).

Data for 2-[6-(2-fluoro-5-formylphenyl)-2-(3-methoxyphenyl)-4-oxo-4H-quinazolin-3-yl]-N-isopropylacetamide: $^1$H NMR (CDCl$_3$) δ 10.05 (s, 1H), 8.53 (s, 1H), 8.10 (dd, 1H), 8.02 (m, 1H), 7.96 (m, 1H), 7.87 (m, 1H), 7.40 (m, 2H), 7.21 (m, 2H), 7.06 (m, 1H), 5.52 (br d, 1H), 4.55 (s, 2H), 4.09 (m, 1H), 3.85 (s, 3H), 1.16 (d, 6H) ppm; MS (ESI) m/z: 474 ([M+H]$^+$)

c) 2-[6-(5-Dimethylaminomethyl-2-fluorophenyl)-2-(3-methoxyphenyl)-4-oxo-4H-quinazolin-3-yl]-N-isopropylacetamide

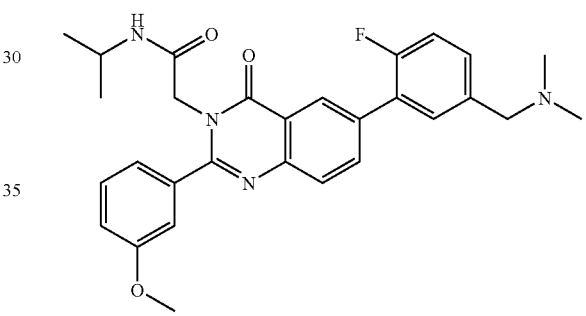

To a solution of 2-[6-(2-fluoro-5-formylphenyl)-2-(3-methoxyphenyl)-4-oxo-4H-quinazolin-3-yl]-N-isopropylacetamide (19 mg, 0.04 mmol) in dichloroethane (2 mL) and acetic acid (0.05 mL) was added dimethylamine (2M in acetonitrile, 0.50 mL, 1.0 mmol) and the reaction mixture was stirred at room temperature for 30 minutes. Sodium triacetoxyborohydride (70 mg, 0.33 mmol) was then added as a solid with stirring at room temperature for 24 h. The solvent was removed in vacuo, the residue partitioned between ethyl acetate and a 1 N NaOH (aq.), the organic layer was washed with brine, dried (MgSO$_4$) and the solvent evaporated. The resulting residue was subjected to preparative HPLC purification to provide 2-[6-(5-dimethylaminomethyl-2-fluorophenyl)-2-(3-methoxyphenyl)-4-oxo-4H-quinazolin-3-yl]-N-isopropylacetamide (EXAMPLE 6a) (10 mg, 0.02 mmol, 50%).

Data for 2-[6-(5-dimethylaminomethyl-2-fluorophenyl)-2-(3-methoxyphenyl)-4-oxo-4H-quinazolin-3-yl]-N-isopropylacetamide (EXAMPLE 6a): $^1$H NMR (300 MHz, CD$_3$OD): δ 8.48 (br s, 1H), 8.12-8.05 (m, 1H), 8.03-8.00 (m, 1H), 7.83-7.78 (m, 2H), 7.62-7.56 (m, 1H), 7.52-7.38 (m, 2H), 7.22-7.14 (m, 3H), 4.62 (s, 2H), 4.40 (s, 2H), 3.93 (septet, 1H), 3.84 (s, 3H), 2.92 (s, 6H), 1.05 (d, 6H) ppm; MS (ESI) m/z: 503 ([M+H]$^+$).

The following compounds (Examples 6b-6c) were prepared in a similar manner:

Example 6b

2-[6-(6-Dimethylaminomethylpyridin-2-yl)-2-(3-methoxyphenyl)-4-oxo-4H-quinazolin-3-yl]-N-isopropylacetamide, MS (ESI) m/z: 486 ([M+H]$^+$) (from INTERMEDIATE IV.10)

Example 6c

2-[6-(4-Dimethylaminomethylpyridin-2-yl)-2-(3-methoxyphenyl)-4-oxo-4H-quinazolin-3-yl]-N-isopropylacetamide, MS (ESI) m/z: 486 ([M+H]$^+$) (from INTERMEDIATE IV.10)

Example 7a

N-Cyclopropylmethyl-2-[4-oxo-2-phenyl-6-(3-piperidin-1-ylmethylphenyl)-4H-quinazolin-3-yl]acetamide

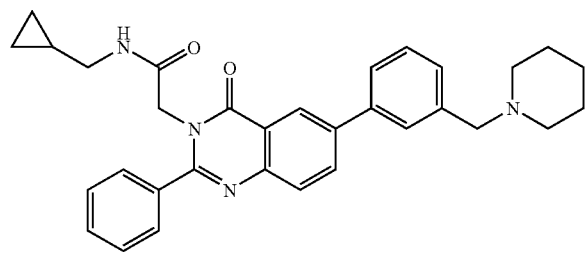

a) Trifluoromethanesulfonic acid 3-[(cyclopropylmethylcarbamoyl)methyl]-4-oxo-2-phenyl-3,4-dihydroquinazolin-6-yl ester

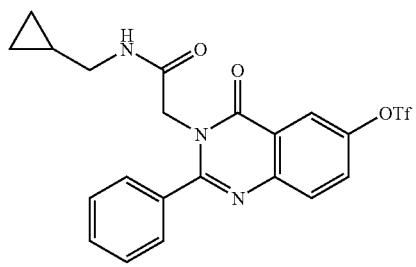

N-Cyclopropyl methyl-2-(6-hydroxy-4-oxo-2-phenyl-4H-quinazolin-3-yl)acetamide (INTERMEDIATE IV.6) (0.35 g, 1.0 mmol) was dissolved in dry pyridine (7 mL). The solution was cooled to 0° C. and trifluoromethanesulfonic anhydride (0.5 ml, 3 mmol) was added dropwise. After 1 h the mixture was concentrated, dissolved in dichloromethane and washed with saturated NaHCO$_3$ (aq.) and brine. The organic layer was dried (MgSO$_4$) and concentrated to yield trifluoromethanesulfonic acid 3-[(cyclopropylmethylcarbamoyl)methyl]-4-oxo-2-phenyl-3,4-dihydroquinazolin-6-yl ester (0.33 g, 0.68 mmol, 68%) as a yellow solid.

Data for trifluoromethanesulfonic acid 3-[(cyclopropylmethylcarbamoyl)methyl]-4-oxo-2-phenyl-3,4-dihydroquinazolin-6-yl ester: MS (ESI) m/z: 486 ([M+H]$^+$).

b) N-Cyclopropylmethyl-2-[6-(3-hydroxymethylphenyl)-4-oxo-2-phenyl-4H-quinazolin-3-yl]acetamide

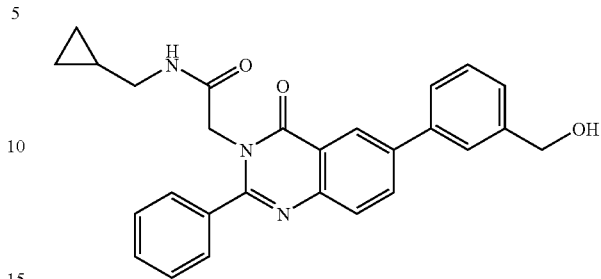

To trifluoromethanesulfonic acid 3-[(cyclopropylmethylcarbamoyl)methyl]-4-oxo-2-phenyl-3,4-dihydroquinazolin-6-yl ester (100 mg, 0.2 mmol) in acetone (2 mL) and water (1 mL) was added 3-hydroxyphenyl boronic acid (60 mg, 0.4 mmol), K$_2$CO$_3$ (excess), and tetrakis(triphenylphosphine) palladium (23 mg, 10 mol %). The solution was heated at 60° C. for 1 h. The resulting mixture was cooled to room temperature and the solid material collected by filtration, washed with acetone and dried in vacuo to give N-cyclopropylmethyl-2-[6-(3-hydroxymethylphenyl)-4-oxo-2-phenyl-4H-quinazolin-3-yl]acetamide (60 mg, 0.14 mmol, 68%).

Data for N-cyclopropylmethyl-2-[6-(3-hydroxymethylphenyl)-4-oxo-2-phenyl-4H-quinazolin-3-yl]acetamide: MS (ESI) m/z: 440 ([M+H]$^+$).

c) N-Cyclopropylmethyl-2-[4-oxo-2-phenyl-6-(3-piperidin-1-ylmethyl phenyl)-4H-quinazolin-3-yl] acetamide

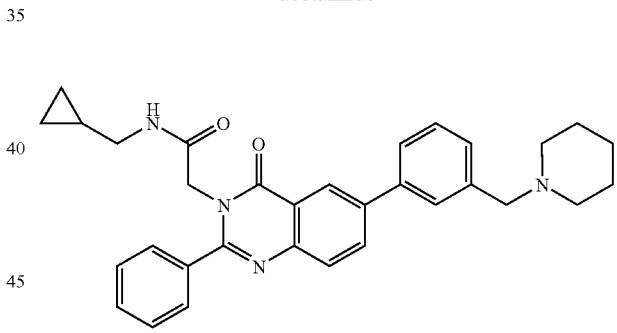

To N-cyclopropylmethyl-2-[6-(3-hydroxymethylphenyl)-4-oxo-2-phenyl-4H-quinazolin-3-yl]acetamide (10 mg, 0.02 mmol) in dichloromethane (1 mL) was added excess of triethyl amine (~250 µL) and methane sulfonyl chloride (~150 µL). After 1 h the mixture was concentrated to dryness. The resulting solid was suspended in dichloromethane (1 mL) and excess piperidine (0.5 mL) added. After stirring at room temperature for 1 h, the mixture was concentrated in vacuo, dissolved in dichloromethane and washed with 1 N NaOH (aq.) and brine. The organic layer was dried (Na$_2$SO$_4$), concentrated in vacuo and the resulting oil purified by chromatography on silica gel with a gradient of methanol:dichloromethane (1:19, v/v) to methanol:dichloromethane (1:9, v/v) as eluent. This afforded N-cyclopropylmethyl-2-[4-oxo-2-phenyl-6-(3-piperidin-1-ylmethylphenyl)-4H-quinazolin-3-yl]acetamide (EXAMPLE 7a) (4 mg, 0.01 mmol, 36%) as a tan-coloured solid.

Data for N-cyclopropylmethyl-2-[4-oxo-2-phenyl-6-(3-piperidin-1-ylmethylphenyl)-4H-quinazolin-3-yl]acetamide (EXAMPLE 7a): ¹H NMR (300 MHz, CDCl$_3$): δ 8.55 (d, 1H), 8.06 (dd, 1H), 7.76 (d, 1H), 7.70-7.4 (m, 9H), 5.95 (t, 1H), 4.58 (s, 2H), 3.59 (br s, 2H), 3.16 (dd, 2H), 2.46 (br m, 4H), 1.62 (br m, 4H), 1.45 (m, 2H), 0.90 (m, 1H), 0.52 (m, 2H), 0.21 (m, 2H) ppm; MS (ESI) m/z: 507 ([M+H]$^+$).

The following compounds (Examples 7b-7aa) were prepared in a similar manner:

Example 7b

N-Cyclopropylmethyl-2-[2-(3-methoxyphenyl)-4-oxo-6-(3-piperidin-1-ylmethylphenyl)-4H-quinazolin-3-yl]acetamide, MS (ESI) m/z: 537 ([M+H]$^+$) (from INTERMEDIATE IV.19)

Example 7c

2-[2-(3-Chlorophenyl)-4-oxo-6-(3-piperidin-1-ylmethyl phenyl)-4H-quinazolin-3-yl]-N-isopropylacetamide, MS (ESI) m/z: 529/531 ([M+H]$^+$) (from INTERMEDIATE IV.14)

Example 7d

N-Isobutyl-2-[2-(3-methoxyphenyl)-4-oxo-6-(3-piperidin-1-ylmethylphenyl)-4H-quinazolin-3-yl]acetamide, MS (ESI) m/z: 539 ([M+H]$^+$) (from INTERMEDIATE IV.20)

Example 7e

N-Isopropyl-2-[2-(3-methoxyphenyl)-4-oxo-6-(3-piperidin-1-ylmethylphenyl)-4H-quinazolin-3-yl]acetamide, MS (ESI) m/z: 525 ([M+H]$^+$) (from INTERMEDIATE IV.4)

Example 7f

N-Isopropyl-2-[2-(3-methoxyphenyl)-4-oxo-6-(3-pyrrolidin-1-ylmethylphenyl)-4H-quinazolin-3-yl]acetamide, MS (ESI) m/z: 511 ([M+H]$^+$) (from INTERMEDIATE IV.4)

Example 7g

2-[2-(3-Chlorophenyl)-4-oxo-6-(3-pyrrolidin-1-ylmethylphenyl)-4H-quinazolin-3-yl]-N-isopropylacetamide, MS (ESI) m/z: 515/517 ([M+H]$^+$) (from INTERMEDIATE IV.14)

Example 7h

2-[6-(3-Azetidin-1-ylmethylphenyl)-4-oxo-2-phenyl-4H-quinazolin-3-yl]-N-cyclopentylacetamide, MS (ESI) m/z: 493 ([M+H]$^+$) (from INTERMEDIATE IV.21)

Example 7i

2-[2-(3-Chlorophenyl)-6-(3-diethylaminomethylphenyl)-4-oxo-4H-quinazolin-3-yl]-N-isopropylacetamide, MS (ESI) m/z: 517/519 ([M+H]$^+$) (from INTERMEDIATE IV.14)

Example 7j

2-[6-(3-Diethylaminomethylphenyl)-2-(3-methoxyphenyl)-4-oxo-4H-quinazolin-3-yl]-N-isopropylacetamide, MS (ESI) m/z: 513 ([M+H]$^+$) (from INTERMEDIATE IV.4)

Example 7k

2-[6-(3-Dimethylaminomethylphenyl)-2-(3-methoxyphenyl)-4-oxo-4H-quinazolin-3-yl]-N-isopropylacetamide, MS (ESI) m/z: 485 ([M+H]$^+$) (from INTERMEDIATE IV.4)

Example 7l

2-[2-(3-Chlorophenyl)-6-(3-dimethylaminomethyl phenyl)-4-oxo-4H-quinazolin-3-yl]-N-isopropylacetamide, MS (ESI) m/z: 489/491 ([M+H]$^+$) (from INTERMEDIATE IV.14)

Example 7m

2-[6-(3-Dimethylaminomethyl-4-methoxyphenyl)-4-oxo-2-phenyl-4H-quinazolin-3-yl]-N-isobutylacetamide, MS (ESI) m/z: 499 ([M+H]$^+$) (from INTERMEDIATE IV.23)

Example 7n

2-[6-(3-Dimethylaminomethylphenyl)-2-(3-methoxyphenyl)-4-oxo-4H-quinazolin-3-yl]-N-isobutylacetamide, MS (ESI) m/z: 499 ([M+H]$^+$) (from INTERMEDIATE IV.20)

Example 7o 2-(2-(3-Chlorophenyl)-6-{3-[(isopropylmethylamino)methyl]phenyl}-4-oxo-4H-quinazolin-3-yl)-N-isopropylacetamide, MS (ESI) m/z: 517/519 ([M+H]$^+$) (from INTERMEDIATE IV.14)

Example 7p

2-[6-{3-[(Isobutylmethylamino)methyl]phenyl}-2-(3-methoxyphenyl)-4-oxo-4H-quinazolin-3-yl]-N-isopropylacetamide, MS (ESI) m/z: 527 ([M+H]$^+$) (from INTERMEDIATE IV.4)

Example 7q

N-Isopropyl-2-[6-{3-[(isopropyl methylamino)methyl]phenyl}-2-(3-methoxyphenyl)-4-oxo-4H-quinazolin-3-yl]acetamide, MS (ESI) m/z: 513 ([M+H]$^+$) (from INTERMEDIATE IV.4)

Example 7r

2-[6-{3-[(Ethylmethylamino)methyl]phenyl}-2-(3-methoxyphenyl)-4-oxo-4H-quinazolin-3-yl]-N-isopropylacetamide, MS (ESI) m/z: 499 ([M+H]$^+$) (from INTERMEDIATE IV.4)

Example 7s 2-(2-(3-Chlorophenyl)-6-{3-[(ethyl methylamino)methyl]phenyl}-4-oxo-4H-quinazolin-3-yl)-N-isopropylacetamide, MS (ESI) m/z: 503/505 ([M+H]$^+$) (from INTERMEDIATE IV.14)

Example 7t

2-[2-(3-Chlorophenyl)-6-(3-morpholin-4-ylmethylphenyl)-4-oxo-4H-quinazolin-3-yl]-N-isopropylacetamide, MS (ESI) m/z: 531/533 ([M+H]$^+$) (from INTERMEDIATE IV.14)

Example 7u

N-Isopropyl-2-[2-(3-methoxyphenyl)-6-(3-morpholin-4-yl-methylphenyl)-4-oxo-4H-quinazolin-3-yl]acetamide, MS (ESI) m/z: 527 ([M+H]$^+$) (from INTERMEDIATE IV.4)

Example 7v

2-{2-(3-Chlorophenyl)-6-[3-(4-hydroxypiperidin-1-ylmethyl)phenyl]-4-oxo-4H-quinazolin-3-yl}-N-isopropylacetamide, MS (ESI) m/z: 545/547 ([M+H]$^+$) (from INTERMEDIATE IV.14)

Example 7w

2-[6-[3-(4-Hydroxypiperidin-1-ylmethyl)phenyl]-2-(3-methoxyphenyl)-4-oxo-4H-quinazolin-3-yl]-N-isopropylacetamide, MS (ESI) m/z: 541 ([M+H]$^+$) (from INTERMEDIATE IV.4)

Example 7x

N-Allyl-2-[4-oxo-2-phenyl-6-(3-piperidin-1-ylmethyl phenyl)-4H-quinazolin-3-yl]acetamide, MS (ESI) m/z: 493 ([M+H]$^+$) (from INTERMEDIATE IV.22)

Example 7y

N-tert-Butyl-2-[6-(3-dimethylaminomethylphenyl)-2-(4-fluoro-3-methoxyphenyl)-4-oxo-4H-quinazolin-3-yl]acetamide, MS (ESI) m/z: 517 ([M+H]$^+$) (from INTERMEDIATE IV.25)

Example 7z

N-tert-Butyl-2-[2-(4-fluoro-3-methoxyphenyl)-4-oxo-6-(3-pyrrolidin-1-ylmethylphenyl)-4H-quinazolin-3-yl]acetamide, MS (ESI) m/z: 543 ([M+H]$^+$) (from INTERMEDIATE IV.25)

Example 7aa

2-[6-(3-Dimethylaminomethylphenyl)-2-(4-fluoro-3-methoxyphenyl)-4-oxo-4H-quinazolin-3-yl]-N-isopropylacetamide, MS (ESI) m/z: 503 ([M+H]$^+$) (from INTERMEDIATE IV.7)

Example 8a

2-[7-(3-Dimethylaminomethylphenyl)-2-(3-methoxyphenyl)-4-oxo-4H-quinazolin-3-yl]-N-isopropylacetamide

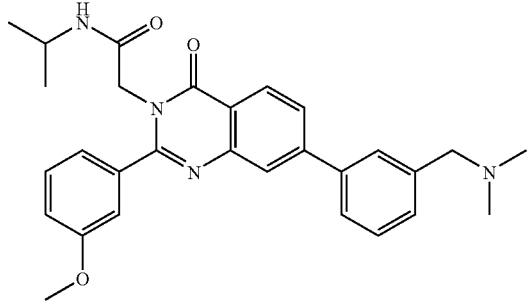

An oven dried flask was charged with 2-[7-chloro-2-(3-methoxyphenyl)-4-oxo-4H-quinazolin-3-yl]-N-isopropylacetamide (INTERMEDIATE IV.11) (38.5 mg, 0.10 mmol), dimethyl-[3-(4,4,5,5-tetramethyl[1,3,2]dioxaborolan-2-yl)benzyl]amine (INTERMEDIATE XI.1) (40 mg, 0.15 mmol) and K$_3$PO$_4$(69 mg, 0.33 mmol) followed by mixture of DMF:H$_2$O (4:1, 5 mL) and purged with argon for a minimum of 10 minutes. CombiPhos™-Pd catalyst (CombiPhos Catalysts Inc., Princeton, N.J.) (1 mole %) was added and the mixture was heated at 80° C. for 18 h. The solvent was removed under vacuum and the residue was dissolved in methanol, filtered and purified by preparative HPLC to give 2-[7-(3-dimethylaminomethylphenyl)-2-(3-methoxyphenyl)-4-oxo-4H-quinazolin-3-yl]-N-isopropylacetamide (EXAMPLE 8a) as a colorless oil.

Data for 2-[7-(3-dimethylaminomethylphenyl)-2-(3-methoxyphenyl)-4-oxo-4H-quinazolin-3-yl]-N-isopropylacetamide (EXAMPLE 8a): $^1$H NMR (300 MHz, CD$_3$OD) δ 8.39 (d, 1H), 7.99-7.79 (overlap of 4H), 7.67 (m, 1H), 7.60 (m, 1H), 7.48 (m, 1H), 7.20-7.15 (overlap of 3H), 4.62 (s, 2H), 4.43 (s, 2H), 3.96 (m, 1H), 3.86 (s, 3H), 2.92 (s, 6H), 1.11 (d, 6H) ppm; MS (ESI) m/z: 485 ([M+H]$^+$).

EXAMPLE 8b was prepared in a similar manner:

Example 8b

N-Isopropyl-2-[2-(3-methoxyphenyl)-4-oxo-7-(3-piperidin-1-ylmethylphenyl)-4H-quinazolin-3-yl]acetamide, MS (ESI) m/z: 525 ([M+H]$^+$) (from INTERMEDIATES IV.11 & XI.2)

Example 9a

2-[6-(5-Azetidin-1-ylmethylfuran-2-yl)-2-(3-methoxyphenyl)-4-oxo-4H-quinazolin-3-yl]-N-isopropylacetamide

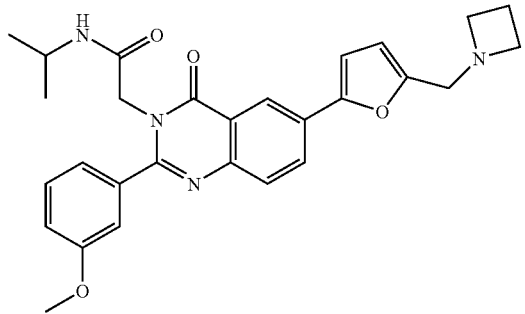

a) 2-[6-(5-Formylfuran-2-yl)-2-(3-methoxyphenyl)-4-oxo-4H-quinazolin-3-yl]-N-isopropylacetamide

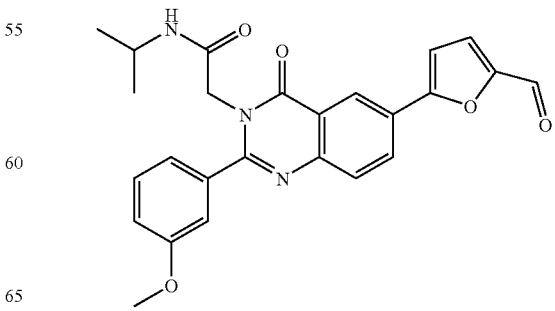

2-formylfuran-5-boronic acid (118 mg, 0.84 mmol) (Frontier Scientific), copper (I) thiophene-2-carboxylate (136 mg, 0.72 mmol) (Frontier Scientific), and tetrakis(triphenylphosphine)palladium (75 mg, 10 mol %) were added to a solution of 2-[6-iodo-2-(3-methoxyphenyl)-4-oxo-4H-quinazolin-3-yl]-N-isopropylacetamide (INTERMEDIATE IV.24) in tetrahydrofuran (10 mL) under Argon. The solution was stirred at room temperature for 2 h. The resulting mixture was concentrated in vacuo. The resulting oil was purified by chromatography on a silica gel with methanol:dichloromethane (1:19, v/v) as eluent to give 2-[6-(5-formylfuran-2-yl)-2-(3-methoxyphenyl)-4-oxo-4H-quinazolin-3-yl]-N-isopropylacetamide (90 mg, 0.20 mmol, 31%).

Data for 2-[6-(5-Formylfuran-2-yl)-2-(3-methoxyphenyl)-4-oxo-4H-quinazolin-3-yl]-N-isopropylacetamide:MS (ESI) m/z: 446 ([M+H]⁺).

b) 2-[6-(5-Azetidin-1-ylmethylfuran-2-yl)-2-(3-methoxyphenyl)-4-oxo-4H-quinazolin-3-yl]-N-isopropylacetamide

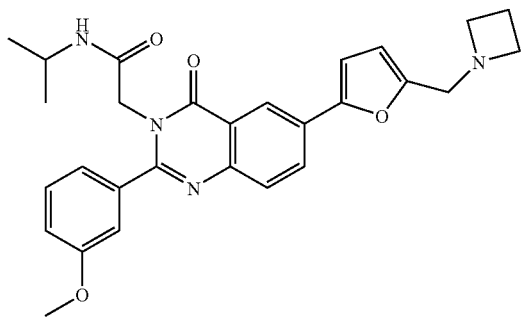

To a solution of 2-[6-(5-formylpyridin-3-yl)-2-(3-methoxyphenyl)-4-oxo-4H-quinazolin-3-yl]-N-isopropylacetamide (45 mg, 0.10 mmol) in methanol (2 mL) was added azetidine hydrochloride (15 mg, 0.16 mmol), triethyl amine (50 µL, excess) and trimethyl orthoformate (2 mL). The mixture was heated at 60° C. for 30 min. The mixture was cooled to room temperature and sodium cyanoborohydride (50 mg, excess) was added. The mixture was stirred at room temperature for 18 h. The mixture was then concentrated in vacuo, the crude residue dissolved in dichloromethane and washed with 1 N NaOH (aq.) (1×20 mL). The organic layer was concentrated in vacuo and the resulting oil purified by chromatography on silica gel with a gradient on a silica gel column, eluting with a gradient gradient of methanol:dichloromethane (1:19, v/v) to methanol:dichloromethane (1:9, v/v) as eluent. The compound was further purified by preparatory HPLC to afford 2-[6-(5-azetidin-1-ylmethylfuran-2-yl)-2-(3-methoxyphenyl)-4-oxo-4H-quinazolin-3-yl]-N-isopropylacetamide (EXAMPLE 9a) as the TFA salt (5 mg, 0.01 mmol, 10%).

Data for 2-[6-(5-Azetidin-1-ylmethylfuran-2-yl)-2-(3-methoxyphenyl)-4-oxo-4H-quinazolin-3-yl]-N-isopropylacetamide (EXAMPLE 9a): ¹H NMR (300 MHz, CD₃OD) δ 8.59 (d, 1H), 8.22 (dd, 1H), 8.05 (d, 1H), 7.77 (d, 1H), 7.48 (app t, 1H), 7.18 (m, 3H), 7.06 (d, 1H), 6.84 (d, 1H), 4.63 (s, 2H), 4.57 (s, 2H), 4.27 (m, 4H), 3.93 (m, 1H), 3.86 (s, 3H), 2.70-2.40 (m, 2H), 1.12 (d, 6H) ppm; MS (ESI) m/z: 487 ([M+H]⁺)

Example 9b was prepared in a similar manner:

Example 9b

2-[6-(5-Dimethylaminomethylpyridin-3-yl)-2-(3-methoxyphenyl)-4-oxo-4H-quinazolin-3-yl]-N-isopropylacetamide, MS (ESI) m/z: 486 ([M+H]⁺) (from INTERMEDIATE IV.24 and 5-formylpyridine-3-boronic acid pinacol ester (Frontier Scientific))

Example 10a

N-tert-Butyl-2-[2-(3-chlorophenyl)-4-oxo-6-(4-pyrrolidin-1-ylbut-1-enyl)-4H-quinazolin-3-yl]acetamide

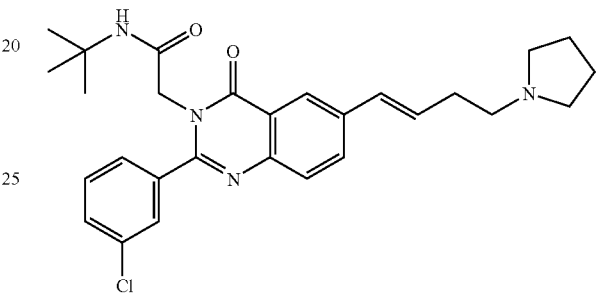

a) N-tert-Butyl-2-[2-(3-chlorophenyl)-6-(4-hydroxybut-1-enyl)-4-oxo-4H-quinazolin-3-yl]acetamide

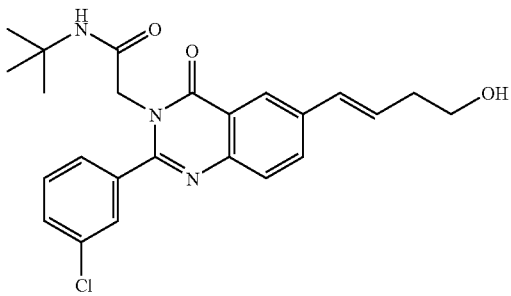

A solution of palladium (II) acetate (82 mg, 0.37 mmol, 10 mol %) and tris (o-tolyl)phosphine (145 mg, 0.48 mmol) in anhydrous acetonitrile (40 mL) was sparged with argon for 5 minutes. Triethylamine (5.10 mL, 36.60 mmol) was added, followed by N-tert-butyl-2-[2-(3-chlorophenyl)-6-iodo-4-oxo-4H-quinazolin-3-yl]acetamide (INTERMEDIATE IV.12) (1.81 g, 3.66 mmol) and 3-buten-1-ol (1.57 mL, 18.30 mmol). The resultant mixture was heated at reflux temperature for 18 h. The resultant green suspension was concentrated in vacuo, and the residue was treated with ethyl acetate (100 mL) and filtered. The black precipitate was washed with ethyl acetate (2×50 mL), and the combined filtrates were washed with 1N HCl (aq.) (2×100 mL), brine (100 mL), dried (MgSO₄) and concentrated to give the crude product as yellow-orange foam. Trituration with ether provided N-tert-butyl-2-[2-(3-chlorophenyl)-6-(4-hydroxybut-1-enyl)-4-oxo-4H-quinazolin-3-yl]acetamide (766 mg, 1.74 mmol, 48%) as an off-white powder.

Data for N-tert-butyl-2-[2-(3-chlorophenyl)-6-(4-hydroxybut-1-enyl)-4-oxo-4H-quinazolin-3-yl]acetamide: $^1$H NMR (300 MHz, CDCl$_3$): δ 8.24 (d, 1H), 7.81 (dd, 1H), 7.69-7.64 (m, 2H), 7.59-7.40 (m, 3H), 6.62 (d, 1H), 6.39 (dt, 1H), 5.54 (br s, 1H), 4.46 (s, 2H), 3.81 (t, 2H), 2.55 (dt, 2H), 2.16 (s, 1H), 1.35 (s, 9H) ppm; MS (ESI) m/z: 440/442 ([M+H]$^+$).

b) Methanesulfonic acid 4-[3-(tert-butylcarbamoylmethyl)-2-(3-chlorophenyl)-4-oxo-3,4-dihydroquinazolin-6-yl]but-3-enyl ester

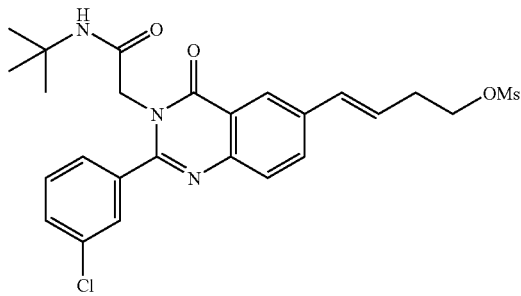

Methanesulfonyl chloride (114 μL, 1.46 mmol) was added to a stirred solution of N-tert-butyl-2-[2-(3-chlorophenyl)-6-(4-hydroxybut-1-enyl)-4-oxo-4H-quinazolin-3-yl]acetamide (536 mg, 1.22 mmol) and triethylamine (510 μL, 3.66 mmol) in dry dichloromethane (12 mL) at 0° C. The cooling bath was removed after 2 h, and the mixture was stirred for an additional 3 h at room temperature. The reaction mixture was diluted with ethyl acetate (40 mL), and washed with 1 N HCl (aq.) (25 mL), sat. NaHCO$_3$ (aq.) (25 mL) and brine (25 mL). The organic layer was dried (MgSO$_4$) and concentrated in vacuo to afford methanesulfonic acid 4-[3-(tert-butylcarbamoylmethyl)-2-(3-chlorophenyl)-4-oxo-3,4-dihydroquinazolin-6-yl]but-3-enyl ester (528 mg, 1.02 mmol, 84%) as a yellow foam.

Data for methanesulfonic acid 4-[3-(tert-butylcarbamoylmethyl)-2-(3-chlorophenyl)-4-oxo-3,4-dihydroquinazolin-6-yl]but-3-enyl ester: $^1$H NMR (300 MHz, CDCl$_3$): δ 8.24 (d, 1H), 7.80 (dd, 1H), 7.69 (d, 1H), 7.64 (dd, 1H), 7.55 (ddd, 1H), 7.48 (dd, 1H), 7.41 (d, 1H), 6.65 (d, 1H), 6.38 (dt, 1H), 5.50 (br s, 1H), 4.47 (s, 2H), 4.37 (t, 2H), 3.04 (s, 3H), 2.73 (dt, 2H), 1.35 (s, 9H) ppm; MS (ESI) m/z: 518/520 ([M+H]$^+$), 1035/1039 ([2M+H]$^+$).

c) N-tert-butyl-2-[2-(3-chlorophenyl)-4-oxo-6-(4-pyrrolidin-1-ylbut-1-enyl)-4H-quinazolin-3-yl]acetamide

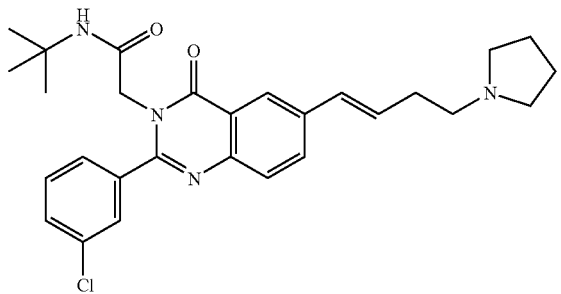

A suspension of methanesulfonic acid 4-[3-(tert-butylcarbamoylmethyl)-2-(3-chlorophenyl)-4-oxo-3,4-dihydroquinazolin-6-yl]but-3-enyl ester (528 mg, 1.02 mmol), pyrrolidine (260 μL, 3.06 mmol), and K$_2$CO$_3$ (705 mg, 5.10 mmol) in dry acetonitrile (5 mL) was heated at reflux temperature for 4 h. The mixture was partitioned between water (10 mL) and ethyl acetate (10 mL). The layers were separated, and the aqueous phase was extracted with ethyl acetate (10 mL). The combined organic layers were washed with brine (10 mL), dried (MgSO$_4$) and concentrated in vacuo to give the crude product as red-brown foam. Chromatography on silica gel with methanol:dichloromethane:NH$_4$OH (aq.) (2:37:1, v/v) as eluent afforded N-tert-butyl-2-[2-(3-chlorophenyl)-4-oxo-6-(4-pyrrolidin-1-ylbut-1-enyl)-4H-quinazolin-3-yl]acetamide (EXAMPLE 10a) (308 mg, 0.62 mmol, 61%) as a yellow foam.

Data for N-tert-butyl-2-[2-(3-chlorophenyl)-4-oxo-6-(4-pyrrolidin-1-ylbut-1-enyl)-4H-quinazolin-3-yl]acetamide (EXAMPLE 10a): $^1$H NMR (300 MHz, CDCl$_3$): δ 8.22 (d, 1H), 7.80 (dd, 1H), 7.68 (s, 1H), 7.64 (dd, 1H), 7.55 (dt, 1H), 7.47 (dd, 1H), 7.43 (d, 1H), 6.56 (d, 1H), 6.41 (dt, 1H), 5.55 (br s, 1H), 4.46 (s, 2H), 2.65-2.46 (m, 8H), 1.83-2.46 (m, 4H), 1.35 (s, 9H) ppm; MS (ESI) m/z: 493/495 ([M+H]$^+$), 985/989 ([2M+H]$^+$).

The following compounds (Examples 10b-10d) were prepared in a similar manner:

Example 10b

N-Isopropyl-2-[2-(3-methoxyphenyl)-6-(4-morpholin-4-ylbut-1-enyl)-4-oxo-4H-quinazolin-3-yl]acetamide, MS (ESI) m/z: 491 ([M+H]$^+$) (from INTERMEDIATE IV.24)

Example 10c

N-Isopropyl-2-[2-(3-methoxyphenyl)-4-oxo-6-(4-piperidin-1-ylbut-1-enyl)-4H-quinazolin-3-yl]acetamide, MS (ESI) m/z: 489 ([M+H]$^+$) (from INTERMEDIATE IV.24)

Example 10d

N-isopropyl-2-[2-(3-methoxyphenyl)-4-oxo-6-(4-pyrrolidin-1-ylbut-1-enyl)-4H-quinazolin-3-yl]acetamide: MS (ESI) m/z: 475 ([M+H]$^+$) (from INTERMEDIATE IV.24)

Example 11a

N-tert-Butyl-2-[2-(3-chlorophenyl)-4-oxo-6-(4-pyrrolidin-1-ylbutyl)-4H-quinazolin-3-yl]acetamide

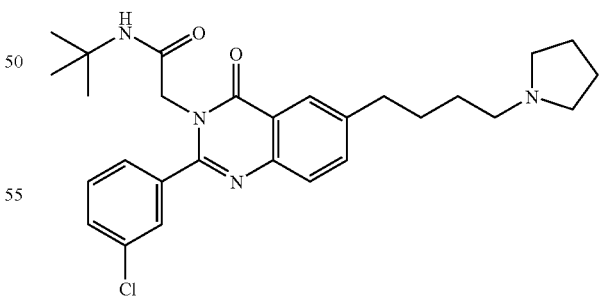

A solution of N-tert-butyl-2-[2-(3-chlorophenyl)-4-oxo-6-(4-pyrrolidin-1-ylbut-1-enyl)-4H-quinazolin-3-yl]acetamide (EXAMPLE 10a) (303 mg, 0.62 mmol) in dry methanol (6 mL) was sparged (5 min) with argon, and 10% Pd/C (24 mg, catalytic) was added. The reaction mixture was stirred under a hydrogen atmosphere(1 atm.) for 4 h at room temperature. The mixture was filtered through CELITE™, and the filter cake was washed with methanol (3×10 mL). The filtrates were evaporated under reduced pressure to afford N-tert-butyl-2-[2-(3-chlorophenyl)-4-oxo-6-(4-pyrrolidin-1-ylbutyl)-4H-quinazolin-3-yl]acetamide (EXAMPLE 11a) (223 mg, 0.45 mmol, 73%) as yellow foam.

Data for N-tert-butyl-2-[2-(3-chlorophenyl)-4-oxo-6-(4-pyrrolidin-1-ylbutyl)-4H-quinazolin-3-yl]acetamide (EXAMPLE 11a): $^1$H NMR (300 MHz, CDCl$_3$): δ 8.12 (d, 1H), 7.68-7.61 (m, 3H), 7.56-7.40 (m, 3H), 5.54 (br s, 1H), 4.46 (s, 2H), 2.79 (t, 2H), 2.49-2.45 (m, 5H), 1.80-1.55 (m, 9H), 1.35 (s, 9H) ppm; MS (ESI) m/z: 495/497 ([M+H]$^+$).

The following compounds (Examples 11b-11e) were prepared in a similar manner:

Example 11b

N-Isopropyl-2-[2-(3-methoxyphenyl)-4-oxo-6-(4-pyrrolidin-1-ylbutyl)-4H-quinazolin-3-yl]acetamide, MS (ESI) m/z: 477 ([M+H]$^+$) (from Example 10d)

Example 11c

N-Isopropyl-2-[2-(3-methoxyphenyl)-6-(4-morpholin-4-ylbutyl)-4-oxo-4H-quinazolin-3-yl]acetamide, MS (ESI) m/z: 493 ([M+H]$^+$) (from Example 10b)

Example 11d

N-tert-Butyl-2-[2-(4-fluoro-3-methoxyphenyl)-4-oxo-6-(4-piperidin-1-ylbutyl)-4H-quinazolin-3-yl]acetamide, MS (ESI) m/z: 523 ([M+H]$^+$) (from N-tert-butyl-2-[2-(4-fluoro-3-methoxyphenyl)-4-oxo-6-(4-piperidin-1-yl but-1-enyl)-4H-quinazolin-3-yl]acetamide prepared according to the procedure used to prepare Example 10a from INTERMEDIATE IV.26)

Example 11e

N-tert-Butyl-2-[2-(4-fluoro-3-methoxyphenyl)-4-oxo-6-(4-pyrrolidin-1-ylbutyl)-4H-quinazolin-3-yl]acetamide, MS (ESI) m/z: 509 ([M+H]$^+$) (from N-tert-butyl-2-[2-(4-fluoro-3-methoxyphenyl)-4-oxo-6-(4-pyrrolidin-1-yl but-1-enyl)-4H-quinazolin-3-yl]acetamide prepared according to the procedure used to prepare Example 10a from INTERMEDIATE IV.26)

Example 12a

N-Isopropyl-2-[2-(3-methoxyphenyl)-6-[2-(1-methylpiperidin-2-yl)ethoxy]-4-oxo-4H-quinazolin-3-yl]acetamide a) 2-[2-[3-(Isopropylcarbamoylmethyl)-2-(3-methoxyphenyl)-4-oxo-3,4-dihydroquinazolin-6-yloxy]ethyl]piperidine-1-carboxylic acid tert-butyl ester

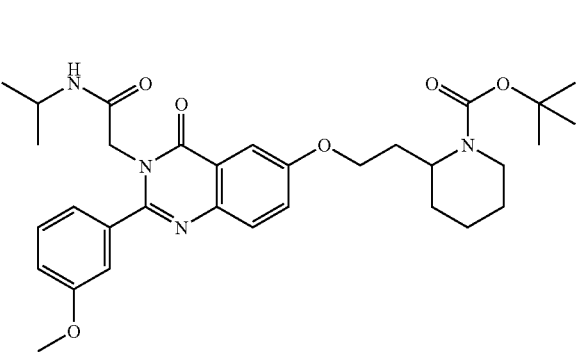

A mixture of 2-[6-hydroxy-2-(3-methoxy-phenyl)-4-oxo-4H-quinazolin-3-yl]-N-isopropyl-acetamide (INTERMEDIATE IV.4) (200 mg, 0.55 mmol), N-Boc-2-piperidine ethanol (250 mg, 1.09 mmol) and resin-bound triphenylphosphine (~3 mmol/g, 543 mg, 1.63 mmol) in dichloromethane (4.5 mL) and DMF (0.5 mL) was cooled to 0° C. and diisopropylazodicarboxylate (DIAD) (0.21 mL, 1.09 mmol) was added dropwise with stirring. The reaction mixture was allowed to warm to room temperature and stirring was continued for 16 h. The mixture was then filtered and concentrated in vacuo. The crude residue was dissolved in dichloromethane (100 mL) and washed with 1 N NaOH (aq.) and brine. The organic phase was dried (MgSO$_4$), filtered and concentrated in vacuo. Purification by chromatography on silica gel with ethyl acetate:hexane (2:1, v/v) afforded 2-{2-[3-(isopropylcarbamoylmethyl)-2-(3-methoxyphenyl)-4-oxo-3,4-dihydroquinazolin-6-yloxy]ethyl}piperidine-1-carboxylic acid tert-butyl ester (65 mg, 0.11 mmol, 20%).

Data for 2-{2-[3-(isopropylcarbamoylmethyl)-2-(3-methoxyphenyl)-4-oxo-3,4-dihydroquinazolin-6-yloxy]ethyl}piperidine-1-carboxylic acid tert-butyl ester: $^1$H NMR (300 MHz, CDCl$_3$) δ 7.69 (d, 1H), 7.62 (d, 1H), 7.37 (m, 2H), 7.18 (m, 2H), 7.02 (dd, 1H), 5.64 (br d, 1H, amide N$\underline{H}$), 4.52 (s, 2H), 4.09 (m, 3H), 3.83 (s, 3H), 2.82 (br t, 1H), 2.25 (m, 1H), 1.95 (m, 1H), 1.62 (m, 8H), 1.40 (s, 9H), 1.16 (d, 6H) ppm; MS (ESI) m/z: 579 ([M+H]$^+$), 523 ([M-t-Bu]$^+$).

b) N-Isopropyl-2-[2-(3-methoxyphenyl)-4-oxo-6-(2-piperidin-2-ylethoxy)-4H-quinazolin-3-yl]acetamide

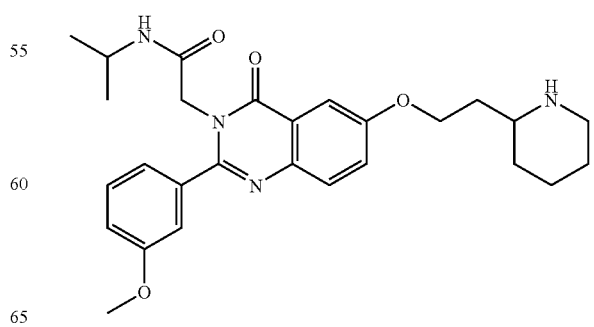

2-{2-[3-(Isopropylcarbamoylmethyl)-2-(3-methoxyphenyl)-4-oxo-3,4-dihydroquinazolin-6-yloxy]ethyl}piperidine-1-carboxylic acid tert-butyl ester (65 mg, 0.11 mmol) was treated with trifluoroacetic acid/dichloromethane (1:1 (v/v), 1 mL) and stirred for 30 minutes. The volatiles were removed in vacuo, the residue partitioned between dichloromethane and 1 N NaOH (aq.) and the aqueous phase washed with dichloromethane. The combined organic layers were dried (MgSO$_4$), filtered and concentrated in vacuo. The crude N-isopropyl-2-[2-(3-methoxyphenyl)-4-oxo-6-(2-piperidin-2-ylethoxy)-4H-quinazolin-3-yl]acetamide was used in the next step without further purification.

Data for N-isopropyl-2-[2-(3-methoxyphenyl)-4-oxo-6-(2-piperidin-2-ylethoxy)-4H-quinazolin-3-yl]acetamide: MS (ESI) m/z: 479 ([M+H]$^+$).

c) N-Isopropyl-2-[2-(3-methoxyphenyl)-6-[2-(1-methylpiperidin-2-yl)ethoxy]-4-oxo-4H-quinazolin-3-yl]acetamide

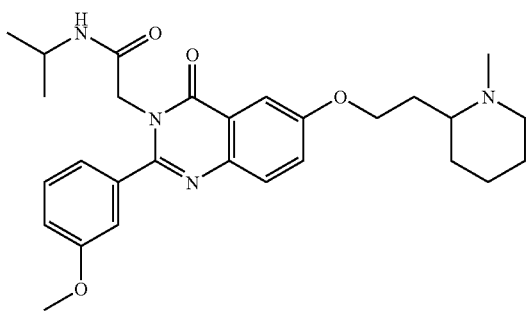

Crude N-isopropyl-2-[2-(3-methoxyphenyl)-4-oxo-6-(2-piperidin-2-ylethoxy)-4H-quinazolin-3-yl]acetamide was treated with 37% formaldehyde (aq.) (0.1 mL) and formic acid (1 mL) and the resultant mixture heated to 95° C. for 5 h. The mixture was then cooled and partitioned between 1N NaOH (aq.) (20 mL) and dichloromethane:2-propanol (3:1 [v/v], 10 mL). The aqueous was extracted with additional dichloromethane: 2-propanol (3:1 [v/v], 3×10 mL). The combined organic phases were dried (MgSO$_4$), filtered and concentrated in vacuo giving N-isopropyl-2-[(2-(3-methoxyphenyl)-6-[2-(1-methylpiperidin-2-yl)ethoxy]-4-oxo-4H-quinazolin-3-yl]acetamide (EXAMPLE 12a) (17 mg, 0.04 mmol, 31% from 2-{2-[3-(Isopropylcarbamoylmethyl)-2-(3-methoxyphenyl)-4-oxo-3,4-dihydroquinazolin-6-yloxy]ethyl}piperidine-1-carboxylic acid tert-butyl ester, >85% pure by HPLC).

Data for N-isopropyl-2-[(2-(3-methoxyphenyl)-6-[2-(1-methylpiperidin-2-yl)ethoxy]-4-oxo-4H-quinazolin-3-yl]acetamide (EXAMPLE 12a): $^1$H NMR (300 MHz, CDCl$_3$) δ 7.69 (m, 2H), 7.39 (m, 2H), 7.18 (m, 2H), 7.03 (dd, 1H), 5.64 (br d, 1H, amide NH), 4.51 (s, 2H), 4.17 (m, 2H), 4.07 (septet, 1H), 3.84 (s, 3H), 2.91 (br d, 1H), 2.35 (s, 3H), 2.2-1.3 (m, 10H), 1.16 (d, 6H) ppm; MS (ESI) m/z: 493 ([M+H]$^+$).

Example 13a

N-Isopropyl-2-[2-(3-methoxyphenyl)-4-oxo-6-(3-piperidin-1-ylpropylamino)-4H-quinazolin-3-yl]acetamide

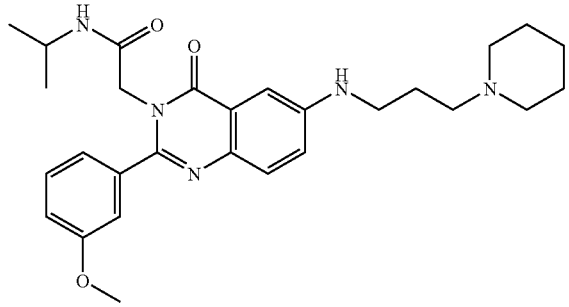

To a solution of N-isopropyl-2-[6-[(4-methoxybenzyl)-(3-piperidin-1-ylpropyl)amino]-2-(3-methoxyphenyl)-4-oxo-4H-quinazolin-3-yl]acetamide (EXAMPLE 3r) (44 mg, 0.07 mmol) in ethanol (7 mL) was added 10% Pd/C (~25 mg, catalytic). The mixture was stirred under an atmosphere of hydrogen (50 p.s.i.) for 18 h. The mixture was filtered through CELITE™ and concentrated in vacuo. The resulting oil was purified by chromatography on a silica gel with methanol:dichloromethane (1:9, v/v) as eluent. The resultant yellow solid was further purified using preparatory HPLC to yield N-isopropyl-2-[2-(3-methoxyphenyl)-4-oxo-6-(3-piperidin-1-ylpropylamino)-4H-quinazolin-3-yl]acetamide (EXAMPLE 13a) (9 mg, 0.02 mmol, 24%) as a yellow solid.

Data for N-isopropyl-2-[2-(3-methoxyphenyl)-4-oxo-6-(3-piperidin-1-ylpropylamino)-4H-quinazolin-3-yl]acetamide (EXAMPLE 13a): MS (ESI) m/z: 492 ([M+H]$^+$)

Example 14a

N-Isopropyl-2-[2-(3-methoxyphenyl)-6-(1-methyl piperidin-3-ylmethoxy)-4-oxo-4H-quinazolin-3-yl]acetamide

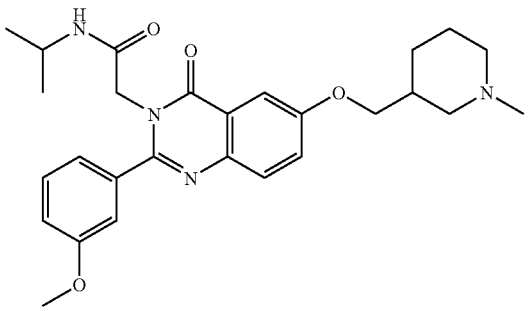

A mixture of 2-[6-hydroxy-2-(3-methoxyphenyl)-4-oxo-4H-quinazolin-3-yl]-N-isopropylacetamide (INTERMEDIATE IV.4) (100 mg, 0.27 mmol), 3-chloromethyl-1-methyl piperidine*HCl (50 mg, 0.27 mmol), caesium carbonate (443 mg, 1.36 mmol) and a catalytic amount of sodium iodide in DMSO (1 mL) was heated to 85° C. for 16 h. This was then cooled and poured into water (10 mL) and the resultant precipitate collected by filtration. Purification by chromatography on silica gel with methanol:dichloromethane:$NH_4OH$ (aq.) (20:179:1, v/v) as eluent afforded N-isopropyl-2-[2-(3-methoxyphenyl)-6-(1-methylpiperidin-3-ylmethoxy)-4-oxo-4H-quinazolin-3-yl]acetamide (EXAMPLE 14a) (82 mg, 0.17 mmol, 63%).

Data for N-isopropyl-2-[2-(3-methoxyphenyl)-6-(1-methylpiperidin-3-ylmethoxy)-4-oxo-4H-quinazolin-3-yl]acetamide (EXAMPLE 14a): $^1$H NMR (300 MHz, $CDCl_3$) δ 7.67 (d, 1H), 7.61 (d, 1H), 7.36 (m, 2H), 7.15 (m, 2H), 7.01 (dd, 1H), 5.58 (brd, 1H, amide NH), 4,48 (s, 2H), 4.09 (septet, 1H), 3.93 (m, 2H), 3.81 (s, 3H), 2.97 (m, 1H), 2.76 (m, 1H), 2.29 (br s, 3H), 2.20 (m, 1H), 2.0-1.6 (m, 6H), 1.14 (d, 6H) ppm; MS (ESI) m/z: 479 ([M+H]$^+$).

EXAMPLE 14b was prepared in a similar manner:

Example 14b

N-Isopropyl-2-[2-(3-methoxyphenyl)-4-oxo-6-(pyridin-3-ylmethoxy)-4H-quinazolin-3-yl]acetamide, MS (ESI) m/z: 459 ([M+H]$^+$) (from INTERMEDIATE IV.4)

Example 15

Chinese Hamster Ovary (CHO) cells stably expressing the human $V_3$ receptor were incubated to equilibrium with the test compound (at a final assay concentration of $10^{-11}$ mol.L$^{-1}$ to $10^{-5}$ mol.L$^{-1}$) and [$^3$H]AVP (at a final assay concentration of $2.5\times10^{-9}$ mol.L$^{-1}$). Throughout the concentration of dimethylsulphoxide (DMSO) did not exceed 0.1% (v/v). After washing with ice-cold phosphate buffered saline (PBS), scintillation fluid was added and the plates counted on a Topcount NXT apparatus.

A sigmoidal dose response curve (non-linear regression, variable slope) was plotted as concentration of test compound (mol.L$^{-1}$) against percentage specific binding of [$^3$H]AVP and a $K_i$ value was calculated. Each determination was carried out in triplicate and repeated on at least 3 separate occasions Table 1 shows the binding activity obtained for some representative compounds of the invention.

TABLE 1

| $V_3$ binding activity for compounds according to the invention | | |
|---|---|---|
| EXAMPLE 1f: N-Isopropyl-2-[4-oxo-6-(3-piperidin-1-ylpropoxy)-2-(3,4,5-trifluorophenyl)-4H-quinazolin-3-yl]acetamide | 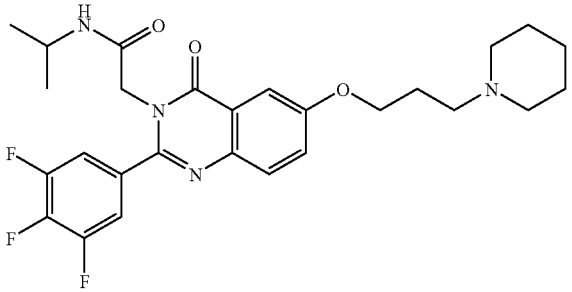 | ++ |
| EXAMPLE 1h: N-Isopropyl-2-[2-(6-methoxypyridin-2-yl)-4-oxo-6-(3-piperidin-1-ylpropoxy)-4H-quinazolin-3-yl]acetamide | 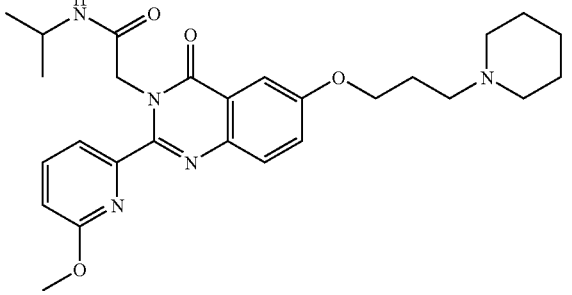 | +++ |
| EXAMPLE 2f: N-tert-Butyl-2-[2-(3-chlorophenyl)-4-oxo-6-(3-piperidin-1-ylpropoxy)-4H-quinazolin-3-yl]acetamide | 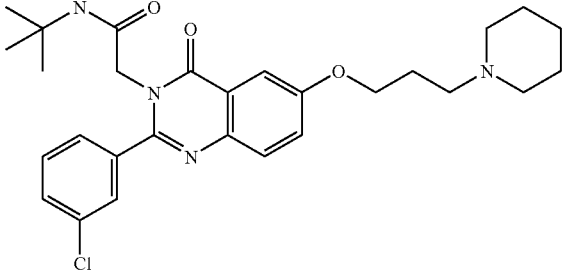 | +++ |

TABLE 1-continued

V₃ binding activity for compounds according to the invention

EXAMPLE 2p: 2-{2-(4-Fluoro-3-methoxyphenyl)-6-[3-(4-hydroxypiperidin-1-yl)propoxy]-4-oxo-4H-quinazolin-3-yl}-N-isopropylacetamide

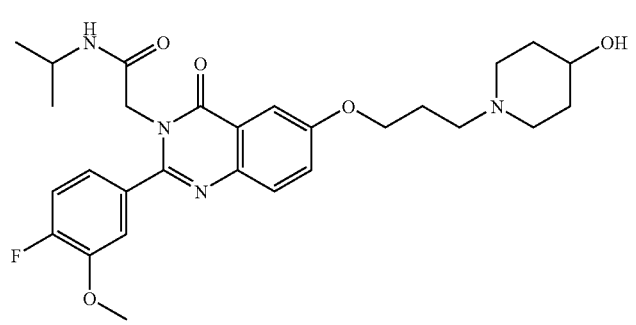

+++

EXAMPLE 2w: N-isopropyl-2-[2-(3-methoxyphenyl)-7-methyl-4-oxo-6-(3-piperidin-1-ylpropoxy)-4H-quinazolin-3-yl]acetamide

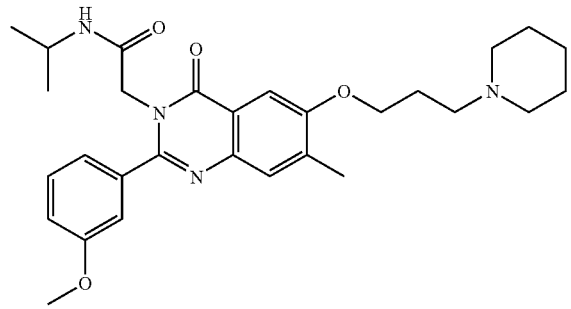

+++

EXAMPLE 3a: 2-[2-(3-Chlorophenyl)-4-oxo-6-(3-piperidin-1-ylpropoxy)-4H-quinazolin-3-yl]-N-isopropylacetamide hydrochloride

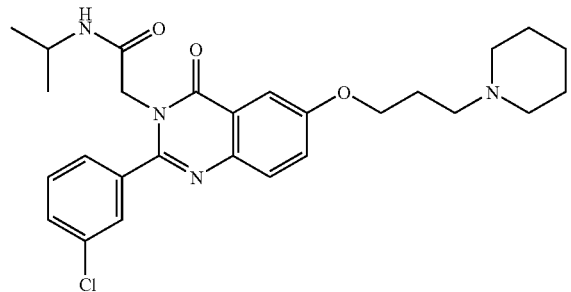

+++

EXAMPLE 3k: N-Cyclopropylmethyl-2-[2-(3,5-dimethoxyphenyl)-6-(3-morpholin-4-ylpropoxy)-4-oxo-4H-quinazolin-3-yl]acetamide

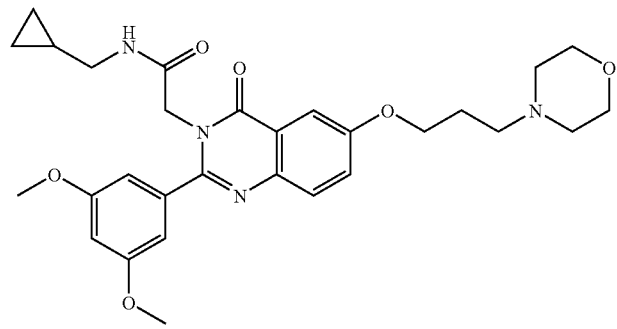

+++

TABLE 1-continued

V₃ binding activity for compounds according to the invention

EXAMPLE 3r: N-Isopropyl-2-[6-[(4-methoxybenzyl)-(3-piperidin-1-ylpropyl)amino]-2-(3-methoxyphenyl)-4-oxo-4H-quinazolin-3-yl]acetamide

++

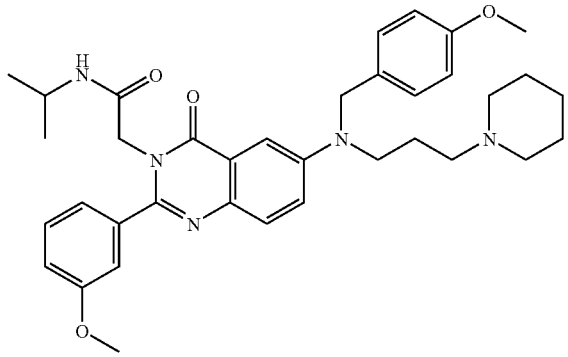

EXAMPLE 3t: N-Isopropyl-2-[2-(3-methoxyphenyl)-4-oxo-6-(3-piperidin-1-ylpropylsulfanyl)-4H-quinazolin-3-yl]acetamide

++

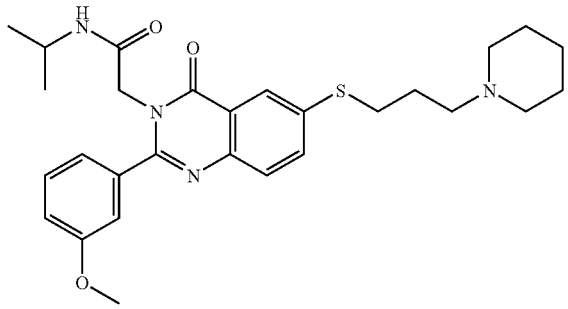

EXAMPLE 4g: (S)-(+)-2-[2-(3-Fluorophenyl)-6-(2-methyl-3-morpholin-4-ylpropoxy)-4-oxo-4H-quinazolin-3-yl]-N-isopropylacetamide

+++

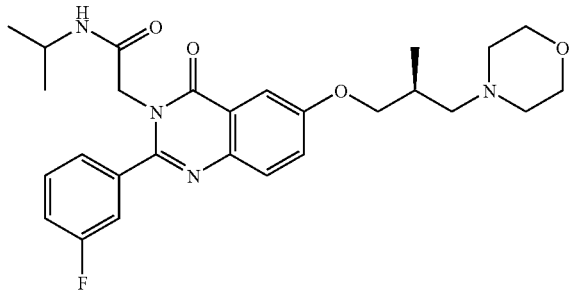

EXAMPLE 4i: (S)-(+)-2-[6-(3-Azetidin-1-yl-2-methylpropoxy)-2-(3-methoxyphenyl)-4-oxo-4H-quinazolin-3-yl]-N-isopropylacetamide

++

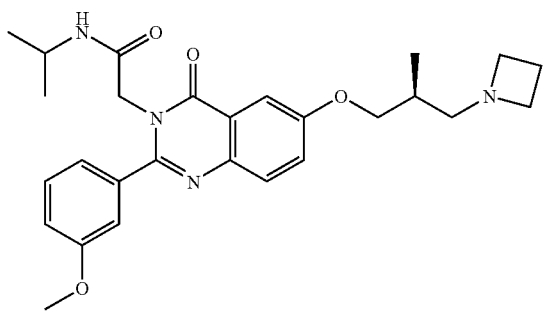

TABLE 1-continued

V₃ binding activity for compounds according to the invention

| EXAMPLE 4n: (S)-(+)-2-[2-(3-Methoxyphenyl)-6-(2-methyl-3-piperidin-1-ylpropoxy)-4-oxo-4H-quinazolin-3-yl]-N-propylacetamide | 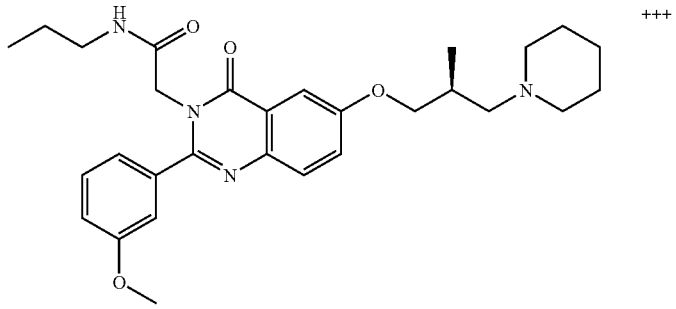 | +++ |
| --- | --- | --- |
| EXAMPLE 4q: (S)-(+)-2-[6-(3-Azepan-1-ylpropoxy)-4-oxo-2-phenyl-4H-quinazolin-3-yl]-N-cyclopropylmethylacetamide | 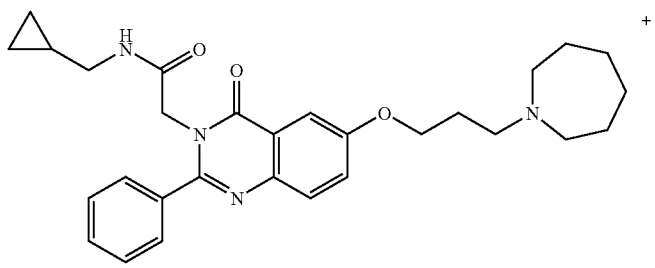 | + |
| EXAMPLE 6a: 2-[6-(5-Dimethylaminomethyl-2-fluorophenyl)-2-(3-methoxyphenyl)-4-oxo-4H-quinazolin-3-yl]-N-isopropylacetamide | 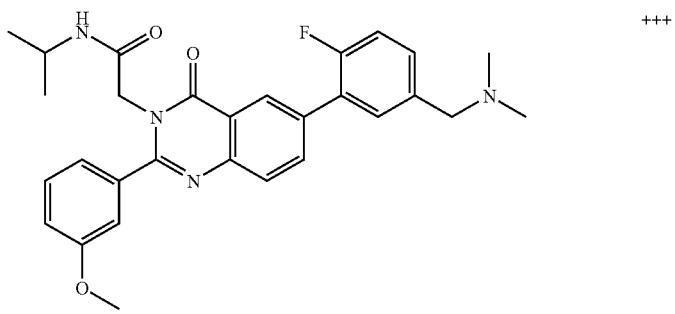 | +++ |
| EXAMPLE 6b: 2-[6-(6-Dimethylaminomethylpyridin-2-yl)-2-(3-methoxyphenyl)-4-oxo-4H-quinazolin-3-yl]-N-isopropylacetamide | 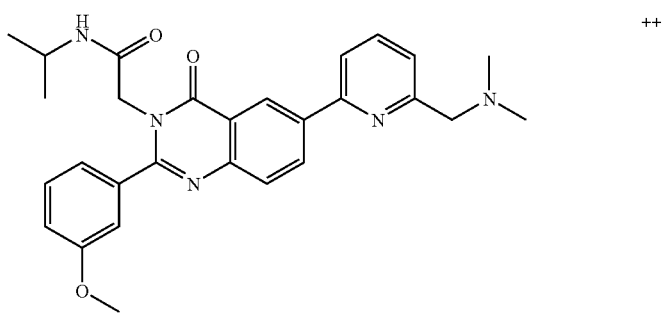 | ++ |
| EXAMPLE 7p: 2-[6-{3-[(Isobutylmethylamino)methyl]phenyl}-2-(3-methoxyphenyl)-4-oxo-4H-quinazolin-3-yl]-N-isopropylacetamide | 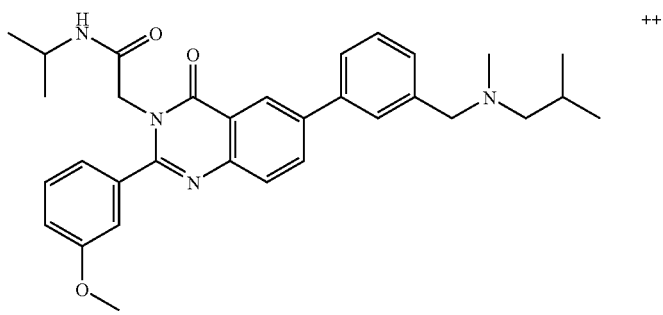 | ++ |

TABLE 1-continued

V₃ binding activity for compounds according to the invention

| | | |
|---|---|---|
| EXAMPLE 7u: N-Isopropyl-2-[2-(3-methoxyphenyl)-6-(3-morpholin-4-ylmethylphenyl)-4-oxo-4H-quinazolin-3-yl]acetamide | 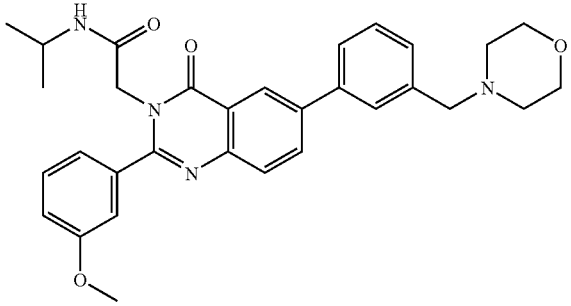 | +++ |
| EXAMPLE 7x: N-Allyl-2-[4-oxo-2-phenyl-6-(3-piperidin-1-ylmethylphenyl)-4H-quinazolin-3-yl]acetamide | 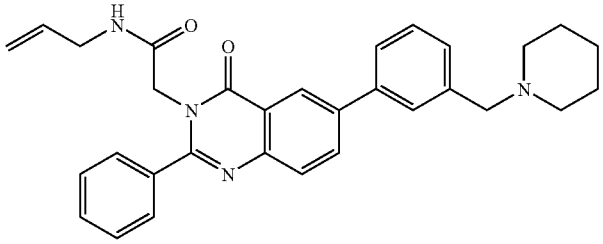 | + |
| EXAMPLE 9a: 2-[6-(5-Azetidin-1-ylmethylfuran-2-yl)-2-(3-methoxyphenyl)-4-oxo-4H-quinazolin-3-yl]-N-isopropylacetamide | 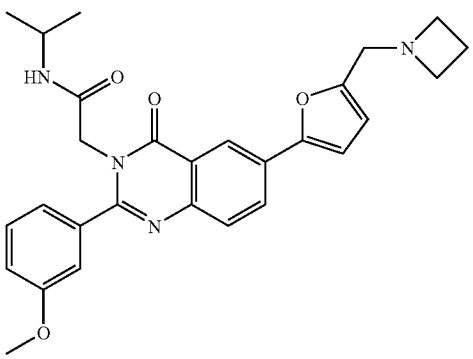 | ++ |
| EXAMPLE 10b: N-Isopropyl-2-[2-(3-methoxyphenyl)-6-(4-morpholin-4-ylbut-1-enyl)-4-oxo-4H-quinazolin-3-yl]acetamide | 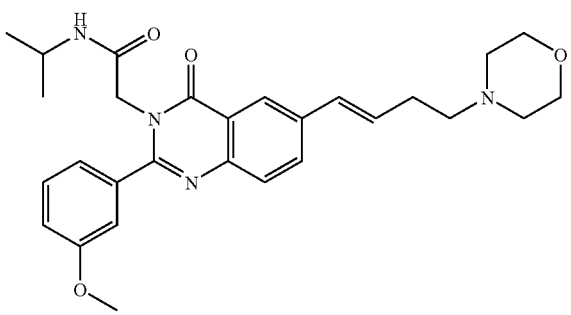 | ++ |
| EXAMPLE 11b: N-Isopropyl-2-[2-(3-methoxyphenyl)-4-oxo-6-(4-pyrrolidin-1-ylbutyl)-4H-quinazolin-3-yl]acetamide | 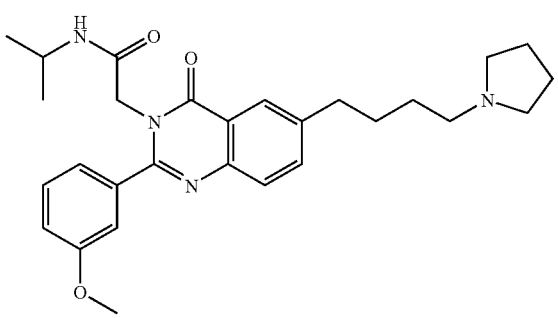 | ++ |

TABLE 1-continued

V₃ binding activity for compounds according to the invention

| | | |
|---|---|---|
| EXAMPLE 12a: N-Isopropyl-2-{2-(3-methoxyphenyl)-6-[2-(1-methylpiperidin-2-yl)ethoxy]-4-oxo-4H-quinazolin-3-yl}acetamide | 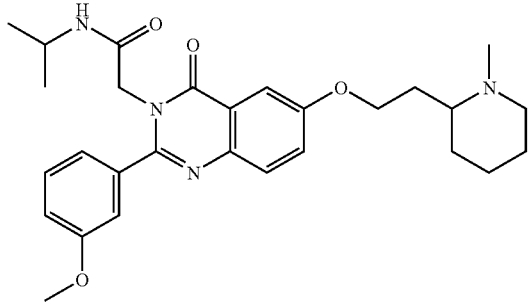 | + |
| EXAMPLE 13a: N-Isopropyl-2-[2-(3-methoxyphenyl)-4-oxo-6-(3-piperidin-1-ylpropylamino)-4H-quinazolin-3-yl]acetamide | 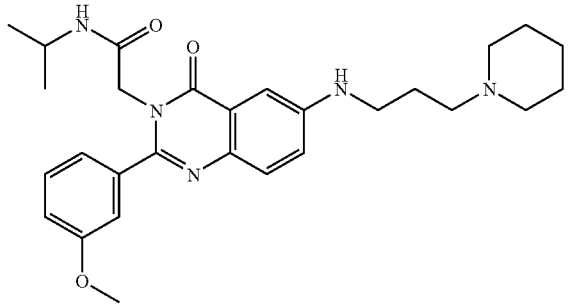 | + |
| EXAMPLE 14a: N-Isopropyl-2-[2-(3-methoxyphenyl)-6-(1-methylpiperidin-3-ylmethoxy)-4-oxo-4H-quinazolin-3-yl]acetamide | 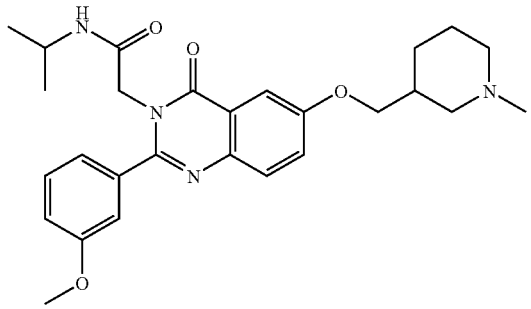 | + |

+++ 0-10 nM
++ 10-100 nM
+ 100 nM-1 uM

The ability of compounds of the invention to act as V3 antagonists in a physiologically relevant system was determined by measuring their ability to block the release of adrenocorticotropic hormone (ACTH) from anterior pituitary corticotrophs in response to treatment with arginine vasopressin (AVP).

Anterior pituitary corticotrophs were prepared from adult female Sprague-Dawley rats and seeded into 48 well plates. The cells were cultured for 4 days prior to exposure to compound. Test compounds were prepared at $10^{-5}$ mol.L$^{-1}$ in 100% DMSO. Cells were exposed to a dose response of test compounds for 20 minutes ($10^{-8}$ mol.L$^{-1}$-$10^{-5}$ mol.L$^{-1}$). The final concentration of DMSO in the assay was kept constant at 0.3%. The cells were then exposed to $3\times10^{-9}$ mol.L$^{-1}$ AVP for 120 minutes. Supernatants were harvested and stored at −20° C. ACTH levels were subsequently measured by ELISA following the manufacturer's instructions (Immunodiagnostic systems, UK (Cat No. DX-SDX018)). Each treatment was carried out in quadruplicate and a mean value obtained for the amount of ACTH released. The degree of antagonism was then calculated as a percentage of the amount of ACTH released by agonist alone after adjustment for basal levels of ACTH. A pIC$_{50}$ was calculated by fitting a Sigmoidal dose response (variable slope) curve with a non-linear (fit) to the data using the software package GraphPad prism. Each determination was repeated on at least 3 separate occasions Table 2 shows the activity obtained for some representative compounds of the invention.

TABLE 2

V₃ receptor antagonism in isolated rat anterior pituitary cells for compounds according to the invention

| | | |
|---|---|---|
| EXAMPLE 2h: N-Isopropyl-2-[2-(3-methoxyphenyl)-4-oxo-6-(3-piperidin-1-ylpropoxy)-4H-quinazolin-3-yl]acetamide | 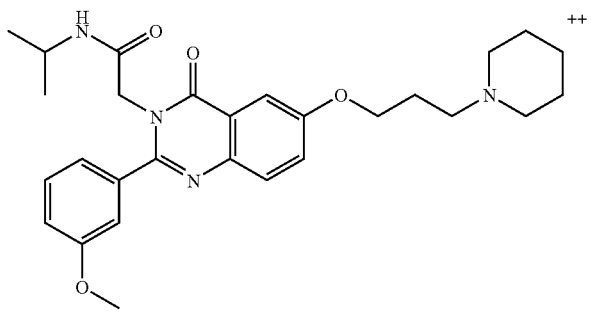 | ++ |
| EXAMPLE 7k: 2-[6-(3-Dimethylaminomethylphenyl)-2-(3-methoxyphenyl)-4-oxo-4H-quinazolin-3-yl]-N-isopropylacetamide | 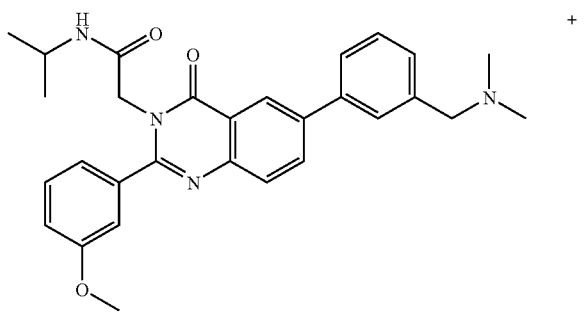 | + |

++ 10-100 nM
+ 100 nM-1 μM

What is claimed:

1. A 2-(4-oxo-4H-quinazolin-3-yl)acetamide compound of formula I,

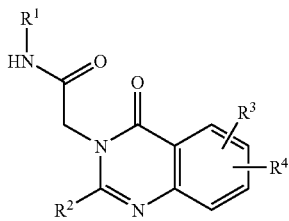

formula I wherein $R^1$ is $C_{1-6}$alkyl, $C_{3-6}$cycloalkyl, $C_{3-6}$cycloalkyl$C_{1-2}$alkyl, $C_{2-6}$alkenyl, $C_{2-6}$alkynyl, phenyl or benzyl, said $C_{1-6}$alkyl, $C_{3-6}$cycloalkyl and $C_{3-6}$cycloalkyl$C_{1-2}$alkyl being optionally substituted with one or more halogens;

$R^2$ is a group selected from $C_{6-10}$aryl optionally substituted with one to three substituents selected from halogen, hydroxy, cyano, COOR¹³, NR¹⁴R¹⁵, pyrrole, $C_{1-6}$alkyl, $C_{3-6}$cycloalkyl, $C_{1-6}$alkyloxy and $C_{3-6}$cycloalkyloxy, said $C_{1-6}$alkyl, $C_{3-6}$cycloalkyl, $C_{1-6}$ alkyloxy and $C_{3-6}$cycloalkyloxy being optionally substituted with one or more halogens, wherein R¹³ and R¹⁴ are independently H or $C_{1-6}$alkyl and R¹⁵ is H, $C_{1-6}$alkyl or $C_{1-6}$acyl, and $C_{4-7}$cycloalkyl or $R^2$ is a 5-10 membered heteroaryl ring system comprising a heteroatom selected from N, O and S optionally substituted with a substituent selected from methyl, $C_{1-6}$alkyloxy and halogen;

$R^3$ is one or two substituents selected from H, $C_{1-6}$alkyl, $C_{1-6}$alkyloxy and halogen, said $C_{1-6}$alkyl and $C_{1-6}$alkyloxy being optionally substituted with one or more halogens;

$R^4$ is a group located at the 6- or 7-position of the quinazoline ring and is selected from

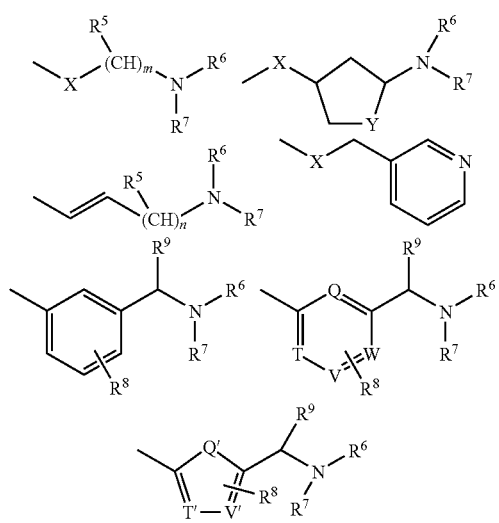

each $R^5$ is independently H or $C_{1-6}$alkyl or one of $R^5$ when joined together with one of $R^6$ or $R^7$ forms a 5-6 membered heterocyclic ring;

$R^6$ and $R^7$ are independently H, $C_{1-6}$alkyl, $C_{3-6}$cycloalkyl, $C_{3-6}$cycloalkyl$C_{1-2}$alkyl, $C_{6-10}$ aryl or $C_{6-10}$aryl$C_{1-2}$alkyl; or $R^6$ and $R^7$ together with the nitrogen to which they are bound form a 4 to 8 membered saturated or unsaturated heterocyclic ring optionally comprising a further heteroatomic moiety selected from O, S and $NR^{10}$, said heterocyclic ring being optionally substituted with one or two substituents selected from halogen, hydroxyl, $C_{1-6}$alkyl, $C_{1-6}$alkyloxy, cyano and $COOR^{11}$ and said heterocyclic ring being optionally fused at two adjacent carbon atoms to a phenyl ring; or one of $R^6$ and $R^7$ when joined together with one of $R^5$ forms a 5-6 membered heterocyclic ring;

$R^8$ is one or two substituents selected from H, $C_{1-6}$alkyl, $C_{1-6}$alkyloxy and halogen or one of $R^8$ when joined together with $R^9$ forms a 5-6 membered ring;

$R^9$ is H or $C_{1-6}$alkyl or $R^9$ when joined together with one of $R^8$ forms a 5-6 membered ring;

$R^{10}$ is H, $C_{1-6}$alkyl or $C_{1-6}$acyl;

$R^{11}$ is H or $C_{1-6}$alkyl;

m is 2-4;

n is 1-2;

X is $CH_2$, O, S, $SO_2$ or $NR^{12}$;

$R^{12}$ is H, $C_{1-6}$alkyl, $C_{1-6}$acyl or a $C_{6-10}$aryl $C_{1-2}$alkyl group, said $C_{6-10}$aryl $C_{1-2}$alkyl group being optionally substituted with methyl or methoxy;

Y is $CH_2$, $(CH_2)_2$ or $(CH_2)_3$;

Q, T, V and W are C or N with the proviso that one of Q, T, V and W is N and the others are C;

Q', T' and V' are selected from C, O, N and S with the proviso that one of Q', T' and V' is O, N, or S and the others are C;

or a pharmaceutically acceptable salt thereof.

2. The 2-(4-oxo-4H-quinazolin-3-yl)acetamide compound according to claim 1, wherein $R^1$ is isopropyl, iso-butyl, tertiary-butyl or cyclopropylmethyl.

3. The 2-(4-oxo-4H-quinazolin-3-yl)acetamide compound according to claim 1, wherein $R^2$ is a 3-substituted phenyl ring.

4. The 2-(4-oxo-4H-quinazolin-3-yl)acetamide compound according to claim 1, wherein $R^2$ is a substituted phenyl ring selected from 3-chlorophenyl, 3-fluorophenyl, 3-methoxyphenyl, 3-trifluoromethoxyphenyl, 3-chloro-4-fluorophenyl, 4-fluoro-3-methoxyphenyl and 3,5-dimethoxyphenyl.

5. The 2-(4-oxo-4H-quinazolin-3-yl)acetamide compound according to claim 1, wherein $R^3$ is a substituent at the 7-position of the quinazoline ring.

6. The 2-(4-oxo-4H-quinazolin-3-yl)acetamide compound according to claim 1, wherein $R^3$ is selected from H, chloro, methyl and methoxy.

7. The 2-(4-oxo-4H-quinazolin-3-yl)acetamide compound according to claim 1, wherein $R^4$ is a substituent at the 6-position of the quinazoline ring.

8. The 2-(4-oxo-4H-quinazolin-3-yl)acetamide compound according to claim 1, wherein $R^4$ is a group selected from

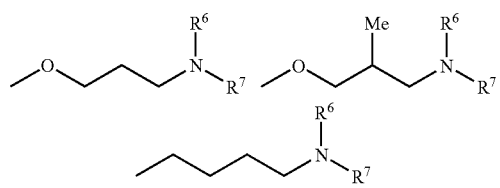

wherein $R^6$ and $R^7$ have the previously defined meanings.

9. The 2-(4-oxo-4H-quinazolin-3-yl)acetamide compound according to claim 1, wherein $R^4$ is a group selected from

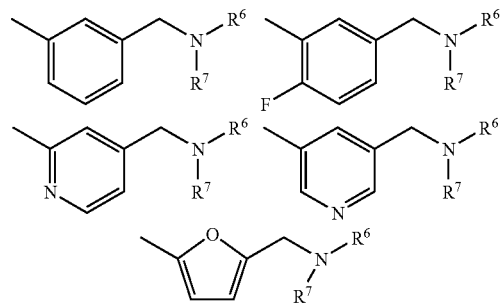

wherein $R^6$ and $R^7$ have the previously defined meanings.

10. The 2-(4-oxo-4H-quinazolin-3-yl)acetamide compound according to claim 1, wherein $R^6$ and $R^7$ are independently H or $C_{1-4}$alkyl.

11. The 2-(4-oxo-4H-quinazolin-3-yl)acetamide compound according to claim 1, wherein $R^6$ and $R^7$ together with the nitrogen to which they are bound form a heterocyclic ring selected from pyrrolidine, piperidine, 3-hydroxypiperidine and morpholine.

12. The 2-(4-oxo-4H-quinazolin-3-yl)acetamide compound according to claim 1 selected from:
 2-[2-(3-Chloro-4-fluorophenyl)-4-oxo-6-(3-piperidin-1-ylpropoxy)-4H-quinazolin-3-yl]-N-isopropylacetamide;
 N-Isopropyl-2-[2-(3-methoxyphenyl)-4-oxo-6-(3-piperidin-1-ylpropoxy)-4H -quinazolin-3-yl]acetamide;
 2-[2-(4-Fluoro-3-methoxyphenyl)-4-oxo-6-(3-pip eridin-1-ylpropoxy)-4H-quinazolin -3-yl]-N-isopropylacetamide;
 2-{2-(3-Chlorophenyl)-6-[3-(4-hydroxypiperidin-1-yl) propoxy]-4-oxo-4H -quinazolin-3-yl}-N-isopropylacetamide;
 2-[2-(3-Chlorophenyl)-4-oxo-6-(3-piperidin-1-ylpropoxy)-4H-quinazolin-3-yl]-N -isopropylacetamide;
 (S)-(+)-2-[2-(3-Chlorophenyl)-6-(2-methyl-3-pyrrolidin-1-ylpropoxy)-4-oxo-4H -quinazolin-3-yl]-N-isopropylacetamide;
 2-[6-(5-Dimethylaminomethyl-2-fluorophenyl)-2-(3-methoxyphenyl)-4-oxo-4H -quinazolin-3-yl]-N-isopropylacetamide;
 2-[6-(3-Dimethylaminomethylphenyl)-2-(3-methoxyphenyl)-4-oxo-4H-quinazolin-3-yl]-N-isopropylacetamide;
 N-tert-Butyl-2-[2-(3-chlorophenyl)-4-oxo-6-(3-pyrrolidin-1-ylpropoxy)-4H -quinazolin-3-yl] acetamide; and
 2-[6-(3-Dimethylaminomethylphenyl)-2-(3-methoxyphenyl)-4-oxo-4H-quinazolin-3-yl]-N-isopropylacetamide;
 or a pharmaceutically acceptable salt thereof.

13. A pharmaceutical composition comprising a 2-(4-oxo-4H-quinazolin-3-yl)acetamide compound according to claim 1 or a pharmaceutically acceptable salt thereof in admixture with one or more pharmaceutically acceptable auxiliaries.

14. The 2-(4-oxo-4H-quinazolin-3-yl)acetamide compound selected from: 2-[2-(3-Chlorophenyl)-4-oxo-6-(3-piperidin-1-ylpropoxy)-4H-quinazolin-3-yl]-N-isopropylacetamide or a pharmaceutically acceptable salt thereof.

15. A pharmaceutical composition comprising a compound according to claim 14 or a pharmaceutically acceptable salt thereof in admixture with one or more pharmaceutically acceptable auxiliaries.

* * * * *